US012636373B2

(12) United States Patent
Miller et al.

(10) Patent No.: US 12,636,373 B2
(45) Date of Patent: May 26, 2026

(54) PRODRUGS WITH A TRIDENTATE SELF-IMMOLATIVE LINKER

(71) Applicant: The General Hospital Corporation, Boston, MA (US)

(72) Inventors: Miles A. Miller, Medford, MA (US); Ralph Weissleder, Peabody, MA (US); Hannes Mikula, Pixendorf (AT)

(73) Assignee: The General Hospital Corporation, Boston, MA (US)

( * ) Notice: Subject to any disclaimer, the term of this patent is extended or adjusted under 35 U.S.C. 154(b) by 886 days.

(21) Appl. No.: 17/312,712

(22) PCT Filed: Dec. 12, 2019

(86) PCT No.: PCT/US2019/066101
§ 371 (c)(1),
(2) Date: Jun. 10, 2021

(87) PCT Pub. No.: WO2020/123882
PCT Pub. Date: Jun. 18, 2020

(65) Prior Publication Data
US 2022/0062428 A1 Mar. 3, 2022

Related U.S. Application Data

(60) Provisional application No. 62/778,837, filed on Dec. 12, 2018.

(51) Int. Cl.

| | |
|---|---|
| ***A61K 47/60*** | (2017.01) |
| ***A61K 47/54*** | (2017.01) |
| ***A61K 47/69*** | (2017.01) |
| ***A61P 35/00*** | (2006.01) |

(52) U.S. Cl.
CPC ............ *A61K 47/60* (2017.08); *A61K 47/542* (2017.08); *A61K 47/6937* (2017.08); *A61P 35/00* (2018.01)

(58) Field of Classification Search
CPC .......................... A61K 47/6937; A61K 47/542
See application file for complete search history.

(56) References Cited

U.S. PATENT DOCUMENTS

| | | | |
|---|---|---|---|
| 5,304,121 | A | 4/1994 | Sahatjian |
| 5,851,778 | A | 12/1998 | Oh et al. |
| 5,886,026 | A | 3/1999 | Hunter et al. |
| 6,099,562 | A | 8/2000 | Ding et al. |
| 6,803,031 | B2 | 10/2004 | Rabinowitz et al. |
| 7,375,078 | B2 | 5/2008 | Feng |
| 9,238,686 | B2 | 1/2016 | Hersel et al. |
| 2004/0091546 | A1 | 5/2004 | Johnson et al. |
| 2016/0310612 | A1 | 10/2016 | Lyon et al. |

FOREIGN PATENT DOCUMENTS

| | | | |
|---|---|---|---|
| WO | WO 2004/043493 | 5/2004 | |
| WO | WO 2005/112919 | 12/2005 | |
| WO | WO 2007/150030 | 12/2007 | |
| WO | WO 2009/017394 | 2/2009 | |
| WO | WO 2012/156918 | 11/2012 | |
| WO | WO 2014/100762 | 6/2014 | |
| WO | WO 2015/038426 | 3/2015 | |
| WO | WO-2015038426 A1 * | 3/2015 | ......... A61K 47/6889 |

OTHER PUBLICATIONS

Neumann et al. "Tetrazine-Responsive Self-immolative Linkers" Chem BioChem 2017, 18, 91-95 (Year: 2017).*
Riley et al. "Core-Shell Structure of PLA-PEG Nanoparticles Used for Drug Delivery" Langmuir, 2003, 19, 8428-8435 (Year: 2003).*
Davies et al. "Bioorthogonal Decaging Reactions for Targeted Drug Activation" Chimia Nov. 30, 2018, 72, 771-776 (Year: 2018).*
Albright et al., "Matrix Metalloproteinase-Activated Doxorubicin Prodrugs Inhibit HT1080 Xenograft Growth Better Than Doxorubicin With Less Toxicity," Mol. Cancer Ther., 2005, 4(5):751-760.
Alouane et al., "Self-Immolative Spacers: Kinetic Aspects, Structure-Property Relationships, and Applications," Angew. Chem. Int. Ed., Jun. 2015, 54(26):7492-7509.
Applegate et al., "plusTipTracker: Quantitative Image Analysis Software for the Measurement of Microtubule Dynamics," J Struct. Biol., Nov. 2011, 176(2):168-184.
Arlauckas et al., "In vivo Imaging Reveals a Tumor-Associated Macrophage-Mediated Resistance Pathway in Anti-PD-1 Therapy," Sci. Transl. Med., May 2017, 9(389):eaa13604, 10 pages.
Baxter et al., "Physiologically Based Pharmacokinetic Model for Specific and Nonspecific Monoclonal Antibodies and Fragments in Normal Tissues and Human Tumor Xenografts in Nude Mice," Cancer Res., Mar. 1994, 54(6):1517-1528.
Blencowe et al., "Self-immolative linkers in polymeric delivery systems," Polym Chem, 2011, 2:773-790.
Elliott et al., "Solid-Phase Synthesis of m-Phenylene Ethynylene Heterosequence Oligomers," J Org. Chem., Jul. 2006, 71(14):5282-5290.

(Continued)

*Primary Examiner* — Bethany P Barham
*Assistant Examiner* — Judith Marie Kamm
(74) *Attorney, Agent, or Firm* — Fish & Richardson P.C.

(57) ABSTRACT

Provided is a compound of Formula (I), or a pharmaceutically acceptable salt thereof, wherein $L^1$, $L^2$, $L^3$, n, m, p, X, T, TR, and D are as described herein, that is a prodrug that can, for example, be encapsulated in a particle, administered to a subject, and its drug payload released by means of an uncaging reaction. Methods of using these compounds to treat diseases advantageously treatable by drug D are also described.

(I)

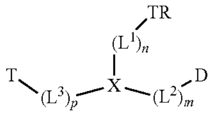

17 Claims, 56 Drawing Sheets

(56) References Cited

OTHER PUBLICATIONS

Finniss et al., "A versatile acid-labile linker for antibody-drug conjugates," MedChemComm, 2014, 5:1355-1358.
Hapuarachchige et al., "Bioorthogonal Two-Component Drug Delivery in HER2(+) Breast Cancer Mouse Models," Sci. Rep. 2016, 6:24298, 10 pages.
Hendriks et al., "Multiscale Kinetic Modeling of Liposomal Doxorubicin Delivery Quantifies the Role of Tumor and Drug-Specific Parameters in Local Delivery to Tumors," CPT Pharmacometrics Syst. Pharmacol., Nov. 2012, 1(11):e15, 11 pages.
Hettrick et al., "Palladium-Catalyzed Oxyhexatriene Cyclization: a Novel Approach to Cyclohexenone Annulation, " J Am. Chem. Soc., 1991, 113(13):4903-4910.
Illum, "Transport of drugs from the nasal cavity to the central nervous system," Eur J Pharm Sci, 2000, 11(1):1-18.
Illum, "Is nose-to-brain transport of drugs in man a reality?," J Pharm Pharmacol, 2004, 56(1):3-17.
International Preliminary Report on Patentability in International Appln. No. PCT/US2019/066101, mailed on Jun. 24, 2021, 6 pages.
International Search Report and Written Opinion in International Appln. No. PCT/US2019/066101, mailed on Feb. 27, 2020, 7 pages.
Jang et al., "Improved Tumor Targeting and Antitumor Activity of Camptothecin Loaded Solid Lipid Nanoparticles By Preinjection of Blank Solid Lipid Nanoparticles," Biomed. Pharmacother., May 2016, 80:162-172.
Klán et al., "Photoremovable Protecting Groups in Chemistry and Biology: Reaction Mechanisms and Efficacy," Chem. Rev., Jan. 2013, 113(1):119-191.
Lee et al., "Cell surface engineering and application in cell delivery to heart diseases," Journal of Biological Engineering, 2018, 12(28):11 pages.
Legigan et al., "The First Generation of β-Galactosidase-Responsive Prodrugs Designed for the Selective Treatment of Solid Tumors in Prodrug Monotherapy," Angew. Chem. Int. Ed. Engl., Nov. 2012, 51(46):11606-11610, 7 pages.
Li and Chen, "Development and Application of Bond Cleavage Reactions in Bioorthogonal Chemistry," Nat. Chem. Biol., Feb. 2016, 12:129-137.
Li et al., "Palladium-Triggered Deprotection Chemistry for Protein Activation in Living Cells," Nat. Chem., 2014, 6:352-361.
Liu et al., "A New Approach to Reduce Toxicities and to Improve Bioavailabilities of Platinum-Containing Anti-Cancer Nanodrugs," Sci. Rep., 2015, 5:10881, 11 pages.
Liu et al., "Decreased Reticuloendothelial System Clearance and Increased Blood Half-Life and Immune Cell Labeling for Nano- and Micron-Sized Superparamagnetic Iron-Oxide Particles Upon Pre-Treatment With Intralipid, "Biochim. Biophys. Acta, 2013, 1830:3447-3453.
Matikonda et al., "Bioorthogonal Prodrug Activation Driven By a Strain-Promoted 1,3-Dipolar Cycloaddition," Chem. Sci., 2015, 6:1212-1218.
Miller et al., "Modular Nanoparticulate Prodrug Design Enables Efficient Treatment of Solid Tumors Using Bioorthogonal Activation," ACS Nano, Dec. 2018, 12(12):12814-12826.
Miller et al., "Nano-Palladium is a Cellular Catalyst for In Vivo Chemistry," Nat Commun, 2017, 8:15906, 13 pages.
Miller et al., "Platinum Compounds for High-Resolution In Vivo Cancer Imaging," ChemMedChem, Jun. 2014, 9(6):1131-1135.
Miller et al., "Predicting Therapeutic Nanomedicine Efficacy Using a Companion Magnetic Resonance Imaging Nanoparticle," Sci. Transl. Med., 2015, 7(314):314ra183, 13 pages.
Miller et al., "Prediction of Anti-Cancer Nanotherapy Efficacy By Imaging," Nanotheranostics, 2017, 1(3):296-312.
Miller et al., "Radiation Therapy Primes Tumors for Nanotherapeutic Delivery via Macrophage-Mediated Vascular Bursts," Sci. Transl. Med., May 2017, 9(392):eaa10225, 12 pages.
Miller et al., "Targeting Autocrine HB-EGF Signaling With Specific ADAM12 Inhibition Using Recombinant ADAM12 Prodomain," Sci. Rep., 2015, 5:15150, 14 pages.
Miller et al., "Tumour-Associated Macrophages Act as a Slow-Release Reservoir of Nano-Therapeutic Pt(IV) Pro-Drug," Nat. Commun., 2015, 6:8692, 13 pages.
Pérez-López et al., "Gold-Triggered Uncaging Chemistry in Living Systems," Angew. Chem. Int. Ed. Engl., 2017, 56:12548-12552.
Ramanathan et al., "Correlation Between Ferumoxytol Uptake in Tumor Lesions By MRI and Response to Nanoliposomal Irinotecan in Patients With Advanced Solid Tumors: A Pilot Study," Clin. Cancer Res.,2017, 23:3638-3648, 12 pages.
Roth et al., "Dendritic, oligomeric, and polymeric self-immolative molecular amplification," Chem Rev, 2016, 116(3):1309-52, 44 pages.
Rubio-Ruiz et al., "Efficient Palladium-Triggered Release of Vorinostat From a Bioorthogonal Precursor," J Med. Chem., 2016, 59:9974-9980.
Schluep et al., "Pharmacokinetics and Tumor Dynamics of the Nanoparticle IT-101 From Pet Imaging and Tumor Histological Measurements," Proc. Natl. Acad. Sci. USA, Jul. 2009, 106(27):11394-11399.
Shi et al., "Cancer Nanomedicine: Progress, Challenges and Opportunities," Nat. Rev. Cancer, Jan. 2017, 17(1):20-37, 18 pages.
Stepanova et al., "Visualization of Microtubule Growth in Cultured Neurons Via the Use of EB3-GFP (End-Binding Protein 3-Green Fluorescent Protein)," J Neurosci., Apr. 2003, 23(7):2655-2664.
Sun et al., "Improved Tumor Uptake By Optimizing Liposome Based Res Blockade Strategy," Theranostics, 2017, 7(2):319-328.
Tu et al., "Dissociative bioorthogonal reactions," ChemBioChem, Jul. 2019, 20(13):1615-1627, 14 pages.
Versteegen et al., "Click to Release: Instantaneous Doxorubicin Elimination Upon Tetrazine Ligation," Angew. Chem. Int. Ed. Engl., Dec. 2013, 125(52):14362-14366.
Völker and Meggers, "Chemical Activation in Blood Serum and Human Cell Culture: Improved Ruthenium Complex for Catalytic Uncaging of Alloc-Protected Amines," Chembiochem, Jun. 2017, 18(12):1083-1086, 15 pages (Accepted Manuscript).
Wang et al., "A Self-immolative Prodrug Nanosystem Capable of Releasing a Drug and a NIR Reporter for In Vivo Imaging and Therapy," Biomaterials, Sep. 2017, 139:139-150.
Wang et al., "Chemical Remodeling of Cell-Surface Sialic Acids through a Palladium-Triggered Bioorthogonal Elimination Reaction," Angew. Chem. Int. Ed., 2015, 54:5364-5368.
Weiss et al., "Extracellular Palladium-Catalysed Dealkylation of 5-Fluoro-1-Propargyl-Uracil as a Bioorthogonally Activated Prodrug Approach," Nat. Commun., 2014, 5(3277): 9 pages.
Xu et al., "An Injectable Nanoparticle Generator Enhances Delivery of Cancer Therapeutics," Nat. Biotechnol., 2016, 34:414-418, 7 pages.
Yameen et al., "Insight Into Nanoparticle Cellular Uptake and Intracellular Targeting," J Control. Release, Sep. 2014, 190:485-499.
Yan et al., "Self-immolative colorimetric, fluorescent and chemiluminescent chemosensors," Chem Soc Rev, 2018, 47:6900-6916, 17 pages.
Zhang et al., "Improved Tumor Targeting and Longer Retention Time of NIR Fluorescent Probes Using Bioorthogonal Chemistry," Theranostics, Aug. 2017, 7(15):3794-3802.
Zhang et al., "Systematic Investigation on the Intracellular Trafficking Network of Polymeric Nanoparticles, " Nanoscale, 2017, 9:3269-3282, 14 pages.
Zhang et al., "The Chemotherapeutic Potential of PEG-b-PLGA Copolymer Micelles That Combine Chloroquine as Autophagy Inhibitor and Docetaxel as an Anti-Cancer Drug," Biomaterials, Nov. 2014, 35(33):9144-9154, 11 pages.
Extended European Search Report in European Appln. No. 19895604.7, dated Nov. 25, 2022, 10 pages.
Neumann et al., "Tetrazine-Responsive Self-immolative Linkers," Chembiochem, Jan. 2017, 18(1):91-95.

* cited by examiner

Alloc-SIL-$C_{16}$-MMAE
($C_{16}$proMMAE)

Alloc-SIL-$C_{16}$ - Dox
($C_{16}$proDOX)

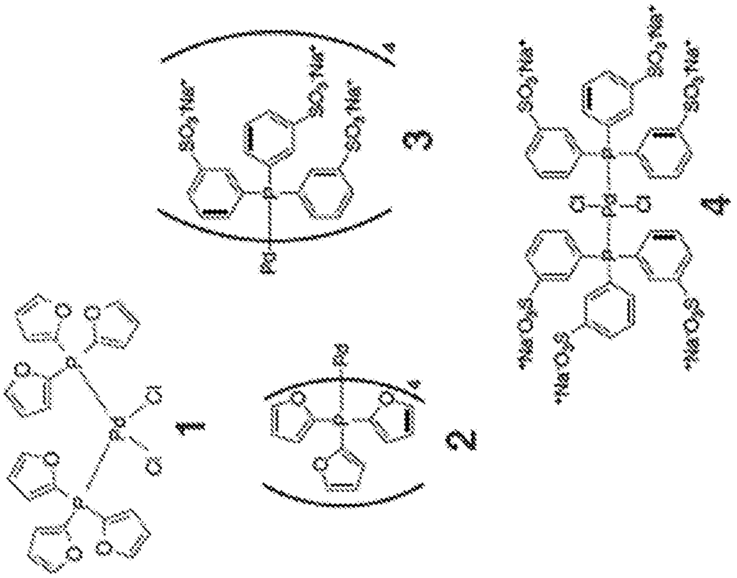
1 2 3 4
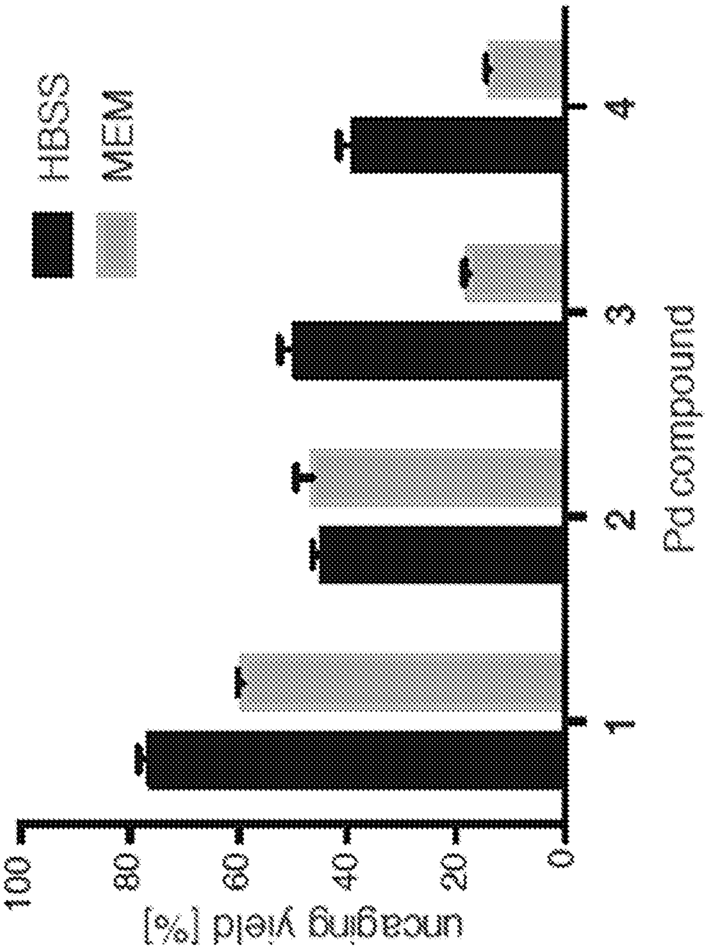
FIG. 8C

| | $C_{18}$proDOX | $C_{18}$proMMAE |
|---|---|---|
| 0 h diameter | 82.7 ± 1 nm | 90.4 ± 3 nm |
| 0 h PDI | 0.11 | 0.13 |
| 72 h diameter | 66.5 ± 0.2 nm | 70 ± 1.3 nm |
| 72 h PDI | 0.09 | 0.11 |
| zeta potential (dI $H_2O$) | -19 mV | -27 mV |
| zeta potential (PBS) | -5.3 mV | -4.2 mV |
| encapsulation efficiency | >90% | >90% |
| 72 h prodrug release | 20% ± 6% | 9% ± 1% |

FIG. 9B

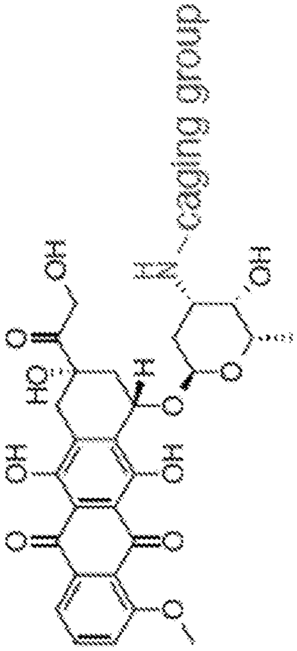
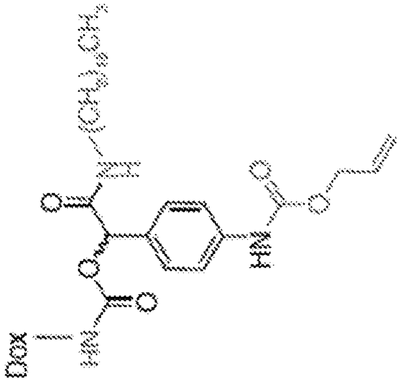
Alloc-SIL-$C_{16}$-Dox
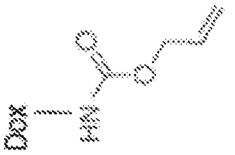
Alloc-DOX
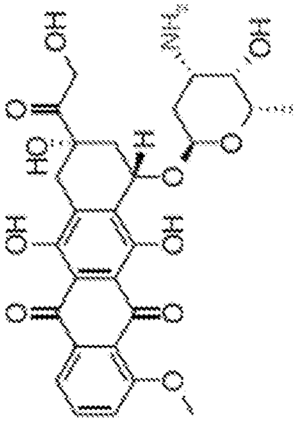
DOX
FIG. 10A

| parameter | description | optimized value | notes |
|---|---|---|---|
| $V_p$ | vascular volume | 0.7 mL | [Baxter et aL, 1994, Cancer Res, 54, 1517-28; Hendriks et al,. 2012, CPT Pharmacometrics Syst Pharmacol, 1, e15] |
| $k_{el}$ | plasma elimination | $0.01 \pm 0.003$ $min^{-1}$ | Initialized from [Baxter et al. 1994, Cancer Res, 54, 1517-28] |
| $PS_{CP}$ | plasma / heart interst. transport | $[1.2 \pm 0.4] \times 10^{-6}$ mL $min^{-1}$ | permeability * surface area |
| $V_h$ | interstitial heart volume | 0.019 mL | [Baxter et al., 1994, Cancer Res, 54, 1517-28] |
| $V_{tot\ h}$ | total heart volume | 0.133 mL | [Baxter et al., 1994, Cancer Res, 54, 1517-28] |
| $\Delta_{CLi}$ | plasma / liver convective transport | 1.1 mL $min^{-1}$ | convective transport [Baxter et al., 1994, Cancer Res, 54, 1517-28] |
| $V_{LV}$ | volume of liver vasculature | 0.095 mL | [Baxter et al., 1994, Cancer Res, 54, 1517-28] |
| $V_{tot\ L}$ | total liver volume | 0.95 mL | [Baxter et al., 1994, Cancer Res, 54, 1517-28] |
| $k_{KU}$ | $2^{nd}$-order Kupffer cell uptake | $0.016 \pm 0.008$ $(mg/mL)^{-1}$ $min^{-1}$ | initialized from in vitro NP uptake data: [Miller et al., 2017, Sci Transl Med, 9,eaal0225] |
| $P_t$ | permeability of tumor Vasc. | $3.1 \pm 1 \times 10^{-7}$ cm $min^{-1}$ | initialized from [Miller et al., 2015, Sci Transl Med, 7, 314ra183; Miller et al., 2017, Sci Transl Med, 9, eaal0225] |
| $k_{tu}$ | $2^{nd}$-order tumor cell uptake | $0.018 \pm 0.003$ $(mg/mL)^{-1}$ $min^{-1}$ | initialized from [Schluep et al., 2009, Proc Natl Acad Sci U S A, 106, 11394-9] |
| $S_t$ | vasc. surface area of tumor | 6 $cm^2$ | [Schluep et al., 2009, Proc Natl Acad Sci U S A, 106, 11394-9] |
| $NK_u$ | # Ku cells | $3.5 \times 10^7$ | [Lopez et al., 2011, Comp Hepatol, 10, 2; Baratta et al. 2009, Histochem Cell Biol, 131, 713-26] |

FIG. 16

| | | | |
|---|---|---|---|
| $UC_{Ku}$ | phagocyte uptake capacity | $[2.8 \pm 1] \times 10^{-9}$ mg $mL^{-1}$ | initialized from in vitro saturation experiments [Miller et al., 2017, Sci Transl Med, 9, eaal0225] |
| $V_{TI}$ | volume of tumor interstitum | 0.105 mL | [Schluep et al., 2009, Proc Natl Acad Sci U S A, 106, 11394-9] |
| $V_{TC}$ | volume of tumor cells | 0.113 mL | [Schluep et al., 2009, Proc Natl Acad Sci U S A, 106, 11394-9; Miller et al., 2015, Sci Transl Med, 7, 314ra183] |
| $V_{tot\ T}$ | total tumor volume | 0.3 mL | [Schluep et al., 2009, Proc Natl Acad Sci U S A, 106, 11394-9] |
| $k_{act}$ | Pd activity in cells | $0.008 \pm 0.002$ $(mg/mL)^{-1}$ $min^{-1}$ | |
| $k_{act, DC}$ | Pd activity in downstream compartment | $[2.4 \pm 5.3] \times 10^{-7}(mg/mL)^{-1}$ $min^{-1}$ | |
| $V_{Ku}$ | volume of total Ku cells | $0.096 \pm 0.01$ mL | |
| $V_{TAM}$ | volume of total TAM | 0.038 mL | [Schluep et al., 2009, Proc Natl Acad Sci U S A, 106, 11394-9; Miller et al., 2015, Sci Transl Med, 7, 314ra183] |
| NTAM | # TAM | $7.5 \times 10^6$ | [Miller et al., 2015, Sci Transl Med, 7, 314ra183: Miller et al., 2017, Sci Transl Med, 9 eaal0225] |
| $UC_{TAM}$ | TAM uptake capacity | $[3.5 \pm 4] \times 10^{-9}$ mg $mL^{-1}$ | initialized from in vitro saturation experiments [Miller et al., 2017, Sci Transl Med, 9, eaal0225] |
| $k_{iTAM}$ | $2^{nd}$-order TAM uptake | $0.08 \pm 0.05$ $(mg/mL)^{-1}$ $min^{-1}$ | |
| $k_{pTAM}$ | $2^{nd}$-order TAM uptake | $0.016 \pm 0.07$ $(mg/mL)^{-1}$ $min^{-1}$ | |
| $k_{Turn}$ | turnover of phagocyte uptake capacity | $[4.5 \pm 1.6] \times 10^{-3}$ $min^{-1}$ | initialized from in vivo saturation: [Miller et al., 2017, Nat Commun, 8, 15906: Sun et al. 2017, Theranostics, 7, 319-328] |
| $k_{qcat}$, $k_{qpro}$ | NP i.v. infusion rates | bolus (see methods) | |

FIG. 16 (Cont.)

| | | |
|---|---|---|
| catalytic NP | $y_1$ : cat NP in plasma | $dy_1/dt = Kqcxt / V_P - k_{ku} y_1 + [PS_{CP} (y_2 - y_1) + \Delta CU(y_3 - y_1) + P_tS_t (y_7 - y_1) - K_{PTAM} y_1 y_8 V_n] V_P^{-1}$ |
| | $y_2$ : cat NP in intst. heart | $dy_2/dt = -PS_{CP} (y_2 - y_1) V_h^{-1}$ |
| | $y_3$ : cat NP in liver vessel | $dy_3/dt = -\Delta CU(y_3 - y_1) V_{LV}^{-1} - KXu\ y_3 y_4$ |
| | | |
| | $y_5$ : cat NP in Ku cell | $dy_5/dt = KXu\ y_3 y_4 V_{LV} / V_{Ku} - K_{Tum} y_5$ |
| | $y_6$ : cat NP in ku sink | $dy_6/dt = K_{Tum} y_5$ |
| | | |
| | $y_7$ : cat NP in tumor intst | $dy_7/dt = P_tS_t (y_1 - y_7) V_n^{-1} - K_{Tu} y_7 - K_{pTAM} y_7 y_8$ |
| | $y_8$ : cat NP in tumor cells | $dy_8/dt = K_{Tu} y_7 V_n V_{rc}^{-1}$ |
| | | |
| | $y_{10}$ : cat NP in TAM | $dy_{10}/dt = K_{TAM} y_7 y_9 V_n V_{TAM}^{-1} - K_{TAM} y_{10} + K_{pTAM} y_1 y_9 V_n V_{TAM}^{-1}$ |
| | $y_{11}$ : cat NP in TAM sink | $dy_{11}/dt = K_{Tum} y_{10}$ |
| available sites for NP uptake | | |
| | $y_4$ : Ku uptake capacity | $dy_4/dt = K_{Tum} (y_5 + y_{5-2} + y_{5-3}) V_{ku} V_{LV}^{-1} - K_{ku} (y_{3-2} y_4 + y_3 y_4)$ |
| | $y_9$ : TAM uptake capacity | $dy_9/dt = K_{Tum} (y_{10} + y_{10-2} + y_{10-3}) V_{TAM} V_n^{-1} - K_{TAM} (y_7 + y_{7-2}) y_9 - K_{pTAM} (y_1 + y_{1-2}) y_9$ |
| | | |
| prodrug NP | $y_{1-2}$ : prodrug NP in plasma | $dy_{1-2}/dt = K_{q2} / V_p - k_{ku} y_{1-2} + [ PS_{CP} (y_{2-2} - y_{1-2}) + \Delta CU(y_{3-2} - y_{1-2}) + P_tS_t (y_{7-2} - y_{1-2}) - K_{pTAM} y_{1-2} - y_9 V_n] V_P^{-1}$ |
| | $y_{2-2}$ : prodrug NP in intst. heart | $dy_{2-2}/dt = PS_{CP} (y_{2-2} - y_{1-2}) V_h^{-1}$ |
| | $y_{3-2}$ : prodrug NP in liver vessel | $dy_{3-2}/dt = \Delta CU(y_{3-2} - y_{1-2}) V_{LV}^{-1} - K_{ku} y_{3-2} y_4$ |
| | | |
| | $y_{5-2}$ : prodrug NP in ku cell | $dy_{5-2}/dt = k_{ku} y_{3-2} y_4 V_{LV} / V_{kv} - K_{tum} y_{5-2} - K_{act} y_5 y_{5-2}$ |
| | $y_{6-2}$ : prodrug NP in ku sink | $dy_{6-2}/dt = K_{tum} y_{6-2} - K_{actDC} y_6 y_{6-2}$ |

FIG. 17

| | | |
|---|---|---|
| | $y_{7\text{-}2}$ : prodrug NP in tumor intst | $dy_{7\text{-}2}/dt = P_tS_t\,(y_{1\text{-}2} - y_{7\text{-}2})\,V_n^{-1} - K_{Tu}\,y_{7\text{-}2} - K_{pTAM}\,y_{7\text{-}2}\,y_9$ |
| | $y_{8\text{-}2}$ : prodrug NP in tumor cells | $dy_{8\text{-}2}/dt = K_{Tu}\,y_{7\text{-}2}\,V_n\,V_{rc}^{-1} - K_{act}\,y_8\,y_{8\text{-}2}$ |
| | | |
| | $y_{10\text{-}2}$ : prodrug NP in TAM | $dy_{10\text{-}2}/dt = K_{TAM}\,y_{7\text{-}2}\,y_9\,V_n\,V_{TAM}^{-1} - K_{tum}\,y_{10\text{-}2} - K_{act}\,y_{10}\,y_{10\text{-}2} + K_{pTAM}\,y_{1\text{-}2}\,y_9\,V_n\,V_{TAM}^{-1}$ |
| | $y_{11\text{-}2}$ : prodrug NP in TAM sink | $dy_{11\text{-}2}/dt = K_{Tum}\,y_{10\text{-}2} - K_{actDC}\,y_{11}\,y_{11\text{-}2}$ |
| depleted prodrug NP | | |
| | $y_{5\text{-}3}$ : depL prodrug NP in Ku cell | $dy_{5\text{-}3}/dt = K_{act}\,y_5\,y_{5\text{-}2} - K_{Tum}\,y_{5\text{-}3}$ |
| | $y_{6\text{-}3}$ : depL prodrug NP in Ku sink | $dy_{6\text{-}3}/dt = K_{actDC}\,y_6\;\,y_{6\text{-}2} + K_{Tum}\,y_{5\text{-}3}$ |
| | | |
| | $y_{8\text{-}3}$ : depL prodrug NP in tu cell | $dy_{8\text{-}3}/dt = K_{act}\,y_8\,y_{8\text{-}2}$ |
| | | |
| | $y_{10\text{-}3}$ : depL prodrug NP in TAM | $dy_{10\text{-}3}/dt = K_{act}\,y_{10}\,y_{10\text{-}2} - K_{tum}\,y_{10\text{-}3}$ |
| | $y_{11\text{-}3}$ : depL prodrug NP in TAM sink | $dy_{11\text{-}3}/dt = K_{actDC}\,y_{11}\,y_{11\text{-}2} + K_{tum}\,y_{10\text{-}3}$ |
| activacted drug | | |
| | $y_{5\text{-}4}$ : act drug in ku cell | $dy_{5\text{-}4}/dt = K_{act}\,y_5\,y_{5\text{-}2}$ |
| | $y_{6\text{-}4}$ : act drug in ku sink | $dy_{6\text{-}2}/dt = K_{actDC}\,y_6\,y_{6\text{-}2}$ |
| | | |
| | $y_{8\text{-}4}$ : act drug in tumor cell | $dy_{8\text{-}4}/dt = K_{act}\,y_8\,y_{8\text{-}2}$ |
| | | |
| | $y_{10\text{-}4}$ : act drug in TAM | $dy_{10\text{-}4}/dt = K_{act}\,y_{10}\,y_{10\text{-}2}$ |
| | $y_{11\text{-}4}$ : act drug in TAM sink | $dy_{11\text{-}4}/dt = K_{actDC}\,y_{11}\,y_{11\text{-}2}$ |

FIG. 17 (Cont.)

| parameter | description | objective value | notes |
|---|---|---|---|
| $t_{1/2,\ cat\ NP}$ | circulation half-life, catalystic NP | 56 min | time-lapse intravital microscopy of comparable PLGA-PEG NPs in same mouse model [Miller et al., 2017, Sci Transl Med, 9, eaal0225] |
| $t_{1/2,\ prodrug\ NP}$ | circulation half-life, prodrug NP | 120 min | time-lapse intravital microscopy of comparable PLGA-PEG NPs in same mouse model, following PdNP [Miller et al., 2017, Nat Commun, 8, 15906] |
| $t_{1/2,\ ratio}$ | ratio of half-life, cat NP : prodrug NP | 0.52 ± 0.05 | derived from intravital imaging data in same system (see above); averaged with time-lapse biodistribution data from similar "loading dose" studies [Sun et al., 2017, Theranostics, 7, 319-328; Jang et al., 2016, Biomed Pharmacother, 80, 162-172] |
| liver uptake | % I.D. / g total liver tissue, catalytic Np | 6 ± 3 % ID/g | averaged from a composite of PdNP AAS [Miller et al., 2017, Nal Commun, 8, 15906] and 3 other PLGA-PEG based NPs [Miller et al., 2017, Sci Transl Med, 9, eaal0225; [Hrkach et al., 2012, Sci Transl Med, 4, 128ra39] |
| liver ratio | ratio of liver uptake, cat NP : prodrug NP | 1.75 ± 0.3 | derived from AAS and fluorescence reflectance imaging of biodistribution in same model [Miller et al., 2017, Nat Commun, 8, 15906] averaged with biodistribution data from similar "loading dose" studies [Sun et al., 2017, Theranostics, 7, 319-328; Jang et al., 2016, Biomed Pharmacother, 80, 162-172; Liu et al., 2013, Biochim Biophys Acta, 1830, 3447-53; Liu et al., 2015, Sci Rep, 5, 10881] |
| tumor uptake | % I.D. / g tumor tissue, catalytic Np | 0.7 % ID/g | [Miller et al., 2017, Nat Commun, 8, 15906] and consistent with similar PLGA-PEG NPs in the same tumor model [Miller et al., 2017, Sci Transl Med, 9, eaal0225; [Miller et al., 2015, Sci Transl Med, 7, 314ra183; [Miller et al., 2015, Nat Commun, 6, 8692] |

FIG. 18

| | | | |
|---|---|---|---|
| tumor ratio | ratio of tumor uptake, cat NP : prodrug NP | 0.56 ± 0.07 | averaged with biodistribution data from similar "loading dose" studies [Sun et al., 2017, Theranostics, 7, 319-328; Jang et al., 2016, Biomed Pharmacother, 80, 162-172; Liu et al., 2013, Biochim Biophys Acta, 1830, 3447-53; Liu et al., 2015, Sci Rep, 5, 10881] |
| fraction tumor activation | ratio of prodrug that activated in the tumor | 0.5 | [Miller et al., 2017, Nat Commun, 8, 15906] |
| fraction liver activation | ratio of prodrug that activated in the liver | 0.25 | [Miller et al., 2017, Nat Commun, 8, 15906] |
| heart uptake | % I.D. / g tumor tissue, catalytic Np | 0.11 | [Miller et al., 2017, Nat Commun, 8, 15906] |
| ratio tumor: TAM uptake | ratio of catalytic NP uptake in tumor cells compared to TAM (integrated across all cells) | 0.7 | intravital microscopy and flow-cytometry using same tumor model and multiple similar PLGA-PEG NPs [Miller et al., 2017, Nat Commun, 8, 15906; [Miller et al., 2017, Sci Transl Med, 9, eaal0225; [Miller et al., 2015, Sci Transl Med, 7, 314ra183; [Miller et al., 2015, Nat Commun, 6, 8692] |
| ratio tumor: uptake with 5 Gy RT | ratio of catalytic NP accumulating in HT1080 tumors, either with or without 5 Gy irradiation 3 days prior | 1.7 | intravital microscopy and flow-cytometry using same tumor model and multiple similar PLGA-PEG NPs [Miller et al., 2017, Sci Transl Med, 9, eaal0225] |

FIG. 18 (Cont.)

| treatment | tumor growth inh.? | tumor shrinkage? | systemic toxicity? | dose (mg/kg) | $IC_{50}$ (nM) | |
|---|---|---|---|---|---|---|
| Pd-NP | - | - | - | 50 | 70,000 | *see [Miller et al., 2017, Nat Commun, 8, 15906] |
| $C_{16}$proMMAE-NP | - | - | - | 1 | 3,000 | |
| solvent MMAE | n/a | n/a | + | 1 | 0.04 | *see [Legigan et al., 2012, Angew Chem Int EdEngl, 51, 11606-10] |
| MMAE-NP | n/a | n/a | n/a | n/a | n/a | |
| RT | + | - | - | 5 Gy | * | *see [Miller et al., 2017, Transl med, 9, eaal0225] |
| $C_{16}$proMMAE-Pd | + | - | - | 1 | 0.02 | |
| $C_{16}$proMMAE-Pd+RT | + | + | - | 1 | | |
| solvent DOX | ++ | - | ++ | 10 | 100 | |
| DOX-NP | | - | + | 10 | 200 | |
| Alloc-proDOX-NP | - | - | - | 10 | 10,000 | *see [Miller et al., 2017, Nat Commun, 8, 15906] |
| Pd+Alloc-proDOX-NP | +/- | - | - | 10 | 20 | |
| Pd+Alloc-proDOX-NP | + | - | - | 30 | 20 | |

FIG. 19

AMC

6

7

Alloc-SIL-$dPEG_4$-AMC (8)

8

9

10

11

Alloc-SIL-$C_{16}$-Dox

12

13

Alloc-SIL-$C_{16}$-MMAE

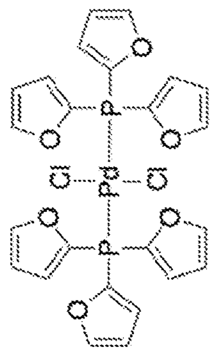
Pd-1
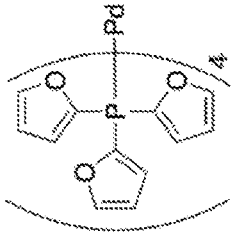
Pd-2
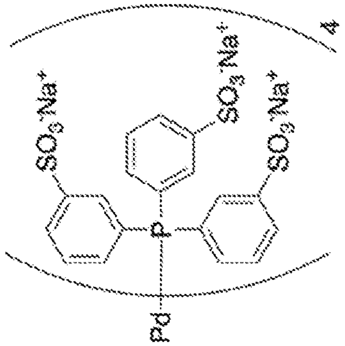
Pd-3
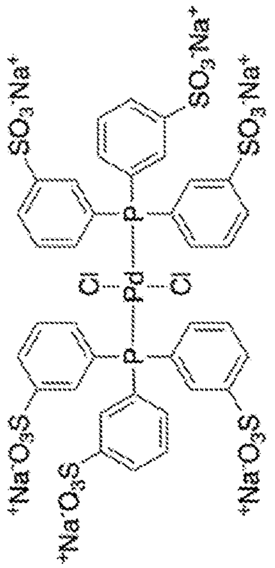
Pd-4
FIG. 26

PRODRUGS WITH A TRIDENTATE SELF-IMMOLATIVE LINKER

CLAIM OF PRIORITY

This application is a § 371 National Stage Application of PCT/US2019/066101, filed Dec. 12, 2019, which claims priority to U.S. Patent Application Ser. No. 62/778,837, filed on Dec. 12, 2018, the entire contents of which are hereby incorporated by reference.

FEDERALLY SPONSORED RESEARCH OR DEVELOPMENT

This invention was made with government support under Grant Nos. CA207744, CA206890, CA206997, and CA079443 awarded by the National Institutes of Health. The government has certain rights in the invention.

TECHNICAL FIELD

This invention relates to prodrug compounds, and in particular to prodrug compounds including a tridentate self-immolative linker useful in treating various conditions such as cancer.

BACKGROUND

Cancer is one of the leading causes of death in contemporary society. The numbers of new cancer cases and deaths is increasing each year. Currently, cancer incidence is 454.8 cases of cancer per 100,000 men and women per year, while cancer mortality is 71.2 cancer deaths per 100,000 men and women per year. Pharmacological interventions that are safe over the long term may improve cancer treatment and decrease cancer mortality.

SUMMARY

Prodrug strategies that facilitate localized and controlled activity of therapeutics (e.g., small molecule therapeutics) can reduce systemic exposure and improve pharmacokinetics, yet limitations in activation chemistry have made it difficult to assign tunable multifunctionality to prodrugs. The present application describes the design and application of a modular small-molecule caging strategy that couples bioorthogonal cleavage with a self-immolative linker and an aliphatic anchor. This is achieved by in vivo catalysis by, e.g., a nano-encapsulated palladium compound (Pd-NP), which mediates cleavage (e.g., allylcarbamate cleavage) and triggers release of the activated drug. The aliphatic anchor enables >90% nano-encapsulation efficiency of the prodrug, while also allowing >104 fold-increased cytotoxicity upon prodrug activation. The results described herein show the application of the prodrugs within the present claims to a formulation of monomethyl auristatin E (MMAE), demonstrating its ability to target microtubules and kill cancer cells only after selective activation by Pd-NP. Computational pharmacokinetic modeling provides a mechanistic basis for the observation that the nanotherapeutic prodrug strategy can lead to more selective activation in the tumor, yet in a manner that is more sensitive to variable enhanced permeability and retention (EPR) effects. The experimental results show that the combination treatment with the nano-encapsulated MMAE prodrug and Pd-NP safely blocks tumor growth. The combination treatment can be combined with a local radiation therapy regimen that is known to improve EPR effects.

In some embodiments, the present disclosure provides a compound of Formula (I):

(I)

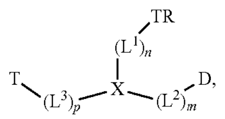

or a pharmaceutically acceptable salt thereof, wherein:

X is a tridentate self-immolative linker;

each $L^1$ is independently selected from $N(R^N)$, O, C(=O), S, S(=O), $S(=O)_2$, $C_{1-6}$ alkylene, $C_{3-7}$ cycloalkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$, n is an integer from 0 to 10;

each $L^2$ is independently selected from $N(R^N)$, O, C(=O), S, S(=O), $S(=O)_2$, $C_{1-6}$ alkylene, $C_{3-7}$ cycloalkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$, m is an integer from 0 to 10;

each $L^3$ is independently selected from $N(R^N)$, O, C(=O), S, S(=O), $S(=O)_2$, $C_{1-6}$ alkylene, $C_{3-7}$ cycloalkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$, p is an integer from 0 to 10;

each x is independently an integer from 1 to 2,000;

each $R^N$ is independently selected from H, $C_{1-3}$ alkyl, and $C_{1-3}$ haloalkyl;

T is a ligand moiety;

TR is a trigger-sensitive moiety; and

D is a drug moiety.

In some embodiments, n is an integer from 0 to 5, and each $L^1$ is selected from NH, O, C(=O), $C_{1-6}$ alkylene, and $C_{6-10}$ arylene.

In some embodiments, m is an integer from 0 to 5, and each $L^2$ is independently selected from NH, O, C(=O), $C_{1-6}$ alkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$.

In some embodiments, p is an integer from 0 to 7, and each $L^3$ is independently selected from NH, O, C(=O), $C_{1-6}$ alkylene, $C_{6-10}$ arylene, and $-(OCH_2CH_2)_x-$.

In some embodiments, x is an integer from 2 to 10.

In some embodiments:

n is an integer from 0 to 5, and each $L^1$ is selected from NH, O, C(=O), $C_{1-6}$ alkylene, and $C_{6-10}$ arylene;

m is an integer from 0 to 5, and each $L^2$ is independently selected from NH, O, C(=O), $C_{1-6}$ alkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$;

p is an integer from 0 to 7, and each $L^3$ is independently selected from NH, O, C(=O), $C_{1-6}$ alkylene, $C_{6-10}$ arylene, and $-(OCH_2CH_2)_x-$; and x is an integer from 2 to 10.

In some embodiments, the self-immolative linker X is a p-amino mandelic acid derivative.

In some embodiments, the compound of Formula (I) has formula:

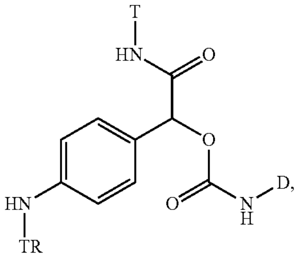

or a pharmaceutically acceptable salt thereof.

In some embodiments, the ligand group T is an anchoring moiety or a solubilization moiety.

In some embodiments, the solubilization moiety is a hydrophilic polymer selected from polyethylene glycol (PEG), polypropylene glycol (PPG).

In some embodiments, the anchoring moiety is a lipophilic moiety selected from $C_{8-22}$ alkyl chain, fatty acid, fatty monoglyceride, fatty diglyceride, and a phospholipid.

In some embodiments, the trigger-sensitive moiety is a group that upon contact with a trigger reagent cleaves the bond between X and $L^1$, or X and TR if n is 0, thereby triggering a self-immolative cleavage of the linker X and the release of the drug D.

In some embodiments, the trigger sensitive moiety is selected from alloc group, poc group, enzyme-labile ester group, S—S bridge, acid-labile silyl ether, Val-Ala, Val-Cit, galactose, and a bioorthogonal click reagent.

In some embodiments, the bioorthogonal click reagent is 3-OH TCO.

In some embodiments, the drug D is selected from anti-cancer agent, anti-angiogenesis agent, anti-inflammatory agent, steroid drug, antibiotic, antiviral, anti-thrombotic, antifungal, or a pharmaceutically acceptable salt thereof.

In some embodiments, the drug D is an anti-cancer agent.

In some embodiments, the anti-cancer agent is selected from monomethyl auristatin E (MMAE) and doxorubicin.

In some embodiments, the compound of Formula (I) is selected from any one of the compounds depicted in FIGS. 2A, 2B, 8A, 10A, 21, and 22, or a pharmaceutically acceptable salt thereof.

In some embodiments, the present application provides a particle comprising a compound of Formula (I), or a pharmaceutically acceptable salt thereof, as disclosed herein.

In some embodiments, the particle comprises a hydrophobic core comprising the compound of Formula (I), or a pharmaceutically acceptable salt thereof.

In some embodiments, the particle comprises a hydrophilic shell.

In some embodiments, the particle is a nanoparticle and the nanoparticle comprises an amphiphilic polymer selected from poly(ethylene glycol)-co-poly(D,L-lactic acid) (PLA-PEG) and poly(ethylene glycol)-co-(poly(lactide-co-glycolide)) (PLGA-PEG).

In some embodiments, the present disclosure provides a method of treating a disease or condition in a subject, the method comprising administering to the subject in need thereof a compound of Formula (I), or a pharmaceutically acceptable salt thereof, as disclosed herein, or a particle comprising same, wherein the disease or condition is treatable by the drug D as provided in Formula (I).

In some embodiments, the drug D is an anticancer agent and the disease is cancer.

In some embodiments, the method comprises administering to the subject a trigger reagent.

In some embodiments, the trigger reagent comprises a transition metal, a glutathione, a protease, a peptidase, an acid, or a bioorthogonal click reagent.

In some embodiments, the bioorthogonal click reagent comprises tetrazine moiety.

In some embodiments, the trigger reagent comprises a targeting moiety that directs the delivery of the trigger reagent to the cell or tissue of the subject where treatment of the disease or condition is desired.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

b) Following 30 min pre-treatment with the indicated compounds, HT1080 cells were treated with the same NP as in a, and imaged 3 h later (n>6 biological replicates; mean±s.e.m.). c-d) HT1080 tumor cells were treated with C16proDOX, DOX, or Pd-NP with C16proDOX for 24 h, and then imaged by fluorescence microscopy (representative images shown in c) to evaluate subcellular drug accumulation based on endogenous anthracycline fluorescence (scale bar, 20 μm). Yellow lines (c) denote representative examples of how fluorescence intensity profiles were quantified from line-scans through cells (d), shown as means (thick line) ±s.e.m. (shading; n>10), for hoechstand anthracycline fluorescence.

FIGS. 4A-4F. Caged MMAE only disrupts microtubule dynamics in the presence of Pd-NP in live cancer cells. a-c) Cytotoxic drug effects were quantified by a resazurin-based cell viability assay, 72 h post-treatment. A representative dose-response curve using the ES2 cell line and MMAE illustrate Emax and $IC_{50}$ calculations (a; n=2, mean±s.e.m.), which were then compared across multiple cell lines and between treatments with MMAE vs. the combination of 50 μM Pd-NP and C16proMMAE (b-c; two-tailed t-test). See FIG. 13 for full data. d) HT1080 cells transgenically expressing EB3-mApple were confocally imaged over time to monitor the dynamics of microtubule plus-end tips in live cells (left). EB3 microtubule "comets" were automatically detected and computationally tracked (center; pseudo-colored according to comet speed) following drug treatment. Scale bar, 20 μm. See FIG. 20 for representative conditions. e-f) Neither the average number of tracks detected (e) nor the speed of those tracks moving in cells (f) substantially changed with either 1 μM C16proMMAE or 35 μM Pd-NP treatment alone, but both treatments together eliminated all EB3 comets in a manner similar to the parent uncaged drug (median±i.q.r.; 24 h treatment)

FIGS. 5A-5D. Dual Pd-NP and C16proMMAE treatment safely blocks tumor growth in multiple tumor models. a-b) HT1080 (a) and MC38 (b) tumors were treated with Pd-NP, C16proMMAE, or the combination of the two at the indicated time points (red arrows) following tumor formation. Tumor volumes were monitored over time by caliper (n>6, means±s.e.m.). c-d) Changes in individual HT1080 (c) and MC38 (d) tumor volumes were quantified and compared at day 7 (see a; n≥6, means±s.e.m; two-tailed Mann-Whitney test). e-f) Body weight was monitored in animals bearing HT1080 (e) or MC38 (f) tumors following treatment with the combination of Pd-NP and C16proMMAE, showing no significant loss compared to the vehicle control group (n≥4, means±s.e.m.). g) At the end of the study endpoint, plasma of MC38 tumor-bearing mice was analyzed for signs of toxicity, and no significant changes were observed (n≥4, means±s.e.m.; two-tailed t-test at $\alpha$=0.05 significance level).

Figure 14A:
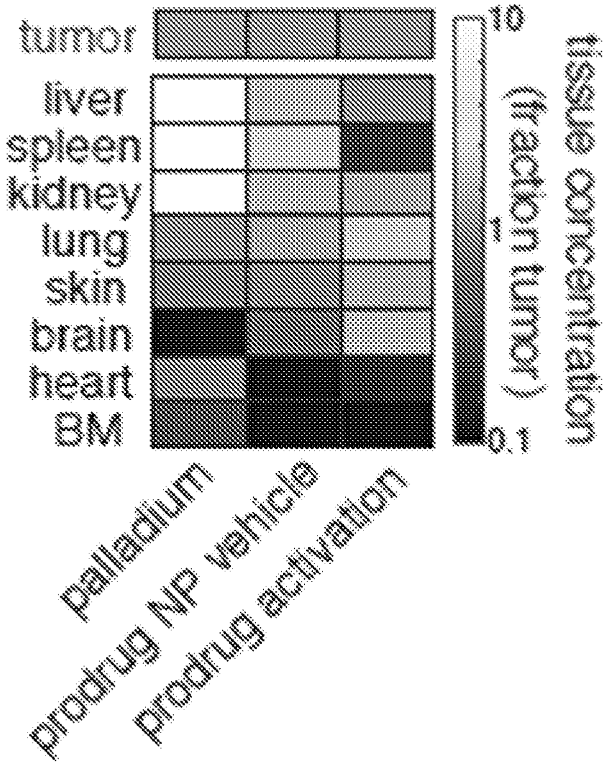

FIGS. 6A-6G. A multi-compartment pharmacokinetic model accurately reflects the benefits of the prodrug strategy. a) Schematic depicting the computational pharmacokinetic model, with particle colors corresponding to the legend at right (FIGS. 16-17 contain full equations and parameters). b) Average fit of the computational model according to objective pharmacokinetic and biodistribution parameters that were experimentally measured (see FIG. 18). c) Model simulation showing biodistribution of the catalyst, the prodrug (administered 5 h after the catalyst), and the activated prodrug over 48 h. Thick line and shading denote mean and std. dev. of simulations across n=24 optimizations. d) From data in c, the modeled ratio of tumor:liver accumulation (n=24) was compared to the experimentally observed ratio of tumor:clearance organs (liver, spleen, kidney; see FIG. 14A for details; n=3). Data are means±s.e.m. (*paired two-tailed t-tests).

FIGS. 7A-7E. Single low-dose irradiation enhances delivery and efficacy of dual Pd-NP and C16proMMAE treatment. a) Based on published experimental data (see FIG. 18), computational modeling predicts how local 5 Gy irradiation, performed 72 h prior to NP injection, impacts tumoral NP accumulation and prodrug activation (n=24 optimizations; means±s.e.m.). b-c) HT1080 tumor cells and the accumulation of PLGA-PEG NP were compared with or without irradiation as modeled in a, shown by confocal fluorescence microscopy in live tumors (b; n≥3, scale bar 100 μm), and flow cytometry of excised and digested tumors (c; n≥4), 24 h post-treatment with NP. d-e) HT1080 tumor xenografts were treated as in FIG. 6A, but with addition of a single-dose of 5 Gy irradiation locally to the tumor site (un-irradiated groups are re-shown for reference; n≥5, means±s.e.m). Corresponding changes in the volumes of individual tumors were quantified at day 7 (n≥5, means±s.e.m; two-tailed t-tests).

FIGS. 8A-8D. A model fluorogenic uncaging reaction reveals the kinetics and efficiency of Pd-mediated deprotection. a) Overview schematic of a fluorogenic substrate based on the modular prodrug design. PEG4 is used to solubilize the substrate in the absence of nano-encapsulation for the in vitro screen. In place of the caged drug payload, a caged coumarin is used as a fluorogenic readout of Pd-mediated self-immolation. b) Fluorescence excitation and emission spectra show enhanced fluorescence of Alloc-SIL-PEG4-AMC upon incubation with Pd compound (Pd-1, PdCl2 (TFP)2) approaching that of pure, uncaged AMC. c) 4 different Pd compounds (10 μM) were tested for their ability to uncage the coumarin substrate (5 μM) in physiologically relevant media (MEM and HBSS) over the course of 10 h. d) Using the top performing Pd compound (Pd-1, PdCl2 (TFP)2) the kinetics of the coumarin substrate uncaging were compared to the gold-standard reaction of uncaging bis-alloc-protected rhodamine 110 (Alloc2R110).

Figure 9A:
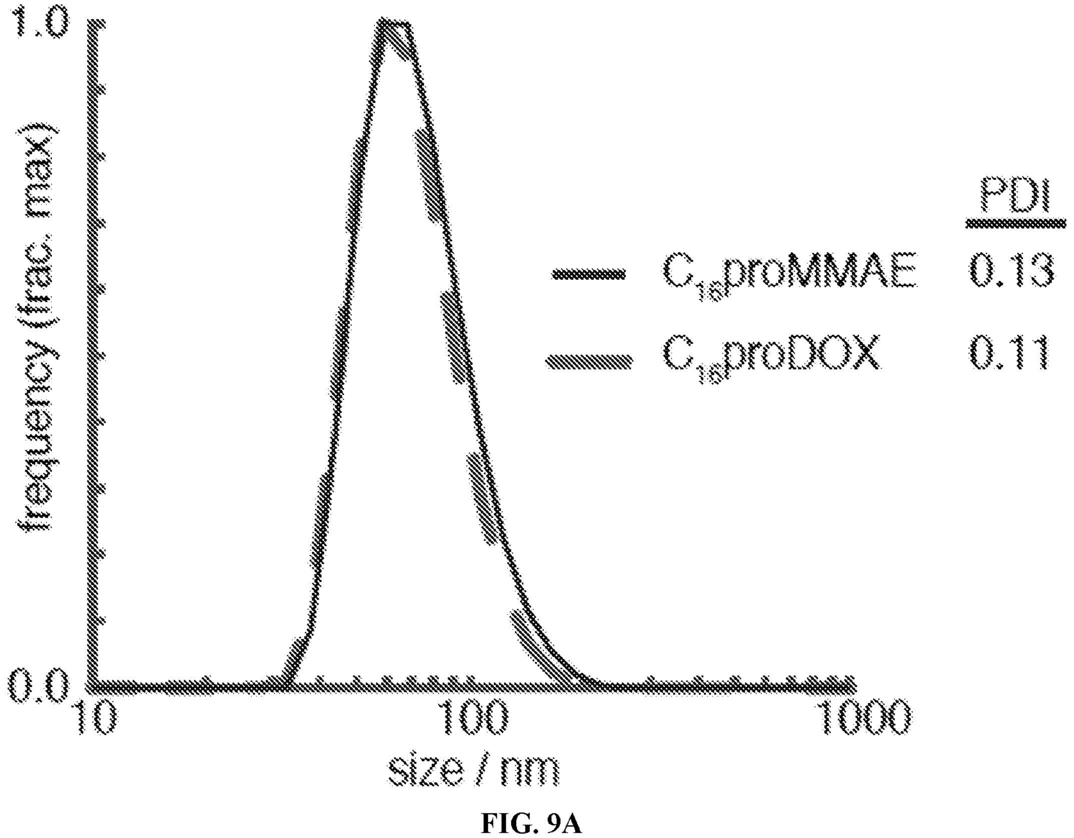

FIGS. 9A-9B. Nanoformulated prodrug size distribution and stability. a) Dynamic light scattering (DLS) describes the distribution in diameter of C16proMMAE and C16proDOX nanoformulations, along with the corresponding polydispersity indices (PDIs); mean of n=3 replicates shown. b) Mean prodrug NP diameter and PDI were measured by DLS before and after 72 h incubation in PBS at 37° C. (n=3).

Figure 10B:
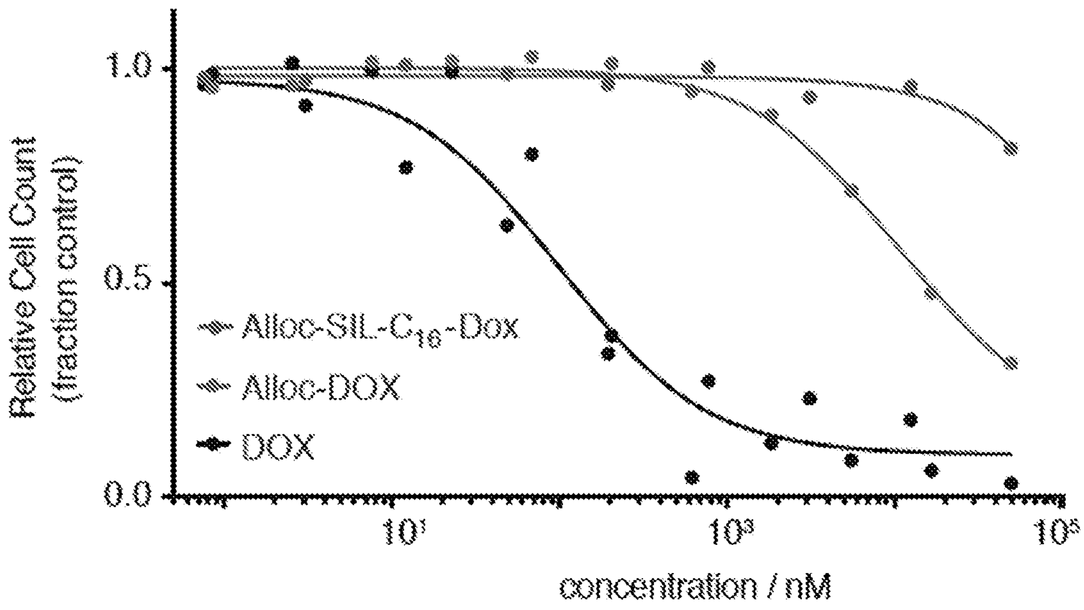
Figure 10C:
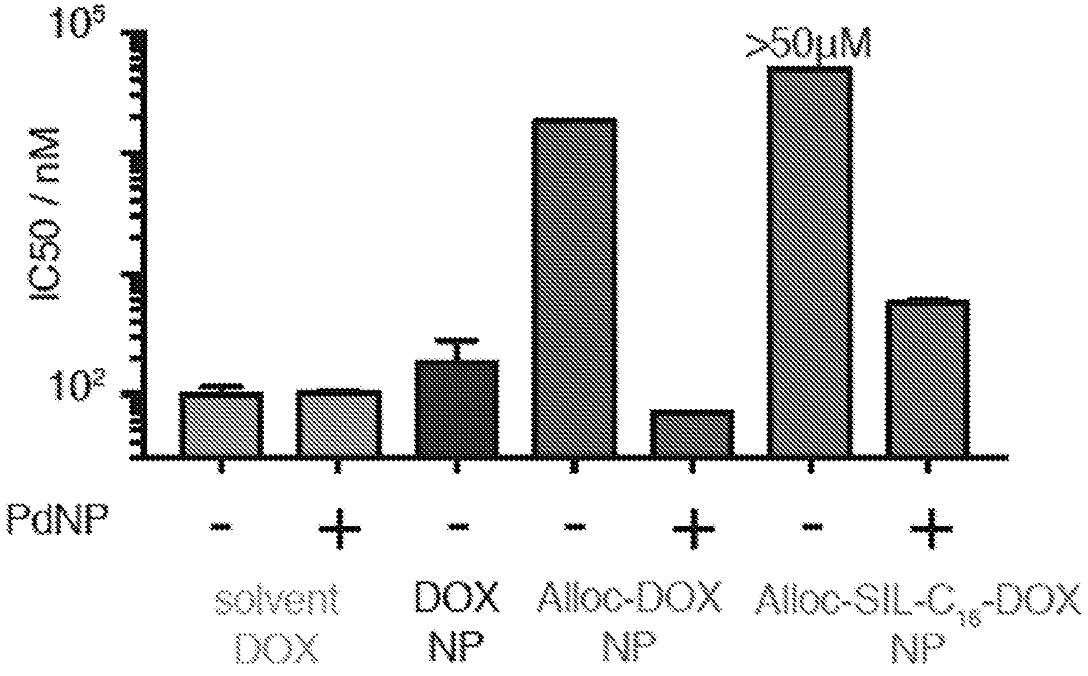

FIGS. 10A-10C. Improved prodrug caging increases maximum nontoxic dose in cells. a) Chemical structures of parent doxorubicin and the prodrug caged with Alloc- or Alloc-SIL-C16 groups. b-c) Viability of HT1080 fibrosarcoma cells was measured following 72 h treatment with doxorubicin and its caged counterparts, shown as a dose-response (b) and quantified (c) according to the concentration yielding 50% reduced viability ($IC_{50}$), in the presence or absence of 50 μM Pd-NP (n=2, means±s.e.m.).

Figure 11A:
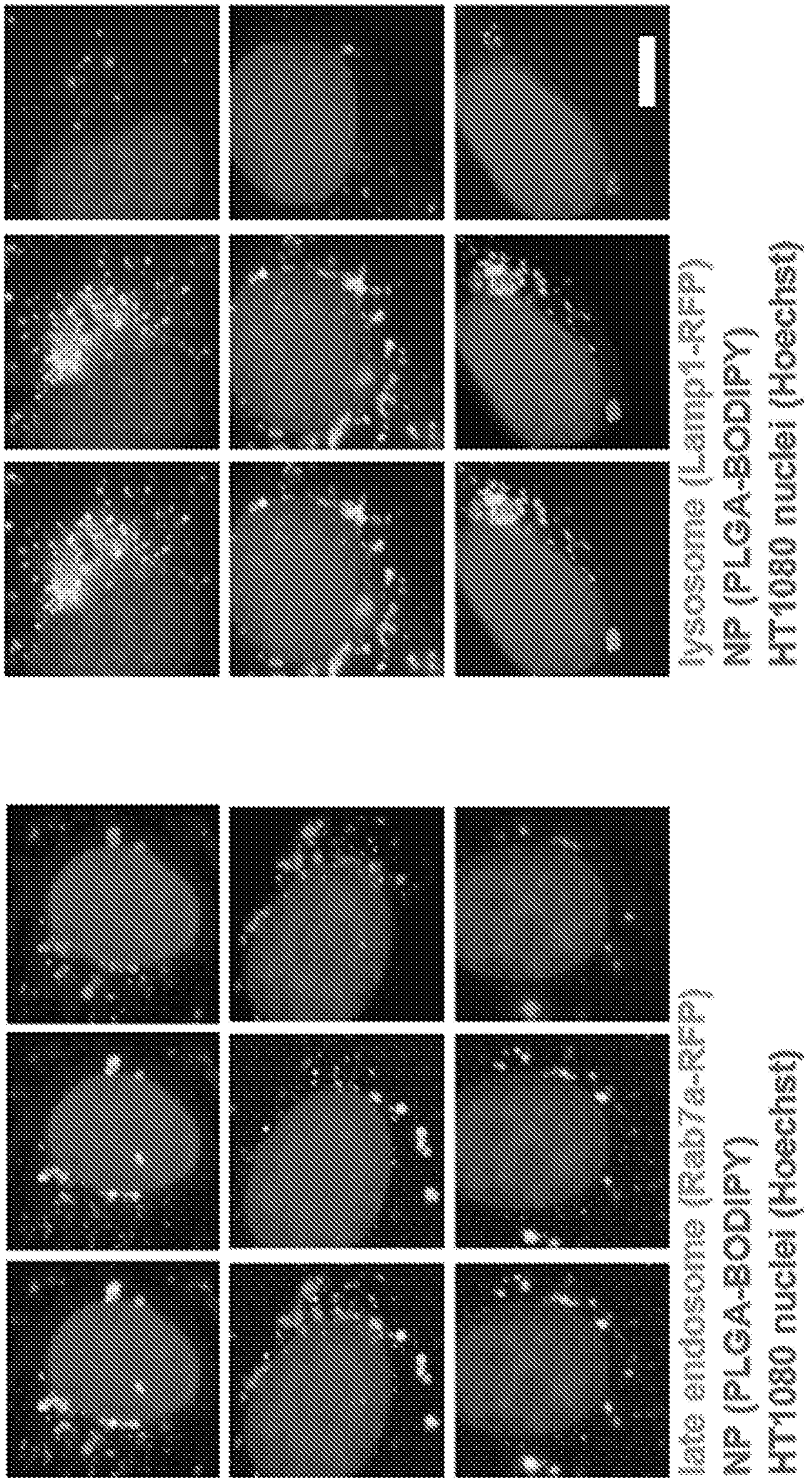
Figure 11B:
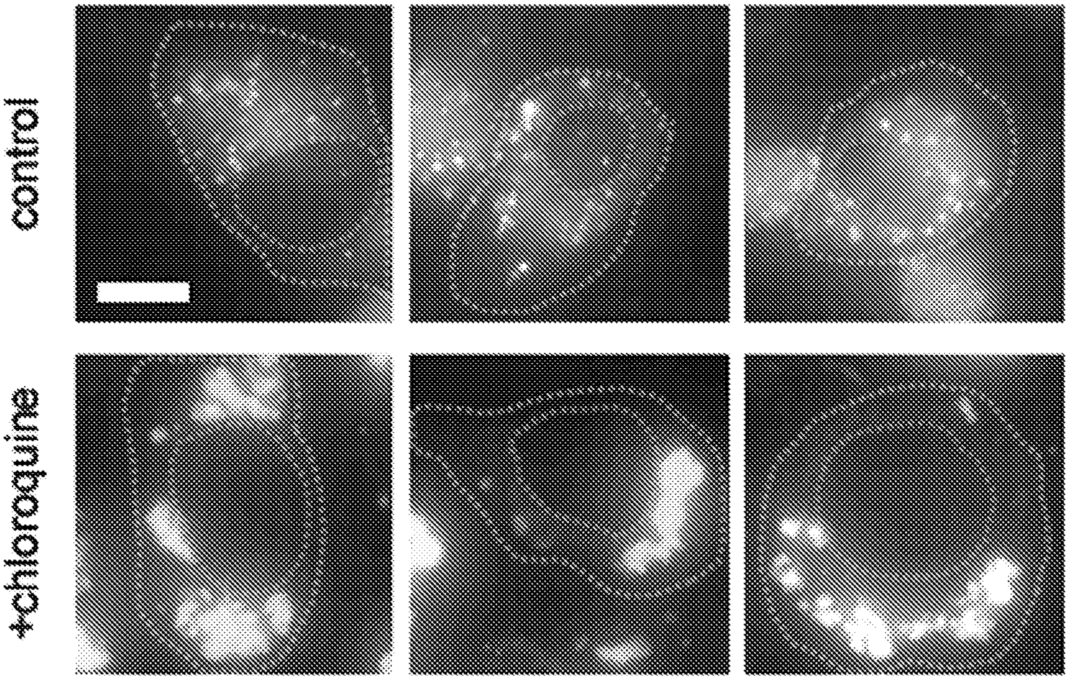
Figure 11C:
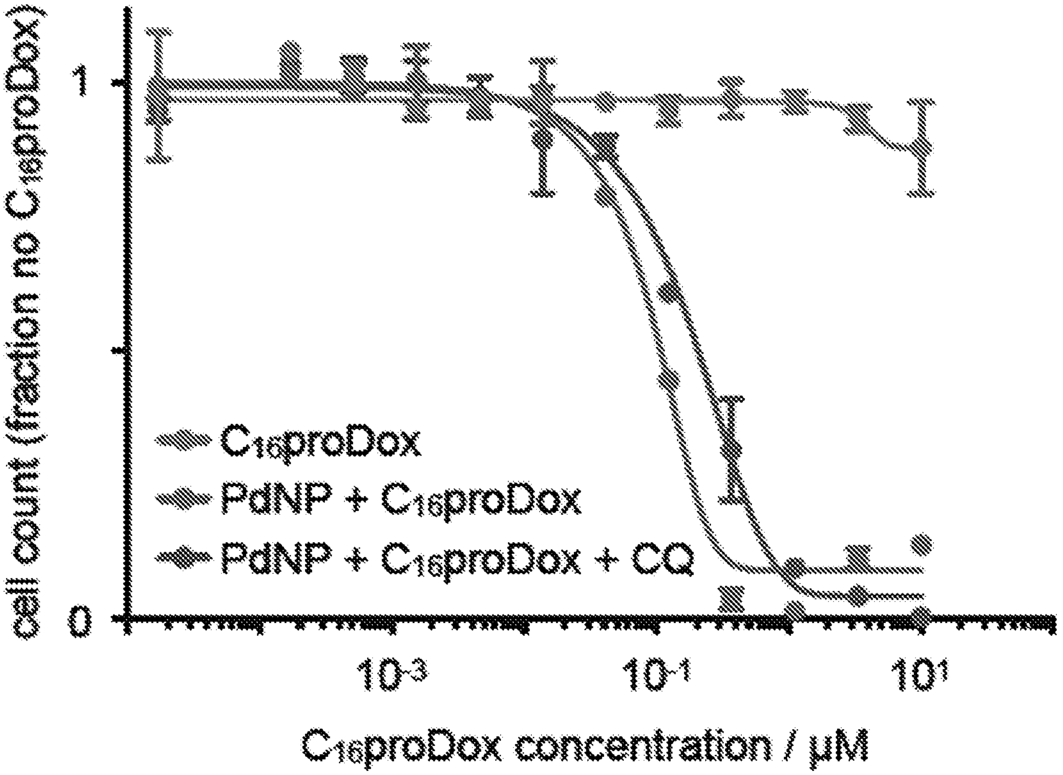

FIGS. 11A-11C. Microscopic evaluation of intracellular NP localization. a) Representative live-cell fluorescence microscopy of HT1080 tumor cells expressing either Rab7a-RFP or Lamp1-RFP fusion proteins, after 24 h incubation with a fluorescently labeled NP based on the prodrug formulation (PLGA-PEG+PLGA-BODIPY630). Data correspond with quantitation in FIG. 3*a*. b) Representative images of intrinsic anthracycline fluorescence of C16proDOX after 24 h incubation with HT1080 cells. Yellow and blue outlines denote cell and nuclei boundaries, respectively. Cells were co-treated with 50 μM chloroquine.

c) Cytotoxicity in HT1080 cells was measured after 72 h incubation with C16proDOX in the presence or absence of 50 μM Pd-NP and 50 μM chloroquine (data are means s.e.m.). Both scale bars, 10 μm.

FIGS. 12A-12G. Monitoring in vitro prodrug activation. a) HT1080 tumor cells were co-treated with C16proDOX and Pd-NP for 24 h, and then imaged by fluorescence microscopy to quantify subcellular drug accumulation based on endogenous fluorescence of anthracycline and Pd compound (scale bar 50 μm). b) Pixel-by-pixel co-localization was quantified by selecting ROI over perinuclear regions high in Pd signal based on images as in a (see yellow outlined regions in white dashed box for representative ROIs); for comparison, similar co-localization statistics were also computed for comparing PLGA-PEG NP vehicle (labeled with PLGA-BODIPY630) with a fluorescently-labeled, co-encapsulated C16 prodrug (C16-Pt(IV)-BODIPY; see [Miller et al., 2015, Nat Commun, 6, 8692]). c-d) HPLC fluorescence detection was used to discriminate doxorubicin and C16proDOX based on elution time (c, 50 μM standards), from HT1080 cell lysates following treatment. Representative HPLC fluorimetry trace (d) and corresponding quantification (e; means±s.d., n=3) are shown based on peaks at the described elution times. f) Representative ELSD detection of C16proMMAE activation by PdNP after 24 h. g) At red shading in f, LC-MS (ESI) calc for MMAE ($C_{39}H_{68}N_5O_7$ {M+H}+ 719.0, found 718.7) only detected with Pd-NP incubation (n=2).

Figure 13A:
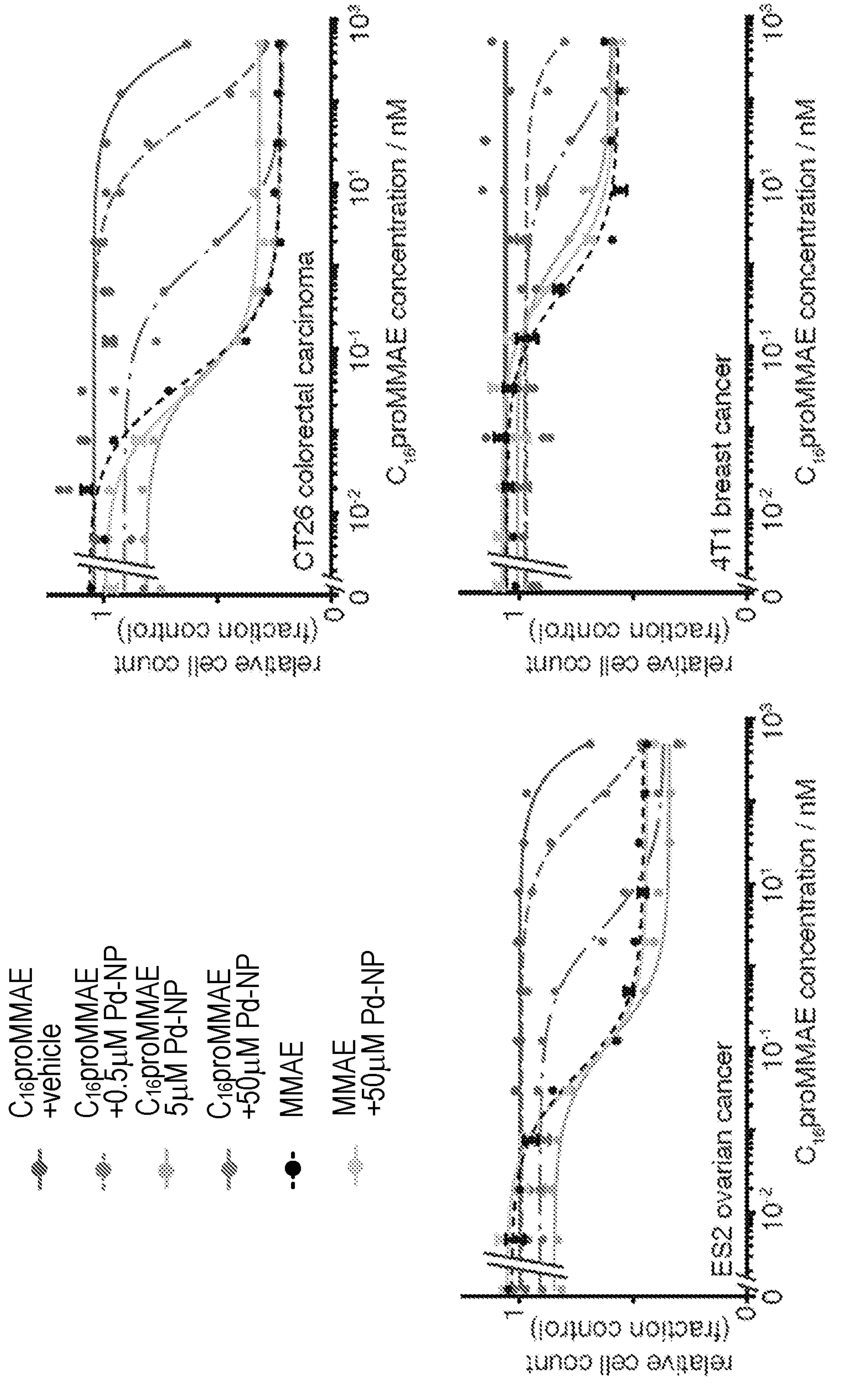
Figure 13B:
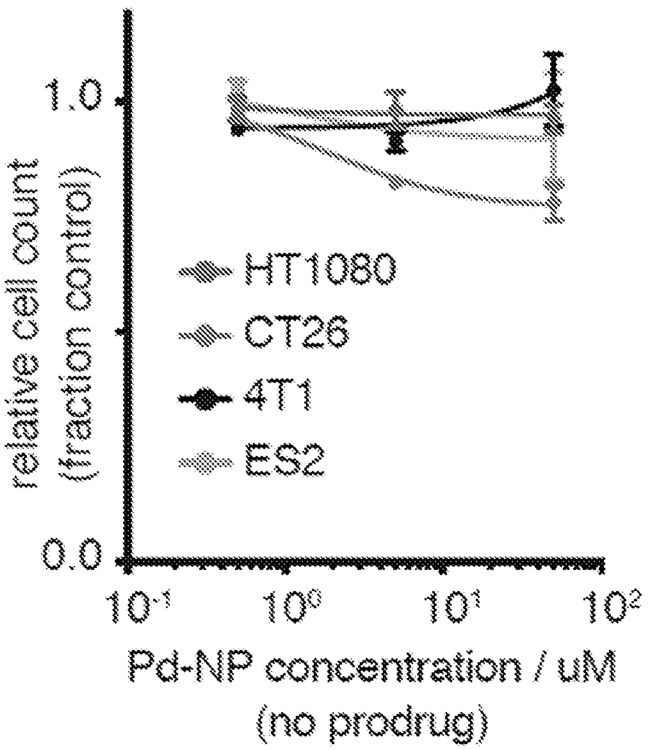

FIGS. 13A-13B. Dose-response of PdNP and prodrugs across multiple cancer cell lines. Cytotoxicity was measured using a resazurin-based assay 72 h after treatment. a) Viability was measured in response to varying amounts of MMAE or C16proMMAE in the presence or absence of Pd-NP. b) Viability was measured across 4 cancer cell lines in response to increasing concentrations of Pd-NP. Data are means±s.e.m. for all (n≥2).

FIGS. 14A-14E. Analysis of tumor growth data. a) Tissue concentrations of elemental Pd (left column), the PLGA-PEG vehicle (labeled with PLGA-BODIPY630) of a model nano-encapsulated prodrug substrate (Alloc2R110) (middle column), and the Pd-mediated activation of that substrate (right column) are shown 24 h post-administration in animals bearing HT1080 tumors. Concentration was determined by ICP-MS (for Pd) and reflectance fluorescence microscopy (for prodrug vehicle and prodrug activation), and normalized to the concentration found in tumors (n=3; see [Miller et al., 2017, Nat Commun, 8, 15906]). Data corresponds to FIG. 6*d*. b-c) Individual tumor growth curves, corresponding to FIGS. 5 and 7, are plotted alongside their mean (thick line) and s.e.m. (error bars) for the MC38 (b) and HT1080 (c) models. Red arrows denote the day of treatment. Representative tumor images show unaffected and blocked tumor growth at top and bottom, respectively, corresponding to their adjacent treatment groups (scale bar, 5 mm). d) The coefficient of variation (CV) in day 8 tumor volume measurements was calculated across both MC38 and HT1080 tumor models, including using single-treatment controls, solvent based formulation of doxorubicin, and a nanoformulated doxorubicin (see [Miller et al., 2017, Nat Commun, 8, 15906] for DOXNP and DOX treatments and descriptions; n≥5 tumors; F-test to compare variances of the treatment group against their respective no-treatment control). e) Weights of animals bearing HT1080 tumors were measured following local low-dose radiation and combination Pd-NP prodrug-NP treatments (n≥3; means±s.e.m.). Gray and red arrows denote RT and NP treatments FIG. 15 Pharmacokinetic model sensitivity analysis. Following parameter optimization, the pharmacokinetic model (see FIG. 6*a*) was computed while adjusting parameter values by ±10% (indicated along vertical axis). Change in simulation features 24 h following prodrug administration (horizontal axis) were quantified as a fraction of that feature's value. The ratio of fractional changes in feature values to fractional changes in parameter values (the parametric sensitivities) were then hierarchically clustered and plotted as a heatmap. "Long dose delay" describes changes observed when dose staggering is adjusted from 0 h (co-injection) to 24 h (but without changing the ratio denominator, Δ parameter, for comparison to "dose delay", which examines the impact of adjusting ±10% around the 5 h dose staggering. The yellow box highlights the relative impacts of PtSt on NP accumulation and prodrug activation in the tumor.

FIG. 16 Pharmacokinetic computational model parameters. Parameters used in the multi-compartment model are presented alongside references from which the values were taken. For parameters that were optimized to fit the experimental data, values are reported as means±std. dev. across n=24 optimization runs.

FIG. 17 Pharmacokinetic model equations.

FIG. 18 Pharmacokinetic model optimization parameters. Experimental data from the HT1080 tumor xenograft model, combined with complementary data from similar experimental and NP systems, were used to optimize the computational model (where indicated, data are means±s.e.m.).

FIG. 19 Overview of the prodrug strategy efficacy and safety. This table summarizes multiple publications using the HT1080 tumor xenograft model to describe the efficacy and safety profile of the materials described in this and other manuscripts.

Figure 20:
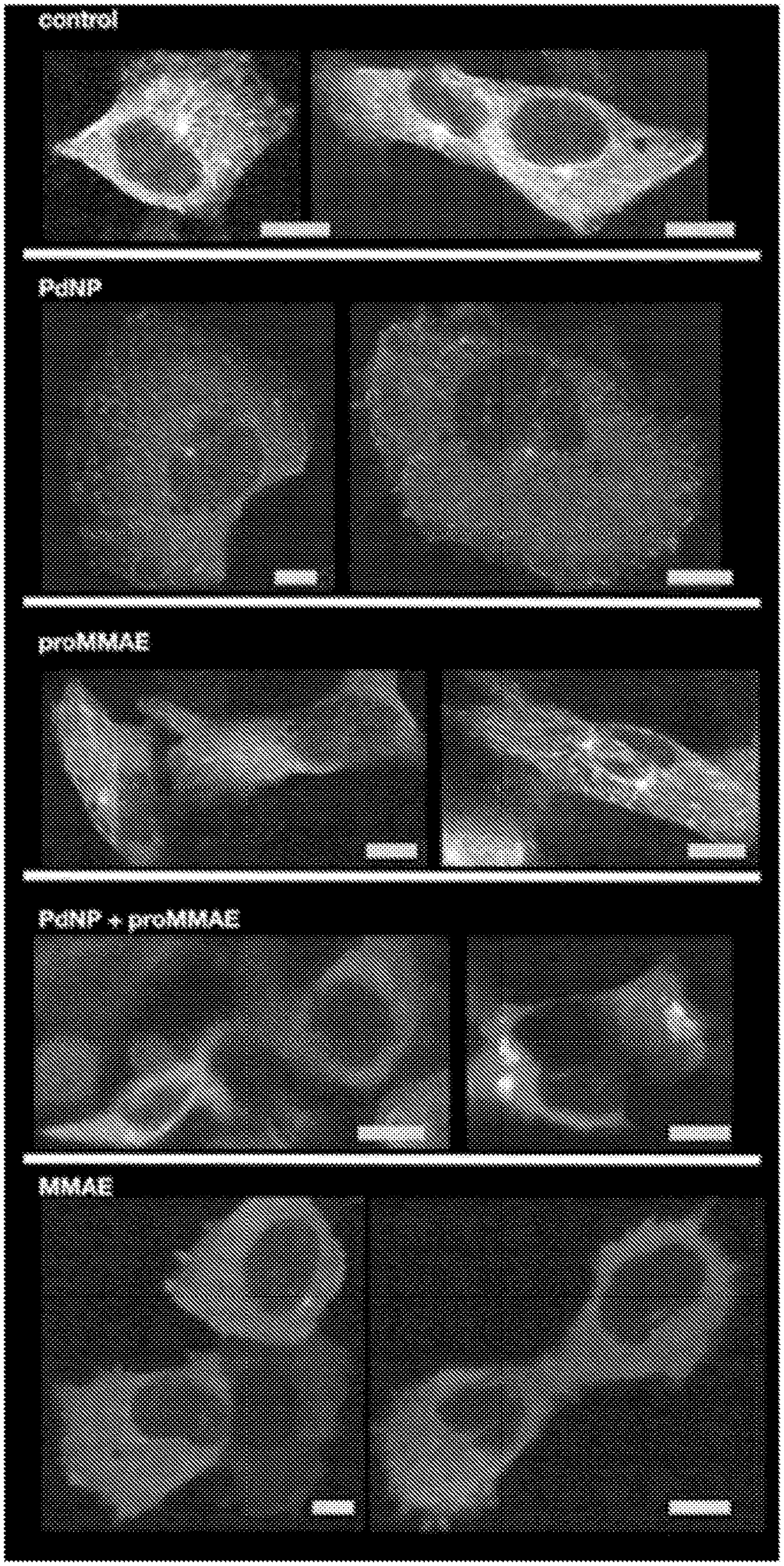

FIG. 20 Time-lapse microscopy of microtubule comets. Example movies (n=2 shown per condition) are depicted of HT1080 cancer cells expressing EB3-mApple over time. EB3-labeled microtubule comets are visible with control, Pd-NP, and C16proMMAE treatment conditions, but no comets are observed with MMAE or the dual-treatment Pd-NP+C16proMMAE combination. Time and length scales vary slightly across movies, on average showing 1-3 individual cells per movie and 1-5 seconds per movie frame. Scale bar 10 μm. Original resolution reduced for online access.

Figure 21:
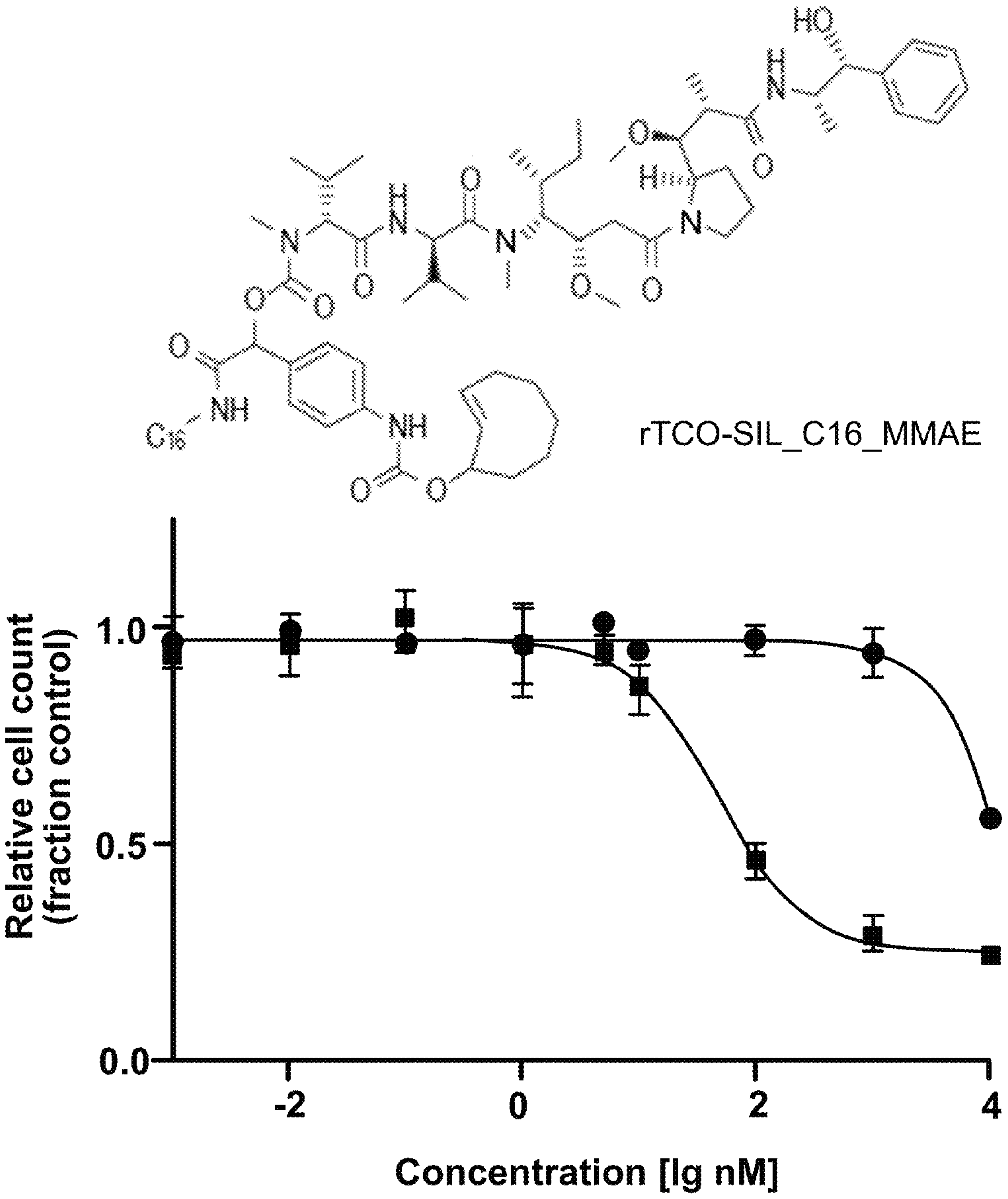

FIG. 21 The modular prodrug design (see FIG. 1) extends to activation triggers TR besides those which are activated by transition-metals such as palladium. In this example, rTco is used as a group that bio-orthogonally activated by a molecularly-targeted tetrazine derivative. Under activation by the targeted tetrazine derivative, cancer cells expressing the target antigen (lower curve) are killed preferentially compared to cells lacking the target antigen (upper curve). The x-axis reports dose response as a function of rTCO-SIL-$C_{16}$-MMAE, which is dose to cells here in the form of a polymer micelle nanoformulation based on PLGA-PEG nanoprecipitation.

Figure 22:
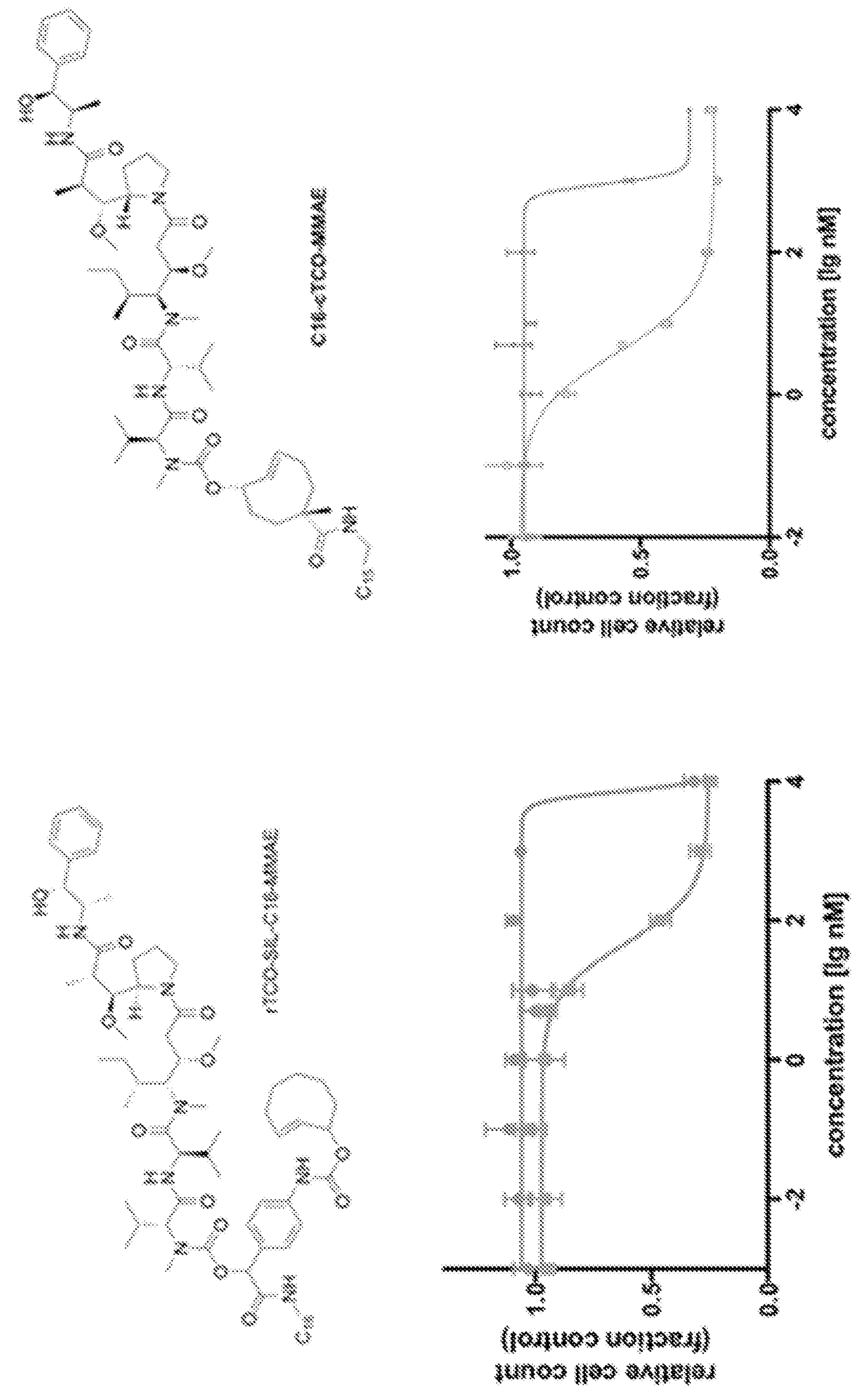

FIG. 22 The modular design has the potential to improve prodrug protection. We have data now showing that the incorporation of the SIL group in the prodrug formulation at left can improve the ability to reduce the activity of the caged drug moiety, compared to a very similar chemical strategy at right that lacks the SIL group. In some instances, the compound at right may exhibit ~10× cytotoxicity compared to the compound at left, in the absence of a triggering agent (such as a tetrazine derivative; shown by lower curves in this cancer cell cytotoxicity assay). This difference in cytotoxicity suggests the SIL-containing compound within the present claims (left, and FIG. 1) is a better prodrug candidate, because lower cytotoxicity in the absence of a prodrug trigger would lead to less non-specific drug activity outside of the target site in the body where triggering is designed to occur. Non-specific drug activity can lead to unwanted toxicity, especially for a highly toxic parent drug such as MMAE.

Figure 23:
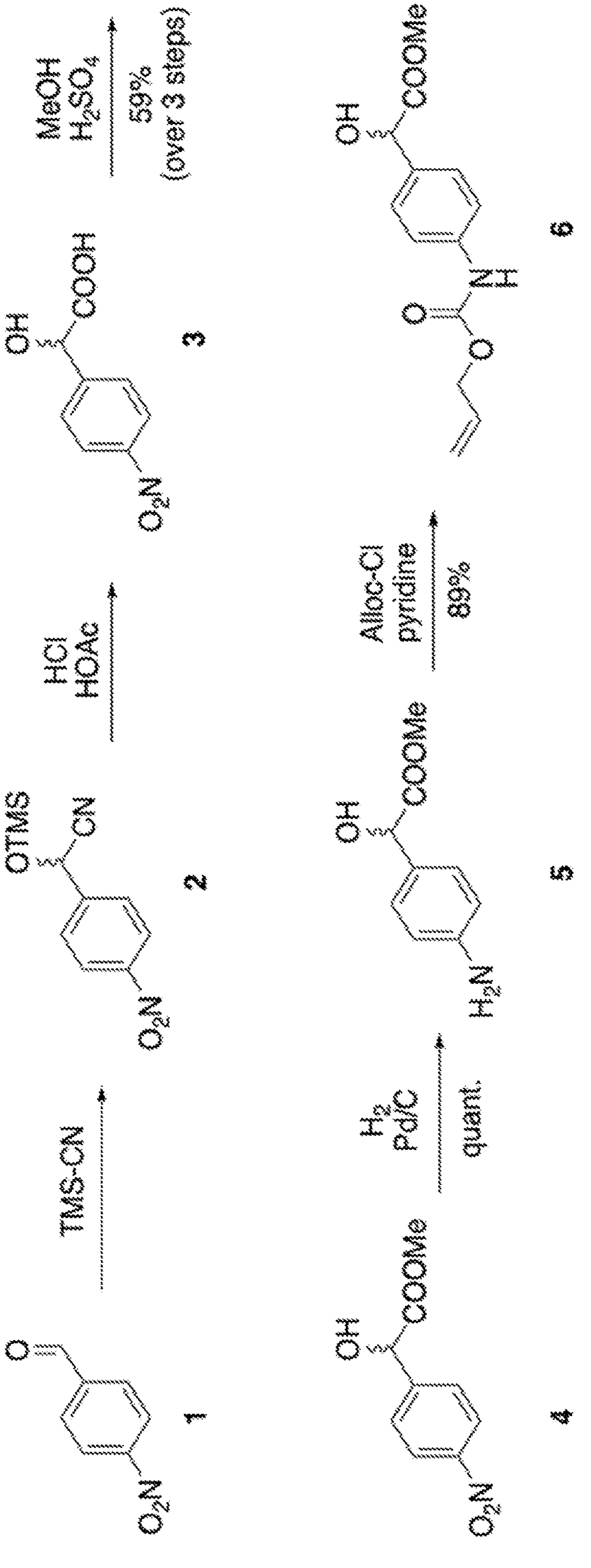

FIG. 23 Alloc-protected self-immolative linker (Alloc-SIL).

Figure 24:
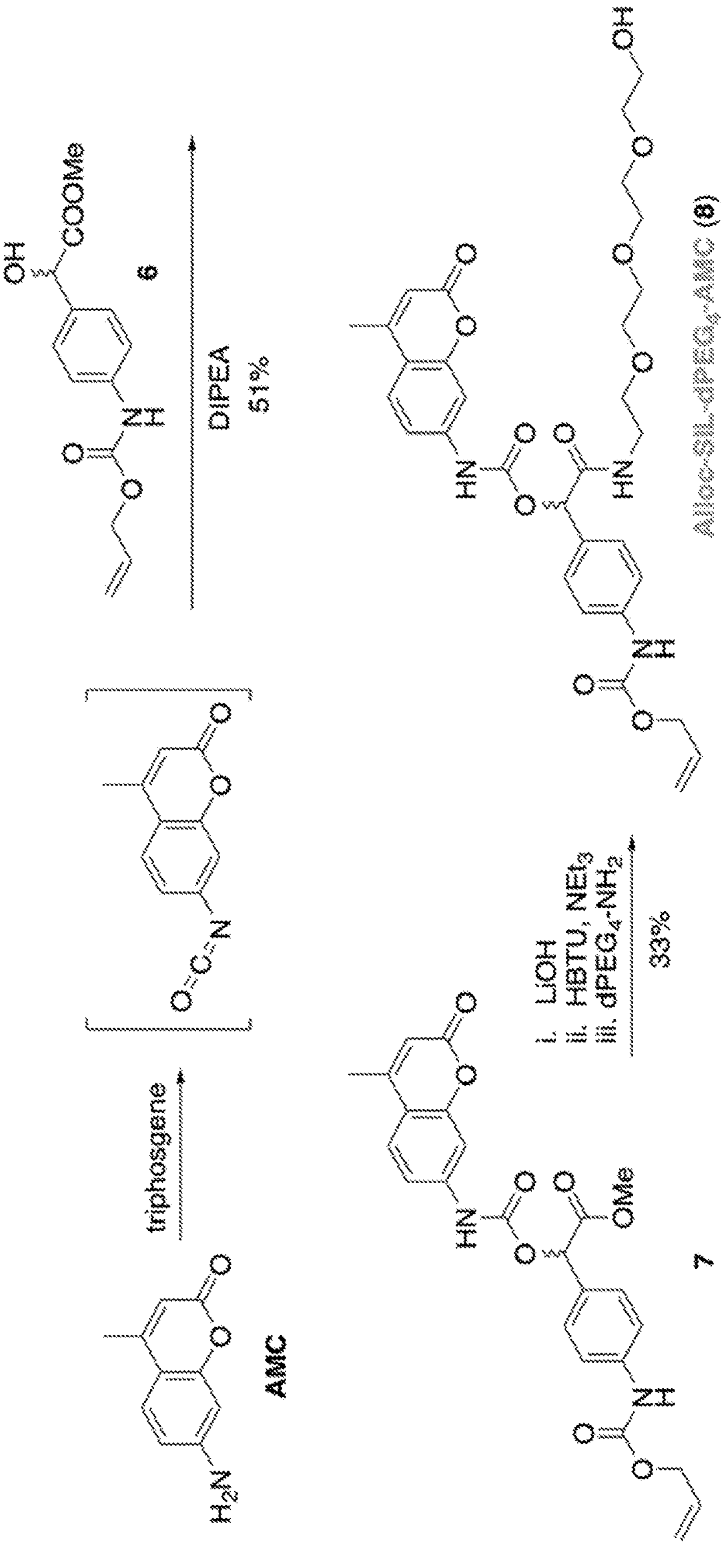

FIG. 24 Synthesis of fluorogenic Alloc-SIL-dPEG4-AMC.

Figure 25:
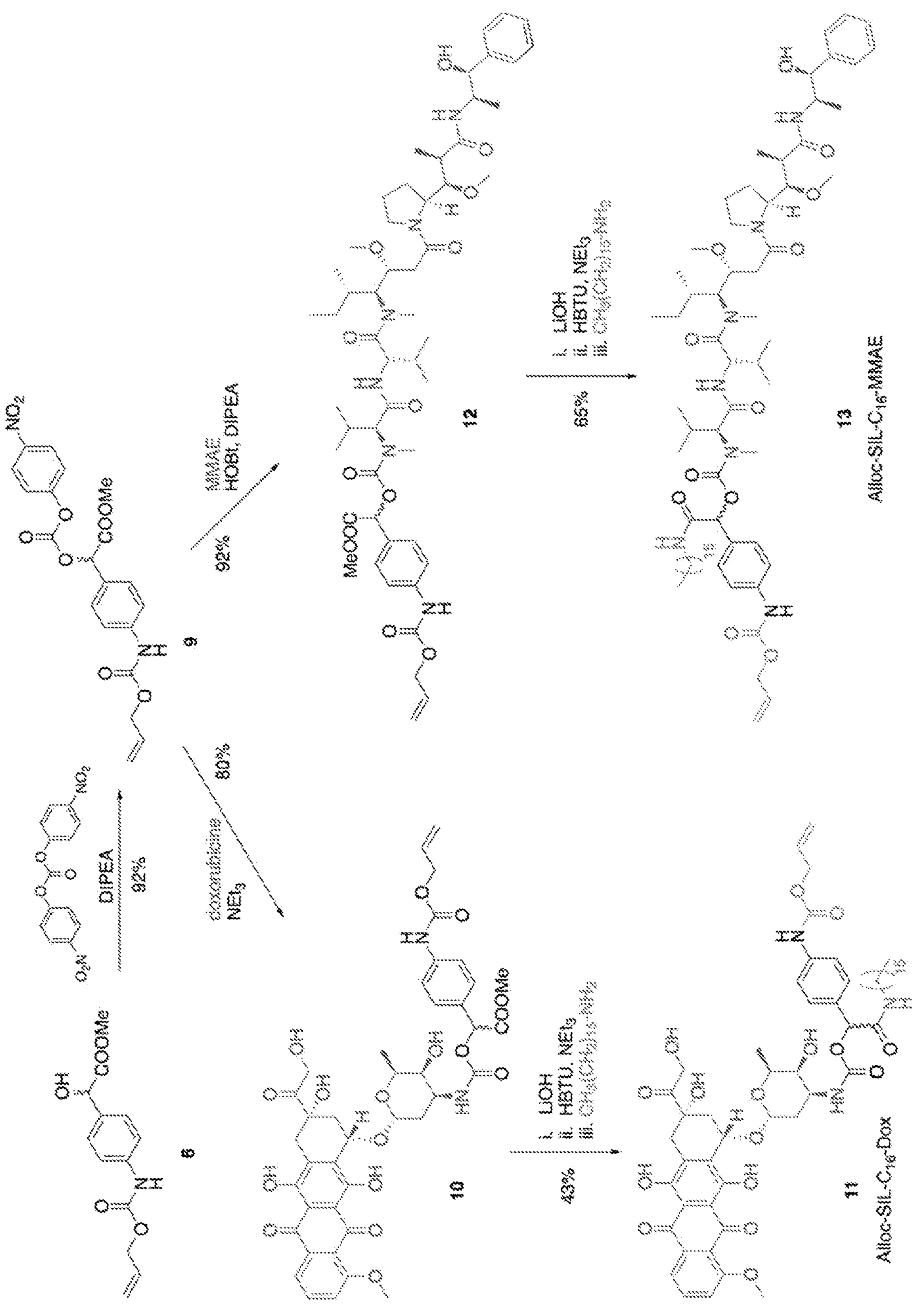

FIG. 25 Alloc-SIL-C16-drug conjugates.

FIG. 26 Palladium catalysts.

DETAILED DESCRIPTION

Bioorthogonal chemical reactions are increasingly developed as tools for the controlled delivery and activation of therapeutics, molecular imaging or detection agents, and as synthetic biology reagents.[1] “Ligation” reactions, for example based on stepwise administration of a pre-targeting agent and a complementary imaging[2] or drug[3] ligand, have demonstrated the potential of using bioorthogonal approaches such as inverse electron-demand Diels-Alder reaction (IEDDA) to enhance selective targeting in models of cancer. Alternatively, bioorthogonal bond cleavage reactions[1] may employ a variety of strategies, including (i) photo-induced decaging using nitroaromatics,[4] (ii) deallylation using palladium[5] and ruthenium catalysts,[6] (iii) depropargylation using palladium[7] or gold[8] particles, (iv) IEDDA-induced ‘click-to-release’.[9] and (v) cleavage induced by strain-promoted alkene-azide cycloaddition.[10]

Prodrugs are a proven route to limiting exposure in off-target tissues, especially for cytotoxic anticancer compounds such as microtubule-targeting agents. Drug caging, typically by protecting a primary amine critical for drug activity, can be used to restrict drug action until the prodrug is activated by a spatiotemporally controlled de-protection reaction. Nanoparticle formulation can achieve the same goals, and it is appealing, in principle, to combine the two approaches for controlling exposure in target vs. off-target tissues. Sufficient drug activation at the target disease site is often a limiting factor for both prodrug and nanoparticle (NP) strategies. Reactants are required to maintain chemical stability until they reach the target, at which point they must sufficiently react to achieve therapeutically active drug concentrations. Compared to click-chemistry approaches, bioorthogonal catalysts have been attractive for their diverse reactivity and efficient activation of caged compounds. Unfortunately, most strategies with transition metal catalysts have relied on microparticles,[8] elemental powders and resins,[11] and for traditional synthetic chemistry applications, simple salts or phenylphosphines, all of which have issues with biocompatibility, stability, toxicity, and systemic bioavailability. As a result, in vivo demonstration of bioorthogonal catalysis has been limited, especially as applied to nano formulated drugs.

Recently, a nano-encapsulated palladium catalyst (Pd-NP) was reported to overcome these issues using bis[tri(2-furyl)phosphine]palladium(II) dichloride, $PdCl_2(TFP)_2$, in a biocompatible poly(lactic-co-glycolic acid)-b-polyethyleneglycol platform.[5] The 60 nm Pd-NP formulation demonstrated stability in biological solutions and exploited the “enhanced permeability and retention” (EPR) effect to passively accumulate in solid tumors following systemic administration. The EPR effect is further exploited by co-administering a separate nano-formulation of prodrug, which cooperatively reduces off-target drug activation and toxicity.[5] Pd-NP has been both safe and effective at locally activating prodrug in xenograft tumors, and its first demonstration relied on model allyloxycarbonyl (Alloc) and propargyloxycarbonyl (Poc) derivatives of the DNA-damaging chemotherapeutic, doxorubicin. Although effective, this amphiphilic prodrug was nano-encapsulated with relatively poor efficiency (22%), and its relatively low potency in cell killing required high doses.[5] Furthermore, other drugs may be completely incompatible for nano-encapsulation or activity caging with this approach.

In some embodiments, described herein is a bioorthogonal cleavage strategy based on coupling palladium-catalyzed deallylation with a self-immolative linker, which has been functionalized with an aliphatic anchor for efficient nano-encapsulation and blockage of prodrug action. This strategy provides a modular platform for adding functionality to prodrugs, in this case increasing prodrug nano-encapsulation efficiency to >90%, and enabling $\geq 10^4$ fold-increase in cytotoxicity upon prodrug activation. In one example, a prodrug of the microtubule targeting agent, monomethyl auristatin E (MMAE) was used as the drug. MMAE is typical of a drug that is too toxic for systemic delivery, but that has met with success using tumor-selective targeting mostly in antibody-drug conjugates (ADCs). However, ADCs are very limited in the on-target exposure that they can achieve. Caged MMAE was formulated as a NP using alkyl chain immobilization, thus combining two principles for improving tumor vs. whole body exposure. Upon activation by Pd-NP, caged MMAE (C16proMMAE) disrupts microtubule activity in live cells and becomes cytotoxic at <100 pM. $C_{16}$proMMAE safely blocks tumor growth in mouse models of cancer when combined with Pd-NP. Computational modeling suggests that the dual NP strategy can limit systemic exposure of toxic activated drugs relative to what is achieved in the tumor, but especially relies on the EPR effect. Single low-dose radiation to enhance EPR led to synergistic tumor shrinkage when combined with the prodrug strategy within the present claims.

Methods of Use

The compounds, linkers, nanoparticles, and combination therapies described in this application can be used to treat a pathology, disease, or condition in a subject (e.g., a subject in need thereof). The subject may be in need of treatment when diagnosed with the disease, pathology, or condition by a competent physician (e.g., oncologist). Accordingly, the present disclosure also provides use of a composition comprising compounds, linker, and nanoparticles of the present disclosure in the manufacture of a medicament for the treatment of any of the diseases or conditions disclosed in this application. In addition, the present disclosure also provides compounds, linkers, nanoparticles, and combination therapies for use in a method for treating any of the diseases or conditions disclosed in this application.

In some embodiments, the disease or condition is cancer. Suitable examples of cancer include bladder cancer, brain cancer, breast cancer, colorectal cancer (e.g., colon cancer), rectal cancer, cervical cancer, gastrointestinal cancer, genitourinary cancer, head and neck cancer, lung cancer, oral cancer, ovarian cancer, pancreatic cancer (e.g., pancreatic neuroendocrine tumor), prostate cancer, endometrial cancer, renal cancer (kidney cancer) (e.g., advanced kidney cancer), skin cancer, liver cancer, thyroid cancer, leukemia, and testicular cancer.

In some embodiments, cancer is selected from sarcoma, angiosarcoma, fibrosarcoma, rhabdomyosarcoma, liposarcoma, myxoma, rhabdomyoma, fibroma, lipoma, teratoma, lung cancer, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, chondromatous hamartoma, mesothelioma, gastrointestinal cancer, cancer of the esophagus, squamous cell carcinoma, adenocarcinoma, leiomyosarcoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma, hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, brain cancer, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

In some embodiments, the disease of condition is inflammation. In some embodiments, the disease or condition is an inflammatory disease or condition. In some embodiments, the inflammatory disease or condition is selected from arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, *piriformis* syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis In some embodiments, the disease or condition is a bacterial infection or a viral infection. In these embodiments, the compounds, drugs, conjugates, nanoparticles, and compositions of the present disclosure may be used to prevent a bacterial infection (e.g., by targeted delivery of the drug to a wound or injury site or a surgical site). Suitable examples of bacterial infections include bacterial infections caused by the bacteria of a genus selected from the group consisting of *Staphylococcus, Streptococcus, Peptococcus, Enterococcus*, and *Bacillus*. That is, the bacterial infection may be caused by the bacteria of a species selected from the group consisting of *S. aureus*, methicillin-resistant *S. aureus* (MRSA), vancomycin-resistant *S. aureus* (VRSA), *E. faecalis, E. faecium, B. subtilis*, and *B. anthracis*. In some embodiments, the bacterial infection is selected from the group consisting of nosocomial infection, skin infection, respiratory infection, wound infection, endovascular infection, CNS infection, abdominal infection, blood stream infection, urinary tract infection, pelvic infection, invasive systemic infection, gastrointestinal infection, dental infection, zoonotic infection, and connective tissue infection. In some embodiments, the bacterial infection is selected from the group consisting of atopic dermatitis, sinusitis, food poisoning, abscess, pneumonia, meningitis, osteomyelitis, endocarditis, bacteremia, sepsis, and urinary tract infection.

In some embodiments, the disease or condition is an endocrine disorder. In some embodiments, the endocrine disorder is diabetes, diabetes mellitus, diabetic ketoacidosis, hyperkalaemia, hyperglycemia, growth failure due to GH deficiency or chronic renal insufficiency, Prader-Willi syndrome, Turner syndrome, AIDS wasting or cachexia with antiviral therapy, growth failure in children with GH gene deletion or severe primary IGF1 deficiency, postmenopausal osteoporosis, severe osteoporosis, type 2 diabetes resistant to treatment with metformin and a sulphonylurea, or acromegaly.

In some embodiments, the disease or condition is associated with haemostasis and thrombosis. In some embodiments, the disease or condition associated with haemostasis and thrombosis is selected from haemophilia A, haemophilia B, hereditary AT-III deficiency in connection with surgical or obstetrical procedures or for thromboembolism, venous thrombosis and purpura fulminans in patients with severe hereditary protein C deficiency, pulmonary embolism, myocardial infarction, acute ischaemic stroke, occlusion of central venous access devices, acute myocardial infarction, haemorrhage in patients with haemophilia A or B and inhibitors to factor VIII or factor IX, severe sepsis with a high risk of death, heparin-induced thrombocytopaenia, blood-clotting risk in coronary angioplasty, acute evolving transmural myocardial infarction, deep vein thrombosis, arterial thrombosis, occlusion of arteriovenous cannula, and thrombolysis in patients with unstable angina.

In some embodiments, the disease or condition is pulmonary or gastrointestinal-tract disorder. In some embodiments, the pulmonary or gastrointestinal-tract disorder is congenital α-1-antitrypsin deficiency, gas, bloating, cramps and diarrhea due to inability to digest lactose, cystic fibrosis, chronic pancreatitis, pancreatic insufficiency, post-Billroth II gastric bypass surgery, pancreatic duct obstruction, steatorrhoea, poor digestion, gas, or bloating.

In some embodiments, the disease or condition is associated with immunodeficiencies. In some embodiments, the disease or condition is associated with immunodeficiencies is severe combined immunodeficiency disease due to adenosine deaminase deficiency or primary immunodeficiencies.

In some embodiments, the disease or condition is associated with haematopoiesis. In some embodiments, the disease or condition is associated with haematopoiesis is anaemia, myleodysplasia, anaemia due to renal failure or chemotherapy, preoperative preparation, anaemia in patients with chronic renal insufficiency and chronic renal failure (+/− dialysis), neutropaenia, neutropaenia in AIDS or post-chemotherapy or bone marrow transplantation, severe chronic neutropaenia, leukopaenia, myeloid reconstitution post-bone-marrow transplantation, or thrombocytopaenia (especially after myelosuppressive chemotherapy).

In some embodiments, the disease or condition is associated with growth regulation. In some embodiments, the disease or condition is associated with growth regulation is acromegaly, symptomatic relief of VIP-secreting adenoma and metastatic carcinoid tumours, spinal fusion surgery, bone injury repair, tibial fracture nonunion, lumbar, spinal fusion, precocious puberty, severe oral mucositis in patients undergoing chemotherapy or debridement adjunct for diabetic ulcers.

In some embodiments, the disease or condition is decubitus ulcer, varicose ulcer, debridement of eschar, dehiscent wound, sunburn, or acute decompensated congestive heart failure. In some embodiments, the disease or condition is infectious disease. In some embodiments, the infectious disease is HIV infection, or AIDS. In some embodiments, the disease or condition is Hepatitis B, Hepatitis C, HIV, HPV, or Lyme disease. In some embodiments, the compounds, conjugates, prodrugs, nanoparticles, compositions, and combination therapies of the present disclosure can be administered to the subject in combination with radiation therapy, surgery, biological therapy, anti-angiogenesis therapy, immunotherapy, adoptive transfer of effector cells, gene therapy, or hormonal therapy.

Compounds of Formula (I):

This disclosure provides compounds with a branched (tridentate) structure to enable multifunctional prodrug design, comprising of a therapeutic entity (e.g., a drug moiety), an anchoring or conjugation element that also modifies drug action while covalently conjugated (e.g., an aliphatic chain for efficient nano-encapsulation), a self-immolative linker, and a group that releases under appropriate conditions (e.g., functional groups that react with a bio-orthogonal catalyst such as with certain palladium compounds).

In some embodiments, the present disclosure provides a compound of Formula (I):

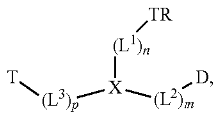

or a pharmaceutically acceptable salt thereof, wherein $L^1$, n, $L^2$, m, $L^3$, p, X, T, TR, and D are as described herein.

In some embodiments:

X is a tridentate self-immolative linker;

each $L^1$ is independently selected from $N(R^N)$, O, C(=O), S, S(=O), $S(=O)_2$, $C_{1-6}$ alkylene, $C_{3-7}$ cycloalkylene, $C_{6-10}$ arylene, $-(OCH_2CH_2)_x-$, $-(CH_2CH_2O)_x-$, $-(OCH(CH_3)CH_2)_x-$, and $-(CH_2CH(CH_3)O)_x-$, n is an integer from 0 to 10;

each $L^2$ is independently selected from $N(R^N)$, O, C(═O), S, S(═O), $S(═O)_2$, $C_{1-6}$ alkylene, $C_{3-7}$ cycloalkylene, $C_{6-10}$ arylene, —$(OCH_2CH_2)_x$—, —$(CH_2CH_2O)_x$—, —$(OCH(CH_3)CH_2)_x$—, and —$(CH_2CH(CH_3)O)_x$—, m is an integer from 0 to 10;

each $L^3$ is independently selected from $N(R^N)$, O, C(═O), S, S(═O), $S(═O)_2$, $C_{1-6}$ alkylene, $C_{3-7}$ cycloalkylene, $C_{6-10}$ arylene, —$(OCH_2CH_2)_x$—, —$(CH_2CH_2O)_x$—, —$(OCH(CH_3)CH_2)_x$—, and —$(CH_2CH(CH_3)O)_x$—, p is an integer from 0 to 10;

each x is independently an integer from 1 to 2,000;

each $R^N$ is independently selected from H, $C_{1-3}$ alkyl, and $C_{1-3}$ haloalkyl;

T is a ligand moiety;

TR is a trigger-sensitive moiety; and

D is a drug moiety.

Linkers $L^1$, $L^2$, and $L^3$

In some embodiments, n is an integer from 0 to 7. In some embodiments, n is an integer from 1 to 5. In some embodiments, n is 1. In some embodiments, n is 2. In some embodiments, n is 3. In some embodiments, n is 0.

In some embodiments, each $L^1$ is independently selected from NH, O, C(═O), $C_{1-6}$ alkylene, $C_{6-10}$ arylene, —$(OCH_2CH_2)_x$—, and —$(CH_2CH_2O)_x$—.

In some embodiments, n is an integer from 0 to 5, and each $L^1$ is selected from NH, O, C(═O), $C_{1-6}$ alkylene, and $C_{6-10}$ arylene.

In some embodiments, n is 1 and $L^1$ is $C_{1-6}$ alkylene.

In some embodiments, m is an integer from 0 to 7. In some embodiments, m is an integer from 1 to 5. In some embodiments, m is at least 1. In some embodiments, m is an integer from 2 to 10. In some embodiments, m is an integer from 3 to 7. In some embodiments, m is 0.

In some embodiments, each $L^2$ is independently selected from NH, O, C(═O), $C_{1-6}$ alkylene, $C_{6-10}$ arylene, —$(OCH_2CH_2)_x$—, and —$(CH_2CH_2O)_x$—.

In some embodiments, m is an integer from 1 to 5, and each $L^2$ is independently selected from NH, O, C(═O), $C_{1-6}$ alkylene, $C_{6-10}$ arylene, —$(OCH_2CH_2)_x$—, —$(CH_2CH_2O)_x$—, —$(OCH(CH_3)CH_2)_x$—, and —$(CH_2CH(CH_3)O)_x$—.

In some embodiments, m is 4, and each $L^2$ is independently selected from NH, C(═O), $C_{1-6}$ alkylene, and —$(OCH_2CH_2)_x$—.

In some embodiments, p is an integer from 0 to 7. In some embodiments, p is an integer from 1 to 5. In some embodiments, p is at least 1. In some embodiments, p is an integer from 2 to 10. In some embodiments, p is an integer from 3 to 7. In some embodiments, p is 0.

In some embodiments, each $L^3$ is independently selected from NH, O, C(═O), $C_{1-6}$ alkylene, $C_{6-10}$ arylene, —$(OCH_2CH_2)_x$—, and —$(CH_2CH_2O)_x$—.

In some embodiments, p is an integer from 1 to 7, and each $L^3$ is independently selected from NH, O, C(═O), $C_{1-6}$ alkylene, $C_{6-10}$ arylene, and —$(OCH_2CH_2)_x$—.

In some embodiments, p is 3, and each $L^3$ is independently selected from NH, 0, and C(═O).

In some embodiments, x is an integer from 2 to 10. In some embodiments, x is 3, 4, 5, or 6.

In some embodiments:

n is an integer from 1 to 5, and each $L^1$ is selected from NH, O, C(═O), $C_{1-6}$ alkylene, and $C_{6-10}$ arylene;

m is an integer from 1 to 5, and each $L^2$ is independently selected from NH, O, C(═O), $C_{1-6}$ alkylene, $C_{6-10}$ arylene, —$(OCH_2CH_2)_x$—, —$(CH_2CH_2O)_x$—, —$(OCH(CH_3)CH_2)_x$—, and —$(CH_2CH(CH_3)O)_x$—;

p is an integer from 1 to 7, and each $L^3$ is independently selected from NH, O, C(═O), $C_{1-6}$ alkylene, $C_{6-10}$ arylene, and —$(OCH_2CH_2)_x$—; and x is an integer from 2 to 10.

In some embodiments:

n is 1 and $L^1$ is $C_{1-6}$ alkylene;

m is 4, and each $L^2$ is independently selected from NH, C(═O), $C_{1-6}$ alkylene, and —$(OCH_2CH_2)_x$—;

p is 3, and each $L^3$ is independently selected from NH, O, and C(═O); and x is an integer from 2 to 10.

In some embodiments, n is 0, m is 0, and p is 0. In some embodiments, n is 1, m is 1, and p is 1. In some embodiments, n is 0, m is 1, and p is 1.

In some embodiments, each of $L^1$, $L^2$, and $L^3$ may be independently selected from any one of the linkers described, for example, in WO2014100762A1, WO2015038426A1, WO2005112919A2, which are incorporated herein by reference.

The linkers $L^1$, $L^2$, and $L^3$ could be designed to modify the pharmacokinetics of the prodrug and/or targeting agent, such that the behavior of either changes upon triggered dissociation.

Self-Immolative Linkers

Figure 1A:
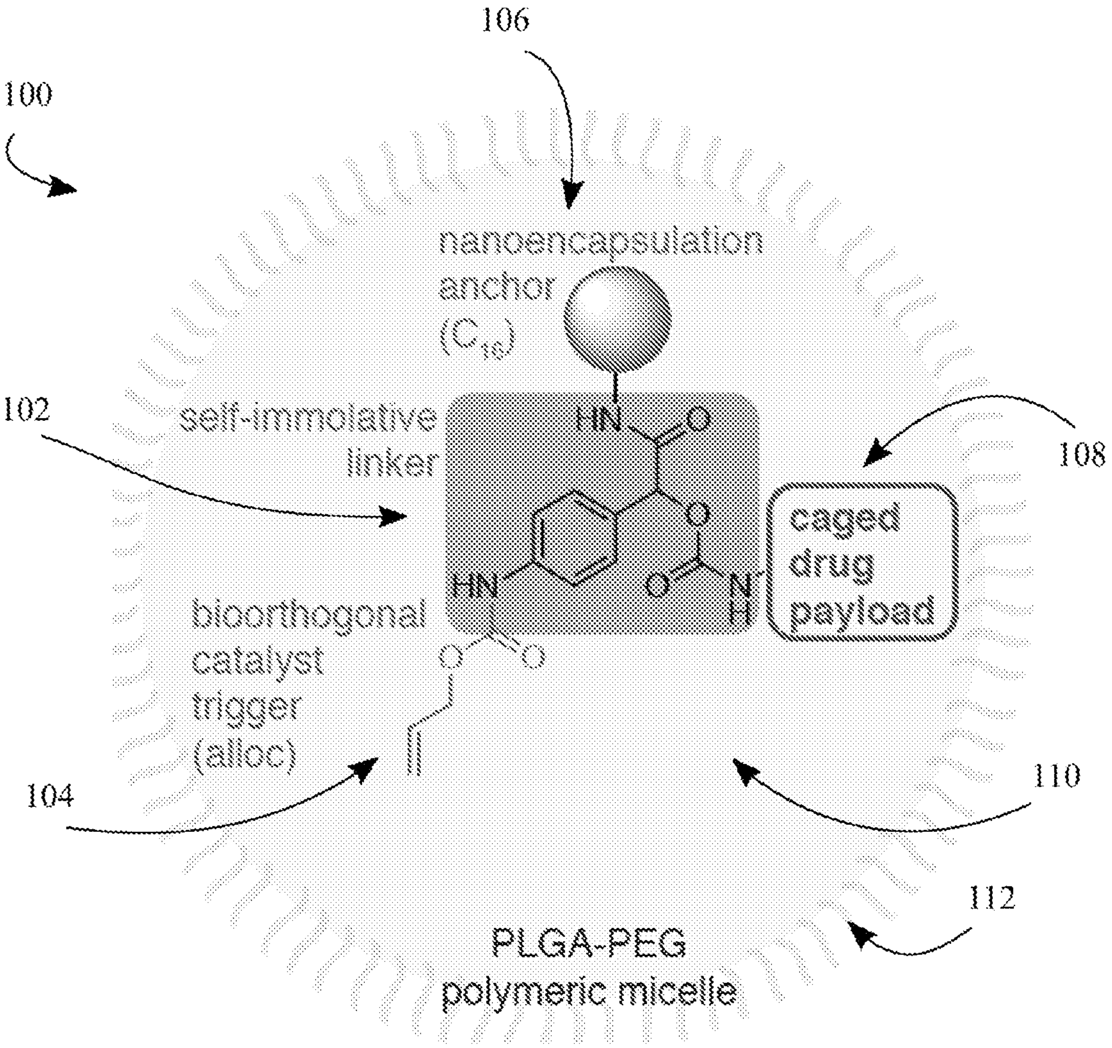
FIG. 1A is a schematic illustration of a nanoparticle 100 containing a pro-drug within the present claims. A self-immolative linker (102) bridges three modular functional aspects of an inactive non-toxic prodrug: a bioorthogonally-cleavable protective group (104, allyloxycarbonyl, alloc) that is removed upon exposure to a triggering agent (114, see FIG. 1B), a nano-encapsulation anchor (106, an aliphatic C16 chain), and the caged drug payload (108).
Figure 1B:
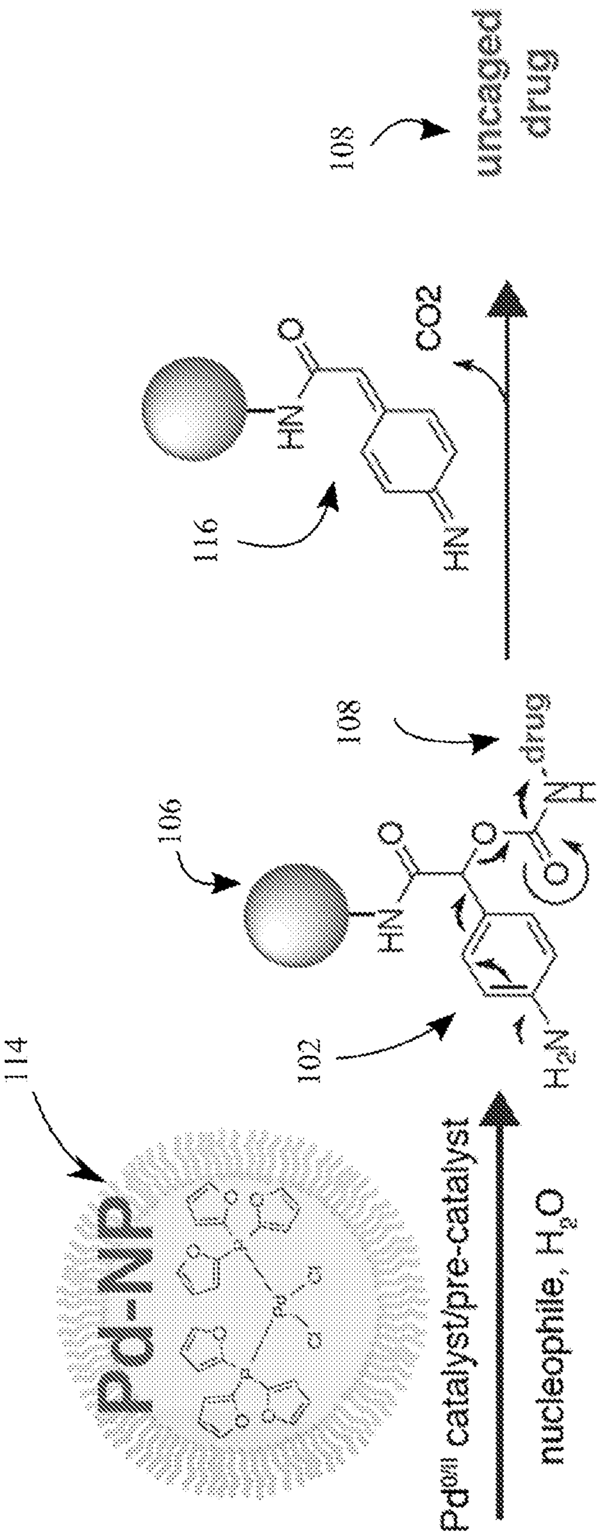
FIG. 1B is an overview of the drug release strategy. A bioorthogonal activating agent, 114 (Pd-NP), based on the polymeric micellar encapsulation of $PdCl_2(TFP)_2$, leads to drug 108 uncaging and activation in a spatiotemporally-controlled manner.

Group X can be a tridentate self-immolative linker, one example of the tridentate self-immolative linker is the mandelic acid derivatives (e.g., p-amino mandelic acid derivative). Other suitable examples include linkers described in Blencowe et al., 2011, Polym Chem, 2, 773-790, WO2014100762A1, WO2004043493, WO2009017394 (A1), U.S. Pat. No. 7,375,078, WO2015038426A1, WO2005112919A2, Yan et al., 2018, Chem Soc Rev, 47, 6900-6916, Roth et al., 2016, Chem Rev, 116, 1309-52, and Angew. Chem. Int. Ed. 2015, 54, 7492-7509, all of which are incorporated herein by reference in their entirety. Self-immolative linkers have the general property of exhibiting relative stability to link the prodrug components (D, T) with a trigger-sensitive group (TR). Once TR is reacted or activated, for instance in response to contact with a trigger reagent or catalyst, which may be an environmental, biological, chemical, or physical interaction (e.g., via reaction with biorthogonal catalyst herein), the self-immolative linker becomes labile and disassembles, therefore releasing D and T. An example of the release cascade is shown in FIG. 1B. Here, when the compound of Formula (I) having Alloc trigger sensitive (TR) moiety is reacted in the target cell with the Pd-based bioorthogonal catalyst 114, the Alloc trigger-sensitive group is cleaved from the compound of Formula (I) leaving behind a compound comprising activated self-immolative linker 102, ligand T 106, and the drug moiety D. The activated SIL engages in the self-immolation degradation reaction (as shown by arrows), leading to the release of the drug D 108 in its biologically active, chemically unaltered, form, for the drug D to exert its biological activity in the target cell. The immolation cascade also leads to release of the ligand T that is chemically modified with the residue of the self-immolative linker 116.

In some embodiments, the self-immolative linker X has formula:

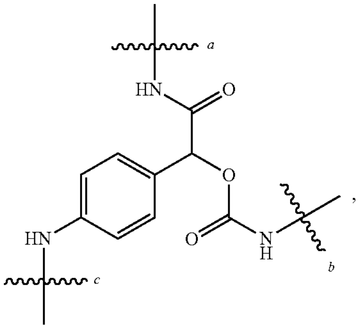

wherein a denotes a point of attachment of the linker to $L^3$, b denotes a point of attachment of the linker to $L^2$, and c denotes a point of attachment of the linker to $L_1$.

In some embodiments, the compound of Formula (I) has formula:

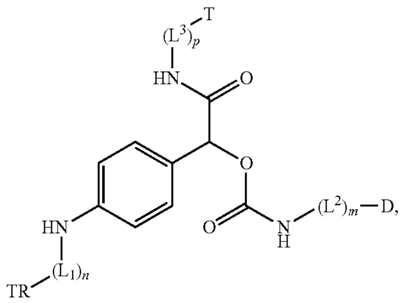

or a pharmaceutically acceptable salt thereof.

In some embodiments, D, $L^2$, and NH to which $L^2$ is attached all form a part of the biologically active drug upon activation and cleavage of the self-immolative linker.

In some embodiments, the compound of Formula (I) has formula:

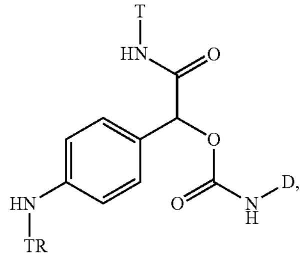

or a pharmaceutically acceptable salt thereof.

In some embodiments, the NH group that is attached to D moiety in Formula (I) becomes a part of the drug D after the drug is release from the conjugate (i.e., the drug D comprises an $NH_2$ group that is attached to the self-immolative linker X in Formula (I).

Ligand Groups (T)

In some embodiments, the ligand moiety T is an anchoring or a solubilization moiety. In some embodiments, T is a solubilization moiety. That is, T can be used to increase the aqueous solubility of the compound of Formula (I). In this example, the T group is a hydrophilic group. Suitable examples of hydrophilic groups include OH-$C_{1-22}$ alkyl and an aliphatic (or hydrophilic) polymer (e.g., polyethylene glycol). A hydrophilic polymer may be, for example, poly (alkylene glycol), poly(oxyethylated polyol), poly(olefinic alcohol), poly(β-hydroxy acid), poly(vinyl alcohol), polyoxazoline, or a copolymer thereof. A polyalkylene glycol includes linear or branched polymeric polyether polyols. Such polyalkylene glycols, include, but are not limited to, polyethylene glycol (PEG), polypropylene glycol, polybutylene glycol, and derivatives thereof. Other exemplary embodiments are listed, for example, in commercial supplier catalogs, such as Shearwater Corporation's catalog "Polyethylene glycol and Derivatives for Biomedical Applications" (2001).

In some embodiments, such polymeric polyether polyols have average molecular weights between about 0.1 kDa to about 100 kDa. For example, such polymeric polyether polyols include, but are not limited to, between about 500 Da and about 100,000 Da or more. The molecular weight of the polymer may be between about 500 Da and about 100,000 Da. For example, a polymer used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, a polymer is a linear or branched poly(ethylene glycol). In some embodiments, the poly(ethylene glycol) molecule is a linear polymer. Linear PEG can be alkylated (e.g., methylated or ethylated), at one termini, but they can by incorporated to the conjugate of any one of the formulae disclosed herein using the free terminus in the non-derivatized hydroxyl form. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. For example, branched PEG can be V-shaped, or T-shaped, depending on the method by which PEG has been synthesized. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, the polyethylene glycol (linear or branched) has an average molecular weight from about 500 Da to about 40,000 Da, from about 1,000 Da to about 30,000 Da, from about 1,000 Da to about 20,000 Da, from about 5,000 Da to about 20,000 Da.

In some embodiments, the polymer (e.g., the polyethylene glycol) as provided herein has the following structural formula:

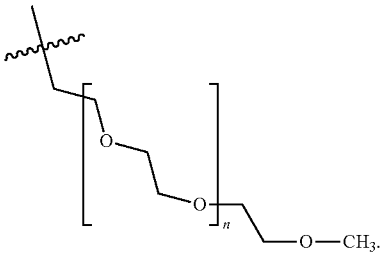

In some embodiments, n is an integer from 1 to 1,000, from 1 to 800, from 1 to 300, or from 1 to 100. In some embodiments, n is selected from 10, 20, 50, 100, 200, 250, 300, 500, 600, and 1000.

In some embodiments, the ligand moiety T is an anchoring moiety. In these embodiments, the ligand has affinity to the material of the core of the particle described herein. For example, the ligand is a hydrophobic tail, and the core of the particle consists of or comprises a hydrophobic polymer or co-polymer. In this example, the ligand and the particle core interact through hydrophobic interaction and Van der Waals forces, and the compound of Formula (I), therefore, is retained in the hydrophobic core of the particle.

In some embodiments, group T is a lipophilic moiety. Suitable examples of lipophilic moieties include $C_nH_{2n-1}$ alkyl chains where n is 8-22 (e.g., $C_{8-22}$ alkyl chain, such as $C_8$, $C_{10}$, $C_{11}$, $C_{14}$, $C_{16}$, or $C_{18}$ group), fatty acids and glycerides, and phospholipids. Examples of fatty acids include saturated and unsaturated fatty acids, such as linolenic acid, linoleic acid, myristic acid, stearic acid, palmitic acid, eicosanoic acid, and margaric acid. Examples of fatty glycerides and phospholipids include 1,2-dipalmitoyl-sn-glycero-3-phosphoethanolamine, 1,2-dioleoyl-sn-glycero-3-phosphoethanolamine, 1,2-dimyristoyl-sn-glycero-3-phosphoethanolamine, and 1,2-distearoyl-sn-glycero-3-phosphoethanolamine. Other examples of lipophilic moieties include monoglycerides and diglycerides, such as monolaurin, glycerol monostearate, glyceryl hydroxystearate, stearoyl lactylate and related moieties.

In some embodiments, T is a 16-carbon aliphatic chain that provides hydrophobicity to efficiently encapsulate the compound of Formula (I) into the hydrophobic core of a material such as a polymeric nanoparticle prepared from PLGA-PEG (poly lactic co-glycolic acid, polyethylene glycol block copolymer).

T may be terminated by reactive groups for covalently linking the prodrug to another substance, such as a nanoparticulate or material vehicle; such as a targeting ligand including an antibody, protein fragment, small molecule or other, with affinity for a particular tissue or protein or cell-type or other substance. T may be more hydrophilic than the 16-carbon aliphatic chain, for instance to tune the release rate of a non-covalently material-encapsulated prodrug from said material. More hydrophilic materials can include aliphatic chains of shortened length (fewer carbons); polyethylene glycol; peptides; and others. T may link through covalent or non-covalent bonding to a small molecule, biologic, macromolecule, polymeric, or other structure such as with an antibody, albumin, polypeptide, carbohydrate, glycoprotein, proteoglycan, lipoprotein, lipid, liposome, synthetic polymer, natural polymer, or even cell, cell fragment, and/or tissue structure.

Trigger Sensitive Moieties (TR)

In some embodiments, TR is a trigger-sensitive group that may respond to chemical, enzymatic, catalytic, bio-orthogonal, and/or biological interaction. In some embodiments, the trigger-sensitive group TR comprises a bioorthogonal click reagent (e.g., TCO reagent such as 3-OH TCO, or azide, alkyne, or tetrazine, each of which may be linked to X through a bidentate self-immolative group, i.e., there may be a bidentate self-immolative group between $L^1$ and the bioorthogonal click-reactive moiety of TR). Trigger-sensitive groups have been combined and discussed in relation to self-immolative linkers as disclosed herein. Trigger-sensitive groups TR include disulfide bonds that reduce upon exposure to reducing conditions, for instance as may be found in cells with sufficient levels of glutathione (additional glutathione may be administered to the subject as well). Trigger-sensitive groups TR include chemically labile bonds, for instance such as acid-labile silyl ethers (Finniss et al., 2014, MedChemComm, 5, 1355-1358, which is incorporated herein by reference). Trigger-sensitive groups TR include enzymatically labile bonds, such as polypeptides and their derivatives that may be hydrolyzed by certain proteases, peptidases, and other enzymes, for instance including the protease Cathepsin B (Val-Ala and Val-Cit as trigger sensitive groups and protease substrates). Other enzymatically responsive trigger-sensitive groups TR include β-galactoside-responsive galactose substituents. Trigger-sensitive groups may also include bio-orthogonal substrates, that is, substrates that react with substances that are not naturally found at high levels in the body. These substrates include Alloc and Poc groups that are reactive with palladium and other transition metal compounds (e.g., Pd, Au, Pt, Ru); and so-called click chemistry reagents such as trans-cyclooctene (TCO) derivatives (e.g., 3-OH TCO), and related compounds that are reactive with groups such as tetrazine (Tz). As is shown in FIG. 1B, when the compound of formula (I) is reacted with the trigger catalyst (e.g., bioorthogonal catalyst), the bond between $L^1$ and X in Formula (I) is cleaved, triggering the self-immolation cascade and release of drug D.

Caged Drug Payloads (D)

In some embodiments, any small-molecule drug D may be incorporated in the compound of Formula (I) of the present disclosure. Such drugs may include compounds with known systemic toxicity or known undesired side effects that are observed when the drug is administered systemically. In some embodiments, the drug is hydrophobic (e.g., poorly water soluble drug). In some embodiments, the drug is hydrophilic (e.g., a drug having good water solubility). In some embodiments, the drug is positively charged (e.g., the drug comprises an amino group or an ammonium group). In some embodiments, the drug is negatively charged (e.g., the drug comprises COOH group, $SO_3H$ group, or $PO_3H$ group).

Small molecule drugs are low molecular weight organic compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons.

Suitable examples of drugs include anticancer agents, anti-angiogenesis agents, anti-inflammatory agents, steroid drugs, antibiotics, antivirals, anti-thrombotics, antifungals, and other therapeutic agents meeting the criteria set forth above, or a pharmaceutically acceptable salt thereof.

Suitable examples of anticancer agents include antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), and anti-mitotic agents (e.g., vincristine, vinblastine, paclitaxel, and maytansinoids).

Other examples of suitable chemotherapeutic agents include any of: monomethyl auristatin E (MMAE), abarelix, aldesleukin, alitretinoin, allopurinol, altretamine, anastrozole, arsenic trioxide, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, meclorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof.

Other suitable examples of drugs include antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, resiquimod, imiquimod, teriflunomide, and dimethyl fumarate), and steroid hormones (e.g., dihydrotestosterone and estradiol).

Additional examples include pain relief agents (e.g., a nonsteroidal anti-inflammatory drug such as celecoxib or rofecoxib), antinausea agents, cardioprotective drugs (e.g., dexrazoxane, ACE-inhibitors, diuretics, cardiac glycosides), cholesterol lowering drugs, revascularization drugs, beta-blockers (e.g., acebutolol, atenolol, bisoprolol, metoprolol, nadolol, nebivolol, or propranolol), and angiotensin receptor blockers (also called ARBs or angiotensin II inhibitors) (e.g., azilsartan, candesartan, eprosartan, irbesartan, losartan, olmesartan, telmisartan, or valsartan).

Some other examples of the drug include a reporter, imaging, and/or radionuclide agent. Examples that have been synthesized and reported here include 4-methyl-7-aminocoumarin (AMC), which exhibits fluorescence upon triggered release from the prodrug scaffold. In this case "imaging" can refer to generation of distinguishing contrast detectable by a measurement, such as an optical signal (for instance here in the case of fluorescent AMC) but also including an not limited to positron and photon emission, ultrasound contrast, magnetic signal, or other.

Particles

This disclosure also provides particles and encapsulated particulate formulations of the compounds of Formula (I), or a pharmaceutically acceptable salt thereof. That is, the present disclosure provides particles that comprise the compound of Formula (I), or a pharmaceutically acceptable salt thereof, in their core (i.e., the compound is encapsulated within the particle).

Particles may be microparticles or nanoparticles. Nanoparticles are preferred for intertissue application, penetration of cells, and certain routes of administration. The nanoparticles may have any desired size for the intended use. The nanoparticles may have any diameter from 10 nm to 1,000 nm. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 50 nm to 350 nm, from 50 nm to 300 nm, or from 50 nm to 200 nm. In preferred embodiments the nanoparticles can have a diameter less than 400 nm, less than 300 nm, or less than 200 nm. The preferred range is between 50 nm and 300 nm.

Nanoparticles can be polymeric particles, non-polymeric particles (e.g., a metal particle, quantum dot, ceramic, inorganic material, bone, etc.), liposomes, micelles, polymeric micelles, viral particles, hybrids thereof, and/or combinations thereof. In some embodiments, the nanoparticles are, but not limited to, one or a plurality of lipid-based nanoparticles, polymeric nanoparticles, metallic nanoparticles, surfactant-based emulsions, dendrimers, buckyballs, nanowires, virus-like particles, peptide or protein-based particles (such as albumin nanoparticles) and/or nanoparticles that are developed using a combination of nanomaterials such as lipid-polymer nanoparticles. In some embodiments, nanoparticles can comprise one or more polymers or co-polymers.

Nanoparticles may be a variety of different shapes, including but not limited to spheroidal, cubic, pyramidal, oblong, cylindrical, toroidal, and the like. Nanoparticles can comprise one or more surfaces.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties. For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition. In this regard, see, e.g., WO 2007/150030, which is incorporated herein by reference in its entirety.

In some embodiments, the delivery vehicle is a particle (e.g., a nanoparticle) comprising a water-insoluble polymeric core and hydrophilic shell. In these embodiments, the compounds of Formula (I) are embedded in the hydrophobic core. In some examples, the particles are prepared from an amphiphilic material (e.g., a polymer that contains both lipophilic and hydrophilic properties in the same molecule). In these examples, the particles self-assemble such that the hydrophobic part of the amphiphilic material becomes the core of the particle and the hydrophilic material becomes the shell of the particle. Referring to FIG. 1A, the figure shows an exemplary compound of Formula (I) encapsulated in the core of the PLGA-PEG nanoparticle 100. In this figure, the core 110 is composed of PLGA and the shell 112 is composed of PEG. In some embodiments, the delivery vehicle is a particle (e.g., a nanoparticle) comprises only a water-insoluble polymeric material, and does not have any hydrophilic shell. In these embodiments, the water-insoluble polymeric material constitutes the entire particle (i.e., the shell 112 is lacking in the particle 100).

In some embodiments, the hydrophobic polymeric material is selected from polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienyl-methylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, aminoalkyl(meth)acrylamides), styrenes, and lactic acids. A copolymer of lactic acid and glycolic acid can comprise a range of ratios of lactic acid to glycolic acid monomers, for example, from about 1:9 to about 9:1, from about 1:4 to about 4:1, from about 3:7 to about 7:3, or from about 3:2 to about 2:3. In some embodiments, the ratio of lactic acid to glycolic acid monomers can be about 1:9; about 1:8; about 1:7; about 1:6; about 1:5; about 1:4; about 3:7; about 2:3; about 1:1; about 3:2; about 7:3; about 4:1; about 5:1; about 6:1; about 7:1; about 8:1; or about 9:1.

In some embodiments, In some embodiments, the amphipathic polymer contains poly(ethylene glycol)-co-poly(D,L-lactic acid) (PLA-PEG), poly(ethylene glycol)-co-(poly(lactide-co-glycolide)) (PLGA-PEG) (e.g., the amphipathic polymer is PLGA-PEG), polystyrene-b-polyethylene oxide, polybutylacrylate-b-polyacrylic acid, or polybutylmethacrylate-b-polyethyleneoxide. Additional examples of amphipathic copolymers are described in U.S. Patent Application Publication No. 2004/0091546 (incorporated herein by reference in its entirety). Additional examples of amphipathic polymers (e.g., amphipathic copolymers) are known in the art.

Encapsulation of the compound of Formula (I) in the core of the particle supports extended pharmacokinetics of the prodrug (extended circulation, tunable drug release) and enhanced accumulation in, e.g., tumor tissue (or any other targeted tissue) via enhanced permeability and retention effects (including via macrophages and amplified through local radiation).

Many other materials can be used for making of the particle. These materials consist of polymers or co-polymers that self-assemble into nanoparticles with hydrophobic cores that non-covalently interact with the hydrophobic components of the prodrug that uses an aliphatic group as T. The polymers used in the present disclosure are a mixture of PLGA (poly(lactic-co-glycolic acid)) and PLGA-PEG block co-polymer. However many other types of materials (polymers, proteins, others) could be used, for either nano particulate encapsulation, non-covalent encapsulation in a larger-scale material such as an implantable hydrogel, and covalent incorporation into a material. In the present demonstrations, PLGA-PEG nanoformulations were used for controlled and optimized drug release, biodegradability and known properties of efficient accumulation in tumors, and efficient prodrug encapsulation. The present data shows how properties of the prodrug design (e.g., adding the $C_{16}$ aliphatic chain) can tune release rates of the prodrug from the nanoparticle vehicle. Shorter chain lengths (and lack of aliphatic chain altogether) lead to faster release rates. Covalent attachment of the side chain to the polymer itself, for instance with a stable or environmentally sensitive coupling (an example of the latter being an acid-labile bond) can further tune the release rate of the prodrug from the polymeric vehicle Trigger Catalysts The compound of Formula (I) may be administered to a subject in combination with an immolation cascade trigger catalyst. The catalyst may be administered in the catalytic amount (there is no requirement of stoichiometric amount of the compound of Formula (I) and the trigger reagent). The trigger reagent is complementary to the trigger-sensitive moiety. For example, if the trigger sensitive moiety is allyloxycarbonyl (alloc) group (as is shown, e.g., in FIG. 1A), then the trigger catalyst is a transition metal reagent (e.g., any one of the transition metal reagents shown in FIG. 26), or a nanoparticle comprising same. In another example, the trigger sensitive group is 3-OH TCO, and the trigger reagent is a tetrazine-containing reagent. In some embodiments, the TR group/trigger catalyst couple is any one of the dissociative bioorthogonal reaction participants described in ChemBioChem 2019, 20, 1615-1627, which is incorporated herein by reference in its entirety. The trigger catalyst may be an enzyme, such as protease Cathepsin B or b-galactoside. In case of the metal trigger (e.g., Pd), the catalyst may be administered to the subject as a neat metal nanoparticle, or the metal reagents (e.g., FIG. 26) may be incorporated into the PLGA-PEG nanoparticle as shown, for example, in FIG. 1B (Pd NP).

The trigger catalyst may accumulate in the target cells and tissues (e.g., cancer cells or tissues, or heart, or injury site) selectively. This may be accomplished, for example, by site-specific delivery of the trigger catalyst (trigger reagent). The trigger reagent may be injected into the target tissue (e.g., intratumoral delivery). In other embodiments, the trigger may be used in a coating of a medical device such as a stent, a mesh, or an orthopedic implant. The reagent (e.g., Pd NP) may be implanted to the patient, e.g., subcutaneously. In some embodiments, the trigger reagent may be labeled with a targeting ligand that ensures cell or tissue-selective delivery of the trigger reagent to the target tissue (e.g., where the treatment of the disease is desired). For example, the trigger reagent may be labeled (e.g., covalently or non-covalently) with a tumor specific receptor or an antibody. Suitable examples of targeting ligands include RGD peptide, anti-EGFR antibody, Pembrolizumab, anti-CD4, Rituximab, Trastuzumab, Alemtuzumab, Cetuximab, Panitumumab, Bevacizumab, Ipilimumab. A tetrazine reagent, for example, can be coupled to a cancer-targeting antibody using NHS chemistry or any other suitable means. Similarly, a Pd-NP may may attached to the cancer-targeting antibody or another targeting reagent.

The compound of Formula (I) also could be attached to the surface of a cell, in situ within the body for instance by attaching it to an antibody that targets immune or other cells (e.g., prodrug-anti-CD4 injected, which would bind to CD4+ T-cells). The prodrug could be attached to cells in vitro using the same targeting strategy (prodrug-antibody added to cells in vitro, which then may be adoptively transferred for therapy), or attached to the surface of the cell (approaches described extensively in DOI: 10.1186/s13036-018-0123-6, which is incorporated by reference) similar to as described for "cytokine backpacks" and similar technology, for instance as developed by Darrell Irvine et al. and Torque therapeutics, which are incorporated by reference. The type of cell could be any used for both in vitro or in vivo, could include microbes as with microbiome engineering, could be immune cell, stem cell, mesenchymal stromal cell.

The palladium complex or palladium particles could be delivered to cells that would then be adoptively transferred (therefore to make something like a "catalytically active cell") by similarly conjugating particles to the cell surface, or alternatively by allowing cells to take up and internalize particles. The prodrug would also be internalized in these cells (or be permeable to their membranes) and react with the palladium or other trigger than had been delivered.

Pharmaceutical Compositions and Formulations

The present application also provides pharmaceutical compositions comprising an effective amount of an active ingredient as disclosed herein, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

Pharmaceutically Acceptable Salts

In some embodiments, a salt of any one of the compounds described herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of the present disclosure include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of the present disclosure include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Dosages and Regimens

Any of the compositions of the present disclosure contain the active ingredient (e.g., prodrug or drug) in an effective amount (e.g., a therapeutically effective amount). Effective doses (e.g., therapeutically effective doses) may vary, depending on the diseases treated, the severity of the disease, the route of administration, the sex, age and general health condition of the subject, excipient usage, the possibility of co-usage with other therapeutic treatments such as use of other agents and the judgment of the treating physician (e.g., oncologist).

In some embodiments, an effective amount (e.g., therapeutically effective amount) of any one of the active ingredients of the present application, or a pharmaceutically acceptable salt thereof, can range, for example, from about from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

In the methods of treating or preventing any one of the disease or conditions described here, the prodrug conjugate (e.g., in a nanoparticle) and activating agent (e.g., Pd-NP) may be administered to the subject simultaneously (e.g., in the same dosage form or in separate dosage forms), or consecutively (e.g., before or after one another, in separate dosage forms).

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "carboxy" refers to a —C(O)OH group.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl. The term "arylene" refers to a divalent aryl group, such as a phenylene.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl. The term "cycloalkylene" refers to a divalent cycloalkyl group, such as cyclopropylene.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, N═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

The terms "inhibit" and "reduce" means to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The term "Encapsulation efficiency" (EE) as used herein is the ratio of the amount of drug that is encapsulated by the particles (e.g., nanoparticles) to the initial amount of drug used in preparation of the particle.

The term "Loading capacity" (LC) or "loading efficiency" (LE) as used herein is the mass fraction of drug that is encapsulated to the total mass of the particles (e.g., nanoparticles).

A "polymer," as used herein, is given its ordinary meaning as used in the art, i.e., a molecular structure including one or more repeat units (monomers), connected by covalent bonds. The polymer may be a copolymer. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks.

A "copolymer" herein refers to more than one type of repeat unit present within the polymer defined below.

A "particle" refers to any entity having a diameter of less than 10 microns (μm). Typically, particles have a longest dimension (e.g., diameter) of 1000 nm or less. In some embodiments, particles have a diameter of 300 nm or less. Particles include microparticles, nanoparticles, and picoparticles. In some embodiments, particles can be a polymeric particle, non-polymeric particle (e.g., a metal particle, quantum dot, ceramic, inorganic material, bone, etc.), liposomes, micelles, hybrids thereof, and/or combinations thereof. As used herein, the term "nanoparticle" refers to any particle having a diameter of less than 1000 nm. In preferred embodiments, a nanoparticle is a polymeric particle that can be formed using a solvent emulsion, spray drying, or precipitation in bulk or microfluids, wherein the solvent is removed to no more than an insignificant residue, leaving a solid (which may, or may not, be hollow or have a liquid filled interior) polymeric particle, unlike a micelle whose form is dependent upon being present in an aqueous solution.

The term "particle size" (or "nanoparticle size" or "microparticle size") as used herein refers to the median size in a distribution of nanoparticles or microparticles. The median size is determined from the average linear dimension of individual nanoparticles, for example, the diameter of a spherical nanoparticle. Size may be determined by any number of methods in the art, including dynamic light scattering (DLS) and transmission electron microscopy (TEM) techniques.

Examples

MATERIALS AND METHODS

Synthesis—General

Unless otherwise noted, reactions were carried out under an atmosphere of nitrogen or argon in air-dried glassware with magnetic stirring. Air- and/or moisture-sensitive liquids were transferred via syringe. All reagents were obtained from commercial sources and used without further purification. $dPEG_4$-$NH_2$ (Amino-dPEG®4-OH) was obtained from Quanta BioDesign (OH, USA). Doxorubicin was obtained from LC Laboratories (MA, USA) and MMAE was obtained from AK Scientific (CA, USA). Dry solvents were obtained from Sigma Aldrich. Analytical thin layer chromatography (TLC) was performed using plates cut from glass sheets (silica gel 60 F-254, Silicycle). Visualization was achieved under a 254 nm or 365 nm UV light and by immersion in a solution of cerium sulfate in ethanol followed by heating with a heat gun. Column chromatography was carried out using silica gel G-25 (40-63 μM) or C18 flash cartridges (SNAP C18 and SNAP C18 Ultra, Biotage). NMR spectra were recorded on a Bruker Avance IIIHD 600 MHz spectrometer equipped with a Prodigy BBO cryo probe, or on a Bruker Avance UltraShield 400 MHz spectrometer. Chemical shifts are reported in parts per million (6) and calibrated using residual undeuterated solvent. Data are represented as follows: Chemical shift, multiplicity (s=singlet, d=doublet, t=triplet, q=quartet, p=pentet, m=multiplet, b=broad), coupling constant (J, Hz) and integration. High performance liquid chromatography-mass spectrometry analysis (HPLC-MS, LCMS) was performed on a Waters instrument equipped with a Waters 2424 ELS Detector, Waters 2998 UV-Vis Diode array Detector, Waters 2475 Multi-wavelength Fluorescence Detector, and a Waters 3100 Mass Detector. Separations employed an HPLC-grade water/acetonitrile solvent gradient. Columns: XTerra MS C18 Column, 125, 5 μm, 4.6 mm×50 mm column; Waters XBridge Protein BEH C4 Column, 300, 3.5 μm, 2.1 mm×50 mm. Routine analysis were conducted with 0.1% formic acid added to both solvents.

Reaction kinetics and catalyst performance. Alloc-SIL-dPEG4-AMC (8) was reacted at a concentration of 5 μM with palladium catalyst (Pd-1, Pd-2, Pd-3, Pd-4) at a concentration of 10 μM in HBSS and MEM (see FIG. 8). Alloc2R110 was reacted at a concentration of 5 μM with Pd-1 at a concentration of 10 μM in HBSS as described previously.2 Fluorescence was monitored for 10 h at room temperature using 96 well plates and a Tecan Safire 2 fluorescence plate reader.

Fluorescence spectra. Fluorescence spectra (see FIG. 8) were recorded on an LS55 fluorimeter (PerkinElmer Inc., MA, USA) at a concentration of 1 μM 7-amino-4-methylcoumarin (AMC) or Alloc-SIL-dPEG4-AMC (8) in PBS, and after reacting Alloc-SIL-dPEG4-AMC (8) (1 μM in PBS) with Pd-1 (2 μM in PBS).

Cell lines and animal models: All animal research was performed in accordance with guidelines from the Institutional Subcommittee on Research Animal Care. HT1080 xenografts were generated by 2 million cells implanted subcutaneously in flanks of 6-8 week old female nu/nu mice (Cox7/MGH) in 50 μl PBS. MC38 syngeneic tumors were formed by intradermal implantation of 2 million cells in 50 μl PBS, in the flanks of 7-12 week old female C57BL/6 mice (JAX), following previously described inoculation protocols.[33] Four blinded caliper measurements per tumor were used to measure tumor size according to the formula $V=(width)^2(length)/2$; animals were randomly assigned to treatment groups. Experiments build on prior imaging, biodistribution, and longitudinal tumor growth data that likewise guided determination of experimental sample sizes.[5, 30] Treatment began approximately 3 weeks post-implantation once tumors reached an average diameter of 5.5±1.8 mm in the HT1080 model (mean±std. dev.; n=72), and roughly 2 weeks post-implantation in the MC38 model once tumors reached an average diameter of 5.45±1.2 mm (mean±std. dev.; n=14). Study results were pooled across independent cohorts (n≥2), therefore sample sizes of some control groups are over-represented. Drug free NP vehicle controls were used throughout, and nanoformulations were freshly prepared prior to injection. Treatments were 0.8 μmol $kg^{-1}$ $C_{16}$proMMAE, 50 mg $kg^{-1}$ Pd-NP, or the combination of the two staggered by 5 h on the same day, all by tail-vein injection in 50 μl PBS, on the indicated days. Following pre-established criteria, mice were sacrificed when tumor burden reached more than 1 cm in diameter, or 2 cm in diameter if only one tumor was present, or according to a body condition score of 2. Drug-induced weight loss did not exceed 10% in any treatment group. Blood chemistry readouts were measured from plasma collected in heparinized tubes by terminal cardiac puncture under vaporized isoflurane anesthesia, using the MGH Veterinary Clinical Pathology lab and the automated DriChem blood chemistry analyzer (Heska). The HT1080 cell line was obtained directly from ATCC, was cultured according to the provider's guidelines, was not independently verified, and underwent routine mycoplasma testing. Transgenic cell lines were generated as described previously.[5] EB3-mApple cells were generated by transfection and repeated rounds of sorting by FACS. The construct mApple-EB3-7 was a gift from Michael Davidson (Addgene plasmid #54892). For all procedures, mice were anesthetized with an isoflurane vaporizer on a heated stage; euthanasia was performed by $CO_2$ chamber when necessary, and all treatment groups underwent procedures and monitoring consecutively on the same day when possible, but in a randomized order.

Nanoformulation and characterization: $C_{16}$proMMAE and $C_{16}$proDOX nanoformulations were synthesized by nano-precipitation by first combining 0.1 mg prodrug, 5 mg PLGA (75:25 lactide:glycolide)$_{8.3\ kDa}$-PEG5.5 kDa (Advanced Polymer Materials, Inc.; by manufacturer, 70% functionality by $^1H$ NMR, PI 1.38 according to GPC), and 1 mg PLGA (50:50 lactide:glycolide)$_{30\text{-}60\ kDa}$ (Sigma) in a 212 μl mixture of 1:1 dimethylformamide (DMF):acetonitrile (MeCN), then added drop-wise to 20 mL $H_2O$ under stirring at r.t. for 4 h, then filtered through a 0.45 μm cellulose acetate syringe filter (Cole-Parmer), and concentrated in Amicon 100 kDa molecular-weight-cutoff centrifugal filters (Millipore) spun at 3000×g for 30 min. Initial experiments determined up to 1 mg of $C_{16}$ prodrug could be used with the same polymer composition with no detectable loss in loading efficiency. For fluorescence-based imaging and flow-cytometric detection of NP uptake, PLGA-BODIPY630 was used instead of PLGA (described previously).[5] NP drug and Pd compound loadings were determined by absorbance (Nanodrop spectrophotometer), interpolation from a standard curve ($R^2>0.99$) after 1:10 dilution in DMF. Size and zeta potential measurements were performed using dynamic light scattering (Malvern Zetasizer). Prodrug loading efficiency is defined as the fraction of initial drug used in the nano-precipitation reaction that was successfully encapsulated and recovered in final NP product.

Transmission electron microscopy (TEM) was performed in the Microscopy Core of the Center for Systems Biology/Program in Membrane Biology (MGH). A JEOL 1011 electron microscope was used for TEM, with sample preparation by deposition of 20 μl NP (1.0 mg ml-1) onto a carbon coated copper grid. Excess solution was blotted, grids were stained with phosphotungstic acid, and then blotted, dried and imaged. In vitro NP prodrug release was performed by incubating in PBS at 37° C., separating NPs using a 30 kDa molecular weight cutoff filter (Millipore Amicon) after 72 h, and measuring flow-through for drug content by absorbance (Nanodrop). NP was dissolved in DMF and also measured for drug content by absorbance. Pd-NP, $Alloc_2R110$ and its nanoformulation, and all Pd compounds were synthesized and characterized as previously described.[5]

In vitro NP characterization: 5,000 cells per well were added to 96-well plates for cytotoxicity assessment; cells were treated after overnight seeding with compound or the appropriate buffer control (drug-free PLGA-PEG NP), and assessed for viability 72 h later using PrestoBlue (Life Technologies) following the manufacturer's protocol.

For in vitro $C_{16}$proDOX and DOX quantification, 15 cm confluent plates of HT1080 cells were washed 3× in PBS, lysed using 100 μl lysis buffer (150 mM NaCl, 1% Triton X-100, 50 mM Tris, Roche cOmplete protease inhibitor, pH 8.0), and drug was extracted as described.34 Concentrations were fit from integrated fluorescence chromatography as before, using linear approximation as deemed appropriate from reference standards of purified DOX and $C_{16}$ solutions, correcting for fluorescence efficiencies between $C_{16}$proDOX and DOX.[5] Cells were treated with 1 μM DOX or $C_{16}$proDOX and/or 70 μM Pd-NP for 24 h. $C_{16}$proMMAE activation was detected by incubation of 20 μM $C_{16}$proMMAE with 60 μM Pd-NP in DMF for 24 h at 37° C.

Microtubule imaging. EB3 tracking was performed using an FV1000 confocal laser scanning microscope on a 37° C. heated stage, with XLUMPLFLN 20× (NA 1.0) or LUMFLN 60× (NA 1.1) water-immersion objectives, 1-10× digital zoom, 559-nm diode laser, and BA575-620 emission filter (all Olympus America). Cells were treated with 1 μM MMAE, $C_{16}$proMMAE, and/or 35 μM Pd-NP for 24 h prior to imaging. EB3 tracks were automatically identified and analyzed from time-lapse datasets using u-track software,[35] with tuning of maximum gap number and minimum frame number across datasets to account for differences in image quality; ambiguous and spurious tracks and artifacts were excluded according to requirements for directional continuity (directional persistence as net displacement/path length>0.8) and movement (value>3 pixels). Speed was determined between frames in each track and averaged for each track by computing the mean of the middle 80% of between-frame values. Track overlay figures were produced using a custom python script. Averaged track speeds excluded outliers falling more than 1.5× the interquartile range for each biological replicate.

In vitro NP uptake imaging. To quantify subcellular localization of NPs in HT1080 cells, Rab7a-RFP and Lamp1-RFP fusion constructs were expressed using a commercial baculovirus platform (CellLight BacMam 2.0, Invitrogen), following manufacturing guidelines. Pharmacological modulation of NP uptake was performed using the following: staurosporine (1 μM; LC labs), latrunculin B (1 μM; Tocris), cytochalasin D (1 μM; Sigma), chloroquine (50

μM; Sigma), and ethylisopropyl amiloride EIPA (100 μM; Tocris). Cells were rinsed in fresh media immediately prior to imaging; only adherent cells were quantified. Chloroquine dose-response measurements were normalized to the $C_{16}$proDOX control (rather than the chloroquine-free control), in order to compare relative effects on the potency of Pd-mediated $C_{16}$proDOX activation itself 50 μM chloroquine alone caused a 15-30% decrease in cell viability.

Flow cytometry and confocal tumor imaging: Subcutaneous HT1080 tumors were harvested 3 weeks post-implantation and 24 h post-treatment with 3 mg $kg^{-1}$ PLGA-PEG therapeutic NPs[14] encapsulated with PLGA-BODIPY630 as a validated near-infrared label of NP uptake, administered by tail-vein injection in 50 μl PBS. Flow cytometry and confocal imaging are described previously.[30] Single-cell quantification of NP uptake was performed in bilateral subcutaneous tumors, matched such that one tumor received 5 Gy local gamma irradiation 72 h prior to NP administration. Following animal sacrifice at 24 h post-injection, single-cell suspensions of resected tumors were stained for tumor cells (CD45− hCD29+) using CD45 (BD 30-F11) and hCD29 (BD MAR4) antibodies, and single-cell NP uptake was measured by the mean fluorescence intensity of gated cells on an LSRII flow cytometer. Confocal tumor imaging was performed on mice bearing subcutaneous HT1080 tumors under a dorsal window chamber as previously described;[36] tumor cells were subcutaneously injected 30 min after surgical chamber implantation, and imaged and irradiated 2 weeks later.

Radiation Therapy: Dual source $^{137}Cs$ Gammacell 40 Exactor (Best Theratronics) with a custom-built lead shield was used for conformal tumor irradiation, using a setup described previously.[30] Immediately prior to RT, mice were anesthetized via 87.5 mg/kg ketamine and 12.5 mg/kg xylazine i.p., immobilized in the lead shielding chamber, and irradiated individually according to the calibrated dose rate of 0.6 Gy $min^{-1}$.

Biodistribution: Accumulation of palladium and prodrug NP in tissues was assessed as previously described, shown here as a combined ratiometric analysis presented relative to tumor concentrations. All measurements were determined 24 h post-treatment with Pd-NP in HT1080 subcutaneous tumor-bearing mice, as used throughout. Palladium biodistribution was determined by an Agilant 7500 Series ICP-MS, fitting to a 9-point standard curve and using Pd ICP standard solution. Biodistribution of prodrug NP vehicle and activation was quantified by Olympus OV110 fluorescence reflectance imaging of freshly excised tissue that had been rinsed in PBS. For a model prodrug NP, PLGA-PEG nanoformulation encapsulating the near infrared NP label PLGA-BODIPY630 and the model Pd-NP substrate $Alloc_2R110$ were used, all as described and characterized previously.[5] Fluorescence intensity values were calculated from regions of interest defined manually in ImageJ, after correcting for background autofluorescence. Measurements were averaged according to the mean across n=3 replicates, and calculated concentrations were divided by the average concentrations observed in the tumor. To compare tumor levels to concentrations seen in clearance organs, tumor levels were divided by the pooled average concentrations observed across the liver, spleen, and kidney.

Computational pharmacokinetic modeling. The multi-compartment model was developed based on custom Matlab scripts and was simulated using the ordinary differential equation solver ode15s. Parameters were optimizing according to iterative and stochastically-sampled rounds of bounded optimization. The cost function consisted of experimentally measured features of biodistribution and pharmacokinetics (Table S3), and n=24 optimization runs were computed based on stochastic initial parameter values and cost functions with slightly different weights on each of these features. Average modeling results were then tabulated from the 24 optimizations. The final model was generated after iterative rounds of increasing the model complexity and compartments (e.g., through the use of saturable phagocytic uptake) to better fit the experimental data, until yielding sufficiently accurate results.

Statistical analysis: Statistical analyses were performed using Prism (GraphPad), MATLAB (Mathworks), and Excel (Microsoft). Measurement statistics and error bars are described in figure legends. Two-tailed tests were used with false-positive thresholds of α=0.05.

Example 1—Synthesis of Alloc-Protected Self-Immolative Linker (Alloc-SIL) (See FIG. 23)

The synthesis of intermediate 5 was conducted according to Venkatesan et al. (see reference 37).

2

(2)

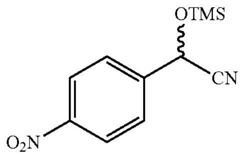

(±)-2-(4-Nitrophenyl)-2-((trimethylsilyl)oxy)acetonitrile

To a solution of 4-nitrobenzaldehyde (1) (5 g, 33 mmol) in dichloromethane (50 mL) was added zinc iodide (1.05 g, 3.3 mmol) and trimethylsilyl cyanide (TMS-CN) (4.56 g, 46 mmol). The mixture was heated to reflux for 4 h. After addition of 1M HCl (30 mL) heating was continued at 60° C. for 4 h. The reaction mixture was cooled to room temperature, diluted with water (50 mL) and extracted with dichloromethane (3×100 mL). The combined organic layer was washed with water (200 mL) and brine (200 mL), dried over $Na_2SO_4$ and concentrated. The crude product was used without further purification.

(3)

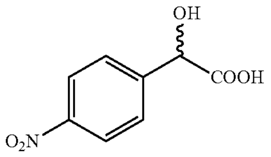

(±)-2-Hydroxy-2-(4-nitrophenyl) acetic acid

To a solution of crude 2 in acetic acid (40 mL) was added 10M HCl (40 mL) and the mixture was heated to 100° C. for 6 h. After cooling to room temperature, the mixture was concentrated and dried at reduced pressure. The obtained crude product was used without further purification.

(4)

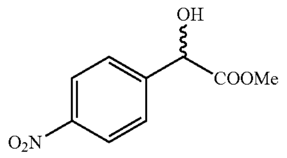

(±)-Methyl 2-hydroxy-2-(4-nitrophenyl)acetate

Crude 3 was dissolved in methanol (50 mL) and $H_2SO_4$ (4 mL) was added. The solution was refluxed for 8 h, then cooled to room temperature and concentrated under reduced pressure. The residue was dissolved in EtOAc (100 mL), washed with water (100 mL) and brine (100 mL), and dried over $Na_2SO_4$. The solvent was evaporated and the residue was purified by column chromatography (200 g $SiO_2$, EtOAc in hexanes, gradient elution) to obtain 4 (4.11 g, 59% over 3 steps). Analytical data matched those reported in the literature.

(5)

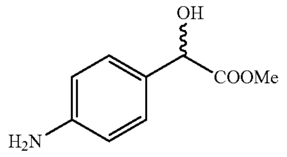

(±)-Methyl 2-(4-aminophenyl)-2-hydroxyacetate

Palladium on activated charcoal (10% Pd/C, 1 g) was added to a solution of 4 (4 g, 19 mmol) in methanol (50 mL). The flask was flushed with $H_2$ and the mixture was stirred under a positive pressure of $H_2$ (balloon) for 18 h. The mixture was filtrated over Celite® and concentrated under reduced pressure to obtain compound 5 (3.42 g, quant.). Analytical data matched those reported in the literature.

(6)

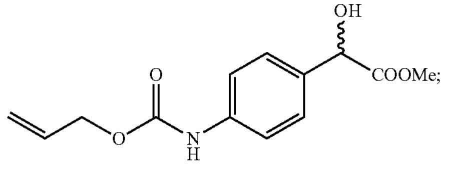

Alloc-SIL (±)-methyl 2-(4-(((allyloxy)carbonyl)amino)phenyl)-2-hydroxyacetate

To a solution of 5 (362.4 mg, 2 mmol) and pyridine (322 μL, 4 mmol) in dichloromethane (10 mL) was slowly added a solution of Alloc-Cl (301.3 mg, 2.5 mmol) in dichloromethane (3 mL). The mixture was stirred at room temperature for 12 h, then diluted with dichloromethane (20 mL), washed with water (20 mL) and brine (20 mL), dried over $Na_2SO_4$, and concentrated. The residue was purified by column chromatography (40 g $SiO_2$, EtOAc in hexanes, gradient elution) to obtain Alloc-SIL (6) as a white powder (472 mg, 89%); $^1$H NMR (400 MHz, CDCl3) δ 7.41-7.32 (m, 4H), 6.72 (bs, 1H), 5.96 (ddt, J=17.1, 10.6, 5.7 Hz, 1H), 5.36 (dq, J=17.1, 1.4 Hz, 1H), 5.26 (dq, J=10.6, 1.3 Hz, 1H), 5.14 (s, 1H), 4.66 (dt, J=5.7, 1.3 Hz, 2H), 3.75 (s, 3H), 3.42 (bs, 1H); $^{13}$C NMR (100 MHz, $CDCl_3$) δ 174.1, 153.1, 138.1, 133.3, 132.3, 127.4, 118.8, 118.4, 72.4, 66.0, 53.1; HRMS $[M+H]^+$ calcd. 266.1023 for $C_{13}H_{16}NO_5^+$, found 266.1020.

Example 2—Synthesis of Fluorogenic Alloc-SIL-dPEG4-AMC (See FIG. 24)

(7)

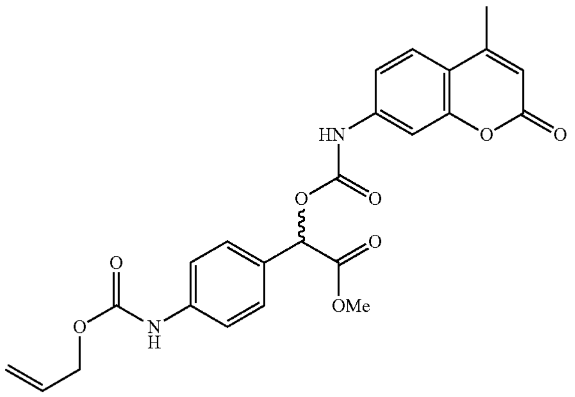

Alloc-SIL-AMC

7-Amino-4-methylcoumarin (AMC) (105.1 mg, 0.6 mmol) and triphosgene (89 mg, 0.3 mmol) were suspended in 10 mL dry toluene (10 mL) and the mixture was refluxed for 4 h. Argon was passed through the mixture for 10 min. After concentration a white solid was obtained that was reacted with Alloc-SIL (6) (155 mg, 0.58 mmol) and DIPEA (522 μL, 3 mmol) in dry THF (10 mL) at room temperature for 18 h. The mixture was concentrated and the residue was purified by column chromatography (Biotage SNAP Ultra C18 column, 30 g, $H_2O$/acetonitrile gradient elution, 0.1% formic acid) to obtain Alloc-SIL-AMC (7) (143 mg, 51%); $^1$H NMR (400 MHz, DMSO-$d_6$) δ 10.55 (s, 1H), 9.90 (s, 1H), 7.71 (d, J=8.9 Hz, 1H), 7.57-7.51 (m, 3H), 7.47-7.41 (m, 3H), 6.25 (d, J=1.1 Hz, 1H), 5.99 (ddt, J=17.2, 10.6, 5.3 Hz, 1H), 5.98 (s, 1H), 5.37 (dq, J=17.2, 1.5 Hz, 1H), 5.25 (dq, J=10.6, 1.3 Hz, 1H), 4.62 (dt, J=5.4, 1.4 Hz, 2H), 3.71 (s, 3H), 2.39 (s, 3H); $^{13}$C NMR (100 MHz, DMSO-$d_6$) δ 169.5, 160.0, 153.8, 153.2, 153.1, 152.4, 142.2, 140.2, 133.2, 128.7, 127.4, 126.1, 118.3, 117.7, 114.7, 114.3, 112.1, 104.6, 74.1, 64.8, 52.4, 18.0; HRMS $[M+H]^+$ calcd. 467.1449 for $C_{24}H_{23}N_2O_8^+$, found 467.1442.

(8)

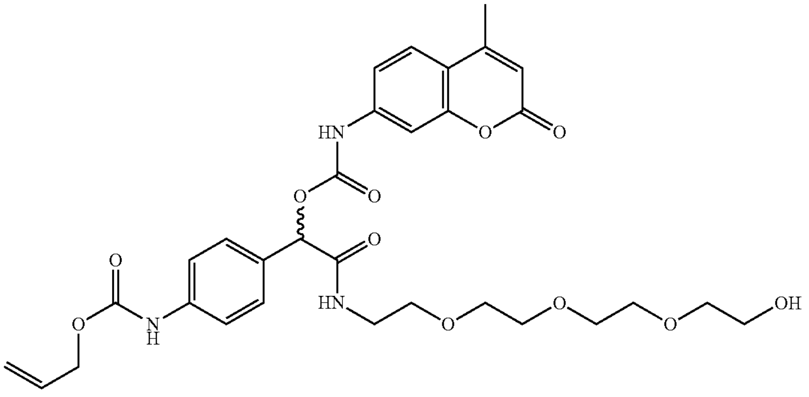

Alloc-SIL-dPEG$_4$-AMC

LiOH monohydrate (8.8 mg, 0.21 mmol) was added to a solution of Alloc-SIL-AMC (7) (32.7 mg, 0.07 mmol) in THF/$H_2O$/MeOH (6.75 mL, v/v/v=20/2/5). The solution was stirred until LCMS indicated full saponification to the respective acid (~30 min). Acidic cation exchange resin (Dowex 500X8-H, 0.5 g) was added and stirring was continued for 1 min. The resin was removed by filtration and washed with methanol. The filtrate was concentrated under reduced pressure and the residue was redissolved in dry DMF (2 mL). To the solution was added $NEt_3$ (29.3 µL, 0.21 mmol), HBTU (39.8 mg, 0.105 mmol) and dPEG$_4$-$NH_2$ (Amino-dPEG®4-OH, 27.1 mg, 0.14 mmol) and the mixture was stirred until LCMS indicated full conversion. The mixture was directly loaded onto a Biotage SNAP Ultra C18 column (30 g) and reversed phase chromatography ($H_2O$/acetonitrile gradient elution, 0.1% formic acid) afforded Alloc-SIL-AMC-dPEG$_4$ (8) (14.4 mg, 33%); $^1$H NMR (600 MHz, DMSO-d$_6$, two rotamers, ~65/35) δ 10.44 (bs, 0.65H), 10.38 (s, 0.35H), 9.84 (s, 0.65H), 9.75 (s, 0.35H), 8.39 (t, J=5.7 Hz, 1H), 7.86 (d, J=1.9 Hz, 0.35H), 7.72 (dd, J=8.7, 1.9 Hz, 0.35H), 7.70 (d, J=8.7 Hz, 1H), 7.54 (d, J=1.9 Hz, 0.65H), 7.50-7.45 (m, 1.3H), 7.45-7.40 (m, 3.35H), 6.26 (q, J=1.3 Hz, 0.35H), 6.24 (q, J=1.3 Hz, 0.65H), 6.01-5.93 (m, 1H), 5.83 (s, 0.65H), 5.36 (dq, J=17.2, 1.7 Hz, 0.65H), 5.35 (dq, J=17.2 Hz, 1.7 Hz, 0.35H), 5.25-5.21 (m, 1H), 5.08 (s, 0.35H), 4.61-4.58 (m, 2H), 3.49-3.45 (m, 7H), 3.44-3.33 (m, 7H, underneath water peak), 3.24 (q, J=5.7 Hz, 2H), 2.38 (s, 3H); $^{13}$C NMR (150 MHz, DMSO-d$_6$, two rotamers) δ 172.3, 168.4, 160.1, 153.9, 153.54, 153.28, 153.25, 153.22, 153.19, 152.4, 142.6, 142.1, 139.6, 138.7, 134.5, 133.33, 133.27, 129.7, 128.5, 127.2, 126.1, 125.8, 118.0, 117.7, 117.6, 115.8, 115.3, 114.5, 114.3, 112.4, 112.0, 106.2, 104.5, 75.0, 73.8, 72.4, 69.83, 69.77, 69.74, 69.6, 68.8, 64.8, 64.7, 60.2, 18.1, 18.0; HRMS $[M+H]^+$ calcd. 628.2501 for $C_{31}H_{38}N_3O_{11}^+$, found 628.2493.

(9)

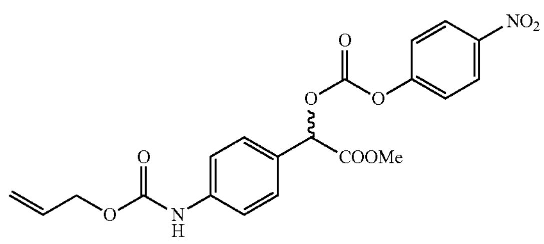

Example 3 - Alloc-SIL-C$_{16}$-drug conjugates
(See Figure 25)
Alloc-SIL-PNP

Alloc-SIL (6) (132.6 mg, 0.5 mmol) and DIPEA (130.6 µL, 0.75 mmol) were dissolved in dry DMF (2 mL). The solution was cooled to 0° C. and bis(4-nitrophenyl) carbonate (304.2 mg, 1 mmol) was added in one portion. The mixture was stirred at room temperature for 4 h, stored at −20° C. overnight, and then poured into water/EtOAc (100 mL, v/v=1/1). The layers were separated and the aqueous phase was extracted with EtOAc (2×50 mL). The combined organic layer was dried over $Na_2SO_4$ and concentrated. The residue was purified by column chromatography (40 g $SiO_2$, $Et_2O$ in hexanes, gradient elution) to afford compound 9 as a white solid (197 mg, 92%); $^1$H NMR (400 MHz, DMSO-d$_6$) δ 9.93 (s, 1H), 8.37-8.32 (m, 2H), 7.61-7.56 (m, 2H), 7.55 (d, J=8.6 Hz, 2H), 7.44 (d, J=8.6 Hz, 2H), 6.08 (s, 1H), 5.99 (ddt, J=17.2, 10.6, 5.4 Hz, 1H), 5.37 (dq, J=17.2, 1.5 Hz, 1H), 5.25 (dq, J=10.6, 1.5 Hz, 1H), 4.63 (dt, J=5.4, 1.4 Hz, 2H), 3.72 (s, 3H); $^{13}$C NMR (100 MHz, DMSO-d$_6$) δ 168.5, 154.9, 153.1, 151.3, 145.4, 140.5, 133.2, 128.7, 126.2, 125.6, 122.4, 118.3, 117.7, 77.3, 64.8, 52.8; HRMS $[M+H]^+$ calcd. 431.1085 for $C_{20}H_{19}N_2O_9^+$, found 431.1086.

(10)

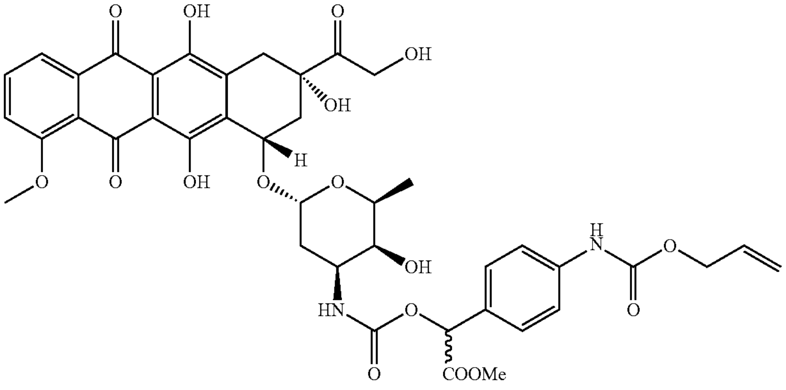

Alloc-SIL-Dox

Doxorubicin hydrochloride (174 mg, 0.3 mmol) was added to a solution of Alloc-SIL-PNP (9) (142.1 mg, 0.33 mmol) and $NEt_3$ (46 μL, 0.33 mmol) in dry DMSO (3 mL). The mixture was stirred at room temperature for 2 h (LCMS showed full conversion), then directly loaded onto a Biotage SNAP C18 column (30 g). Reversed phase chromatography ($H_2O$/acetonitrile gradient elution, 0.1% formic acid) afforded Alloc-SIL-$C_{16}$-Dox (10) (199.3 mg, 80%); $^1H$ NMR (400 MHz, DMSO-$d_6$, mixture of two diastereomers, ~1/1) δ 14.01-13.93 (m, 1H), 13.24-13.18 (m, 1H), 9.87-9.76 (m, 1H), 7.88-7.80 (m, 2H), 7.61-7.55 (m, 1H), 7.50-7.41 (m, 2H), 7.37-7.29 (m, 2H), 7.26-7.14 (m, 1H), 6.03-5.91 (m, 1H), 5.65 (s, 1H), 5.40 (d, J=8.3 Hz, 1H), 5.38-5.31 (m, 1H), 5.27-5.19 (m, 2H), 4.93-4.84 (m, 2H), 4.76-4.68 (m, 1H), 4.63-4.56 (m, 4H), 4.21-4.13 (m, 1H), 3.99-3.92 (m, 3H), 3.79-3.67 (m, 1H), 3.59 (s, 1.4H, COOMe diastereomer 1), 3.54 (s, 1.6H, COOMe diastereomer 2), 3.48-3.42 (m, 1H), 3.03-2.81 (m, 2H), 2.25-2.17 (m, 1H), 2.13-2.05 (m, 1H), 1.95-1.80 (m, 1H), 1.54-1.43 (m, 1H), 1.18-1.09 (m, 3H); $^{13}C$ NMR (100 MHz, DMSO-$d_6$, mixture of diastereomers) δ 212.2, 184.7, 184.6, 168.2, 159.1, 154.4, 152.9, 152.8, 151.5, 138.2, 134.5, 133.7, 132.9, 132.3, 131.5, 126.7, 126.6, 126.4, 126.3, 118.2, 118.0, 117.3, 116.5, 116.0, 109.1, 108.9, 98.6, 73.3, 71.8, 68.1, 66.6, 66.2, 65.1, 65.0, 63.1, 62.1, 54.9, 50.4, 45.7, 34.8, 30.4, 28.2, 28.0, 15.4; HRMS $[M+H]^+$ calcd. 835.2556 for $C_{41}H_{43}N_2O_{17}^+$, found 835.2569.

(11)

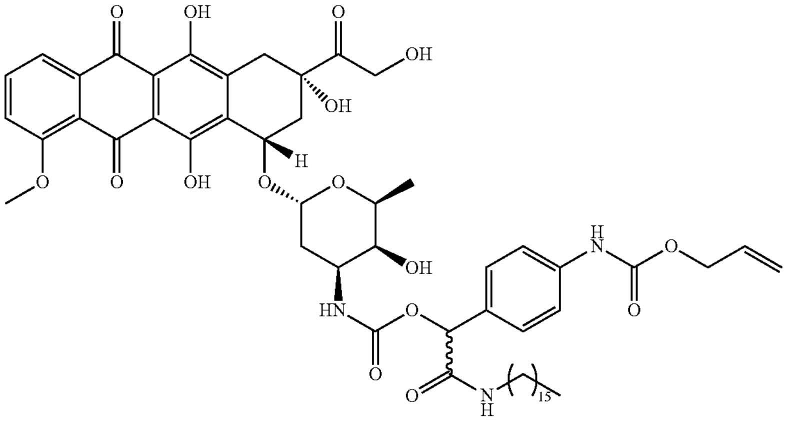

Alloc-SIL-$C_{16}$-Dox

To a solution of Alloc-SIL-Dox (10) (83.5 mg, 0.1 mmol) in MeOH (3 mL) and THF (5 mL) was added an aqueous solution of LiOH monohydrate (420 mM, 0.714 mL, 0.3 mmol). The solution was stirred for 25 min. Acidic cation exchange resin (Dowex 500X8-H, 0.5 g) was added and stirring was continued for 1 min. The resin was removed by filtration and washed with methanol. The filtrate was concentrated under reduced pressure and the residue was redissolved in dry DMF (0.4 mL) and dry methanol (0.8 mL). To the solution was added $NEt_3$ (69.7 μL, 0.5 mmol), HBTU (41.7 mg, 0.11 mmol) and a solution of hexadecylamine (50 mM in dry THF, 3 mL, 0.15 mmol). The mixture was stirred until LCMS indicated full conversion and then directly loaded onto a Biotage SNAP C18 column (30 g). Reversed phase chromatography ($H_2O$/acetonitrile gradient elution, 0.1% formic acid) afforded Alloc-SIL-$C_{16}$-Dox (11) (45 mg, 43%); $^1H$ NMR (600 MHz, DMF-$d_7$, mixture of diastereomers) δ 14.31-14.16 (m, 1H), 13.45-13.29 (m, 1H), 9.77-9.66 (m, 1H), 8.13-8.08 (m, 1H), 8.03 (s, 1H), 7.98-7.91 (m, 2H), 7.74-7.69 (m, 1H), 7.58-7.50 (m, 2H), 7.42-7.35 (m, 2H), 7.02-6.87 (m, 1H), 6.05-5.95 (m, 1H), 5.73 (s, 1H), 5.42-5.32 (m, 2H), 5.24-5.19 (m, 1H), 5.12-5.04 (m, 1H), 4.84-4.72 (m, 2H), 4.68-4.56 (m, 3H), 4.35-4.28 (m, 1H), 4.11-4.04 (m, 4H), 3.91-3.84 (m, 2H), 3.18-3.01 (m, 5H), 2.50-2.38 (m, 1H), 2.29-2.21 (m, 1H), 2.05-1.95 (m, 1H), 1.80-1.63 (m, 1H), 1.45-1.37 (m, 2H), 1.29-1.12 (m, 33H), 0.90-0.84 (m, 3H); $^{13}C$ NMR (150 MHz, DMF-$d_7$, mixture of diastereomers) δ 214.4, 187.3, 187.2, 169.30, 169.28, 163.2, 161.64, 161.61, 156.92, 156.88, 155.5, 155.4, 154.9, 154.8, 153.83, 153.80, 139.9, 136.5, 135.9, 135.5, 134.6, 133.8, 131.8, 128.2, 128.1, 120.8, 120.7, 119.91, 119.88, 119.4, 118.2, 117.13, 117.11, 111.4, 111.3, 101.3, 101.2, 76.0, 75.5, 75.4, 70.5, 69.1, 67.6, 67.5, 65.2, 65.1, 64.9, 56.67, 56.65, 47.92, 47.88, 39.0, 38.9, 37.0, 32.9, 32.0, 29.8, 26.9, 25.6, 22.8, 17.0, 13.9; HRMS $[M-H]^-$ calcd. 1042.4918 for $C_{56}H_{72}N_3O_{16}^-$, found 1042.4930.

MMAE (108 mg, 0.15 mmol) was added to a solution of Alloc-SIL-PNP (9) (94.7 mg, 0.22 mmol), DIPEA (40.1 μL, 0.23 mmol), and HOBt (20.3 mg, 0.15 mmol) in dry DMSO (1.5 mL). The mixture was stirred at room temperature for 2 h (LCMS showed full conversion). Excess Alloc-SIL-PNP was quenched by addition of 2-(2-aminoethoxy)ethanol (10 μL, 0.1 mmol) and stirring was continued for 30 min. The mixture was directly loaded onto a Biotage SNAP Ultra C18 column (30 g). Reversed phase chromatography ($H_2O$/acetonitrile gradient elution, 0.1% formic acid) afforded MMAE-SIL-$C_{16}$-Dox (10) (140 mg, 92%); $^1H$ NMR (400 MHz, DMSO-$d_6$, mixture of diastereomers and rotamers) δ 9.87-9.79 (m, 1H), 8.33-8.04 (m, 1H), 7.92-7.85 (m, 0.6H), 7.65-7.59 (m, 0.4H), 7.54-7.45 (m, 3H), 7.43-7.37 (m, 1H), 7.34-7.24 (m, 4H), 7.22-7.15 (m, 1H), 5.99 (ddt, J=17.1, 10.6, 5.4 Hz, 1H), 5.87-5.76 (m, 1H), 5.43-5.32 (m, 2H), 5.24 (dq, J=10.6, 1.3 Hz, 1H), 4.81-4.66 (m, 1H), 4.64-4.59 (m, 2H), 4.53-4.20 (m, 3H), 4.07-3.91 (m, 2H), 3.82-3.76 (m, 0.5H), 3.64-3.54 (m, 4H), 3.53-3.42 (m, 0.5H), 3.33 (s, 3H), 3.27-3.10 (m, 9H), 3.06-2.86 (m, 5H), 2.47-2.37 (m, 1H), 2.34-2.21 (m, 1H), 2.19-2.09 (m, 2H), 2.08-2.06 (m, 4H), 1.86-1.69 (m, 3H), 1.60-1.44 (m, 2H), 1.38-1.24 (m, 1H), 1.08-0.96 (m, 7H), 0.96-0.71 (m, 19H), 0.65-0.55 (m, 1H); $^{13}C$ NMR (100 MHz, DMSO-$d_6$, mixture of diastereomers and rotamers) δ 170.7, 170.6, 168.0, 167.9, 167.1, 161.4, 153.6, 153.3, 151.5, 142.0, 138.2, 138.1, 138.0, 131.6, 126.6, 126.5, 126.4, 126.3, 126.11, 126.06, 125.1, 125.0, 124.8, 124.7, 116.7, 116.4, 116.0, 83.8, 80.0, 76.0, 75.3, 73.1, 72.9, 63.1, 61.8, 61.6, 59.3, 58.6, 57.0, 56.5, 55.5, 55.4, 53.3, 52.6, 52.5, 50.5, 48.1, 47.5, 45.5, 44.6, 42.1, 41.6, 35.5, 33.5, 30.1, 29.9, 28.6, 28.4, 28.2, 25.7, 25.2, 25.1, 23.7, 23.6, 22.7, 21.5, 17.6, 17.4, 17.3, 17.2, 17.13, 17.06, 16.9, 16.7, 14.2, 14.0, 13.8, 13.7, 13.6, 13.3, 8.7, 8.6; HRMS $[M+H]^+$ calcd. 1009.5856 for $C_{53}H_{81}N_6O_{13}^+$, found 1009.5843.

(12)

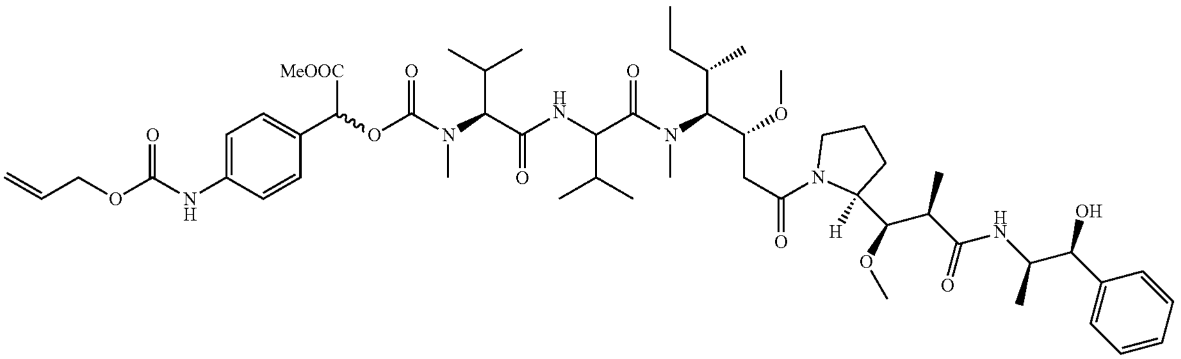

Alloc-SIL-MMAE (13)

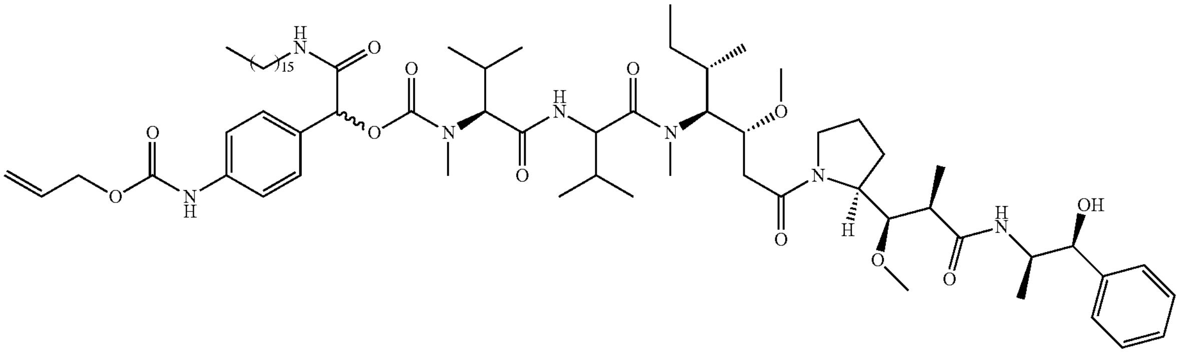

Alloc-SIL-$C_{16}$-MMAE

To a solution of Alloc-SIL-MMAE (12) (124.2 mg, 0.123 mmol) in MeOH (9 mL) was added an aqueous solution of LiOH monohydrate (420 mM, 0.878 mL, 0.369 mmol). The solution was stirred for 30 min. Acidic cation exchange resin (Dowex 500X8-H, 0.5 g) was added and stirring was continued for 1 min. The resin was removed by filtration and washed with methanol. The filtrate was concentrated under reduced pressure and the residue was redissolved in dry DMF (1 mL). To the solution was added $NEt_3$ (51.4 μL, 0.37 mmol), a solution of HBTU (166 mM in THF/DMF, v/v=2/1, 1.04 mL, 0.17 mmol) and a solution of hexadecylamine (50 mM in dry THF, 3.44 mL, 0.17 mmol). The mixture was stirred until LCMS indicated full conversion and then directly loaded onto a Biotage SNAP C18 column (30 g). Reversed phase chromatography ($H_2O$/acetonitrile gradient elution, 0.1% formic acid) afforded Alloc-SIL-$C_{16}$-MMAE (13) (98.1 mg, 65%); $^1$H NMR (600 MHz, DMF-$d_7$, mixture of diastereomers and rotamers) δ 9.81-9.72 (m, 1H), 8.36-8.30 (m, 0.5H), 8.24-8.18 (m, 0.4H), 8.10-8.05 (m, 0.5H), 8.03 (s, 0.5H), 7.98-7.91 (m, 0.6H), 7.89-7.79 (m, 0.5H), 7.71-7.67 (m, 0.5H), 7.65-7.58 (m, 2H), 7.55-7.48 (m, 2H), 7.46-7.40 (m, 2H), 7.38-7.30 (m, 2H), 7.26-7.18 (m, 1H), 6.05-5.96 (m, 1.6H), 5.93-5.86 (m, 0.4H), 5.39-5.34 (m, 1H), 5.25-5.20 (m, 1H), 4.96-4.85 (m, 0.5H), 4.82-4.67 (m, 1.5H), 4.66-4.53 (m, 3H), 4.39-4.25 (0.4H), 4.25-4.09 (m, 2H), 3.98-3.93 (m, 0.4H), 3.92-3.87 (m, 0.4), 3.69-3.57 (m, 1H), 3.55-3.46 (m, 1H), 3.40-3.24 (m, 8H), 3.21-3.09 (m, 4H), 3.08-2.99 (m, 1H), 2.65-2.41 (m, 1.3H), 2.34-2.18 (m, 1.5H), 2.15 (s, 1.5H), 2.10-1.81 (m, 2.4H), 1.75-1.53 (m, 1H), 1.50-1.38 (m, 2.5H), 1.31-1.19 (m, 27H), 1.17-1.01 (m, 7H), 1.01-0.74 (m, 22H); $^{13}$C NMR (150 MHz, DMF-$d_7$, mixture of diastereomers and rotamers) δ 173.4, 173.3, 173.2, 170.8, 170.7, 170.3, 170.3, 170.2, 170.2, 169.7, 169.6, 169.5, 169.5, 169.4, 169.4, 169.1, 169.1, 169.0, 169.0, 163.2, 156.2, 156.1, 155.2, 155.1, 155.0, 153.8, 153.8, 144.2, 144.2, 144.1, 140.2, 140.1, 133.8, 131.6, 131.6, 131.5, 131.5, 131.3, 131.1, 131.1, 128.4, 128.3, 128.2, 128.1, 128.1, 127.2, 127.2, 127.1, 127.0, 127.0, 126.8, 118.3, 117.9, 117.1, 86.1, 82.5, 78.4, 77.8, 77.0, 76.9, 76.7, 76.7, 75.8, 75.8, 75.6, 65.2, 64.7, 64.6, 64.5, 64.4, 64.3, 63.1, 61.1, 60.6, 59.5, 59.0, 57.4, 56.6, 55.7, 55.2, 55.1, 54.9, 54.8, 54.7, 52.7, 50.8, 50.2, 50.1, 47.8, 46.8, 46.7, 44.7, 44.2, 39.3, 39.1, 39.0, 37.7, 37.7, 35.9, 32.0, 27.3, 27.2, 27.2, 27.0, 26.9, 26.8, 26.0, 25.9, 25.0, 24.9, 23.6, 22.8, 19.3, 19.2, 19.1, 19.0, 18.9, 18.8, 18.7, 18.6, 18.4, 18.3, 18.2, 18.1, 16.3, 16.1, 15.8, 15.6, 15.4, 14.9, 14.8, 14.7, 14.1, 13.9, 13.8, 12.0, 11.9, 11.9, 10.5, 10.4, 10.3, 10.2, 7.3; HRMS $[M-H]^-$ calcd. 1218.8363 for $C_{68}H_{112}N_7O_{12}^+$, found 1218.8377.

Example 4—Palladium Catalysts (See FIG. 26)

Palladium catalysts Pd-1, Pd-2, Pd-3, and Pd-4 were prepared as described in the literature. (see references 38-41)

Example 5—Nanoparticulate Prodrug Design, Optimization, and Characterization

The overall design for prodrug multifunctionality lies in a central 3-branched self-immolative linker (SIL) based on 4-aminomandelic acid (FIG. 1A). The $NH_2$-trigger is protected by the palladium-reactive Alloc group, while the benzylic position and the carboxyl group accommodate both the drug and an additional functional moiety, respectively, which in this case was used to tune hydrophobicity based on the particular application. Upon palladium-mediated cleavage of Alloc, self-immolation of the linker leads to drug release via rapid 1,6-elimination (FIG. 1B).

Figure 8A:
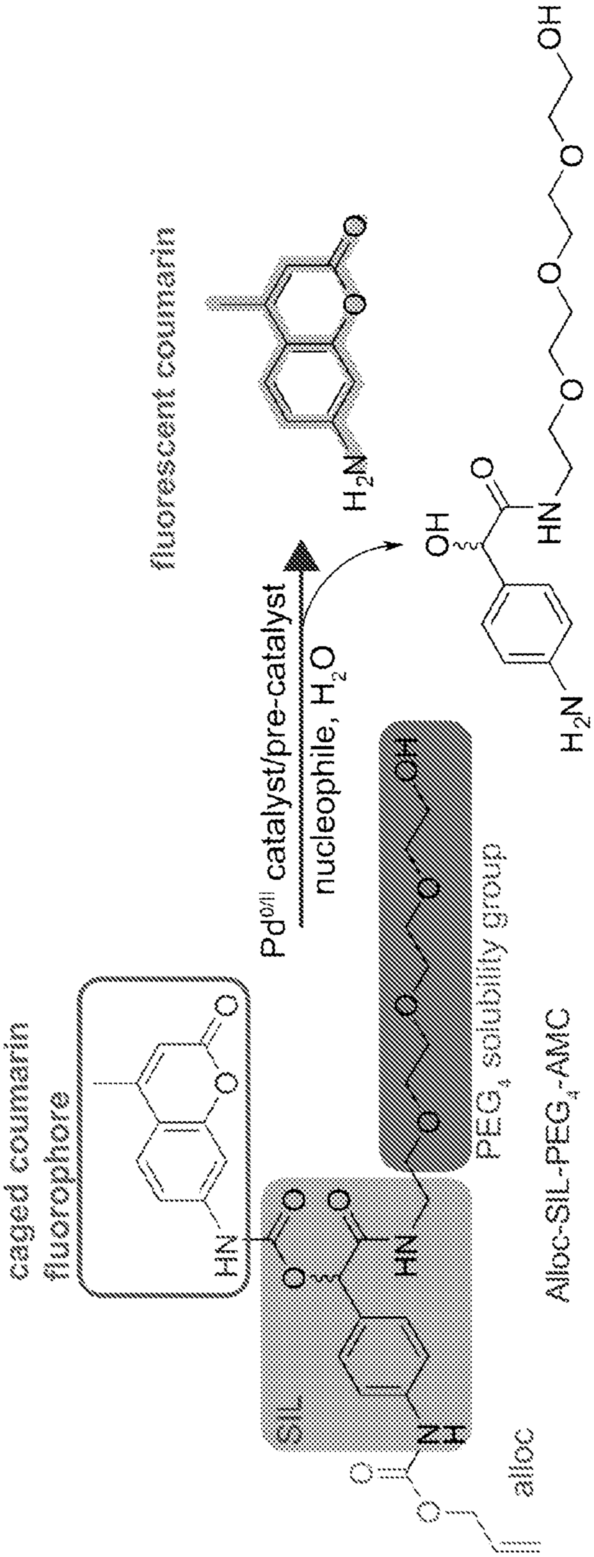
Figure 8B:
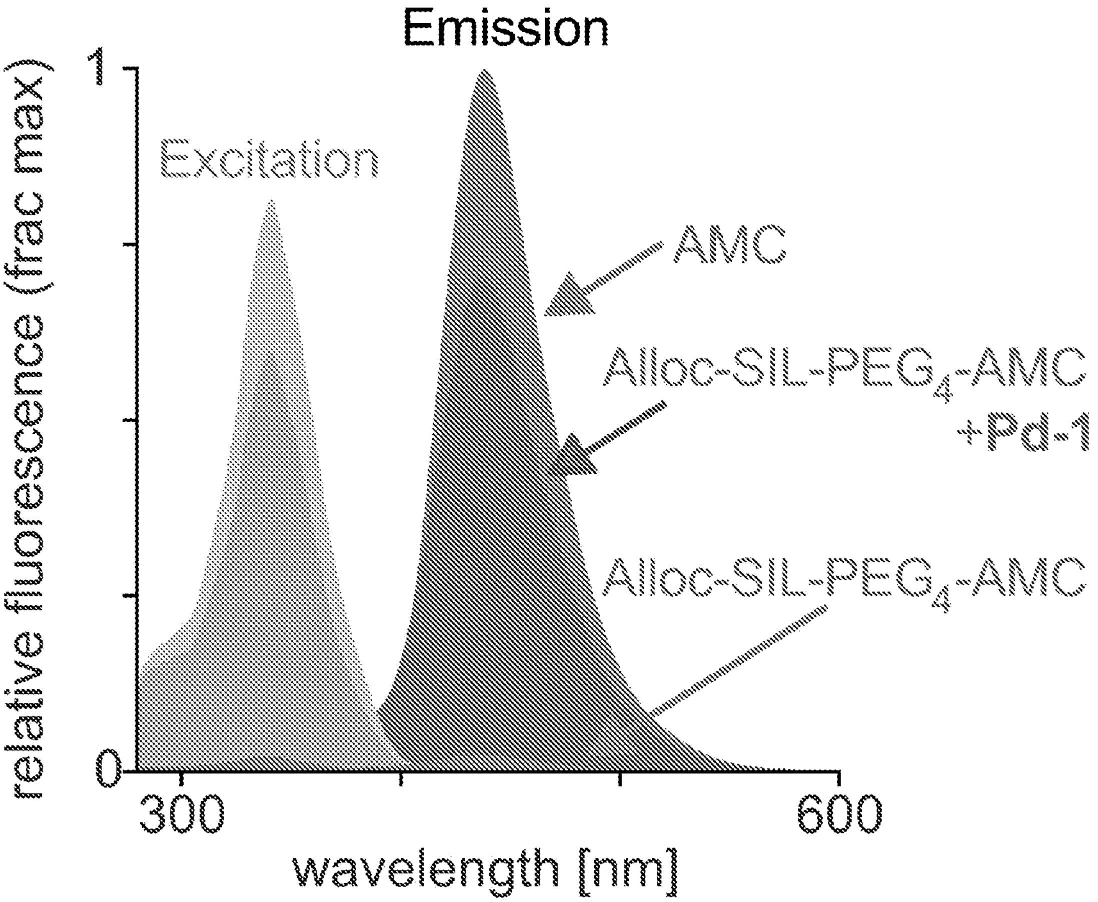

A fluorogenic probe was made to screen reactivity against a panel of palladium compounds with organic ligands that were discovered from previous studies to be active in physiological solutions.[5] The central SIL and Alloc group were used to cage 4-methyl-7-aminocoumarin (AMC), with addition of a polyethylenegly col (PEG) side chain to improve solubility, yielding Alloc-SIL-PEG4-AMC (FIG. 8A). Bioorthogonal activation, monitored by fluorescence turn-on (FIG. 8B), was screened in Hank's Buffered Saline Solution (HBSS) and Minimal Essential Medium (MEM), two physiologically-relevant aqueous solutions that are ubiquitous in mammalian cell culture modeling. Consistent with previous studies of Alloc- and poc-deprotection,[5] $PdCl_2(TFP)_2$ was most efficient, achieving >75% yield in HBSS (FIG. 8C).

Figure 8D:
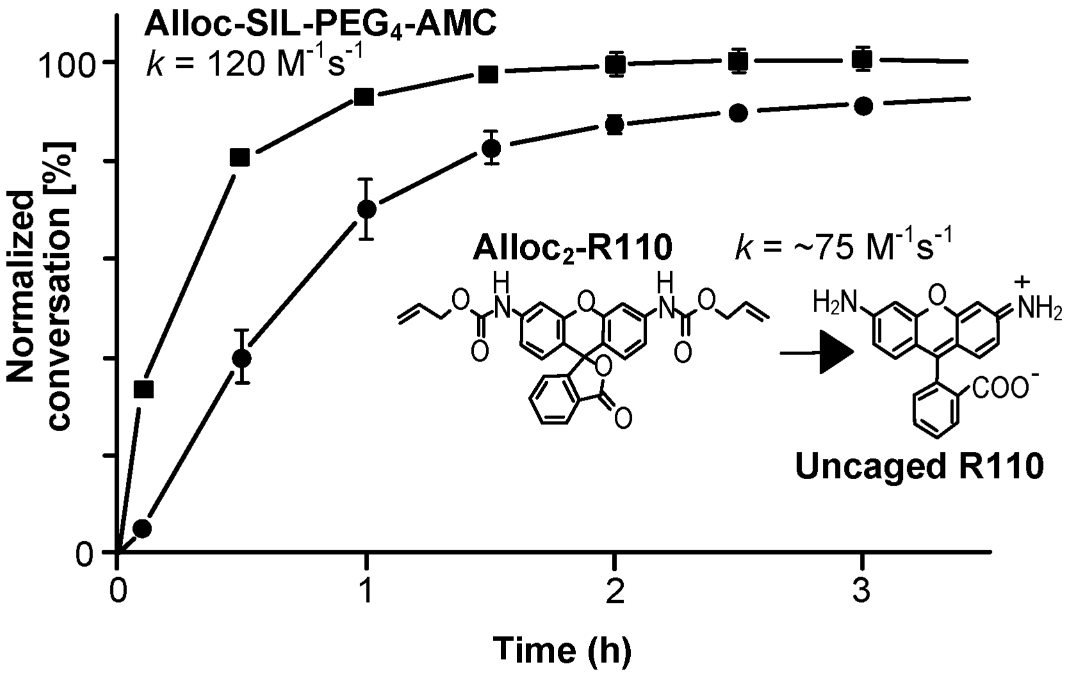

Using $PdCl_2(TFP)_2$, cleavage kinetics of the Alloc-SIL caging strategy was measured, and compared them to bis-alloc-rhodamine-110 ($Alloc_2R110$) deprotection, as a previously used model prodrug substrate.[5] Encouragingly, Pd-NP uncaged Alloc-SIL-PEG4-AMC approximately 1.5-fold faster than $Alloc_2R110$ (based on calculated second order rate constants, FIG. 8D). Thus, the Alloc-SIL strategy enables multifunctionality without compromising reaction kinetics.

Figure 2A:
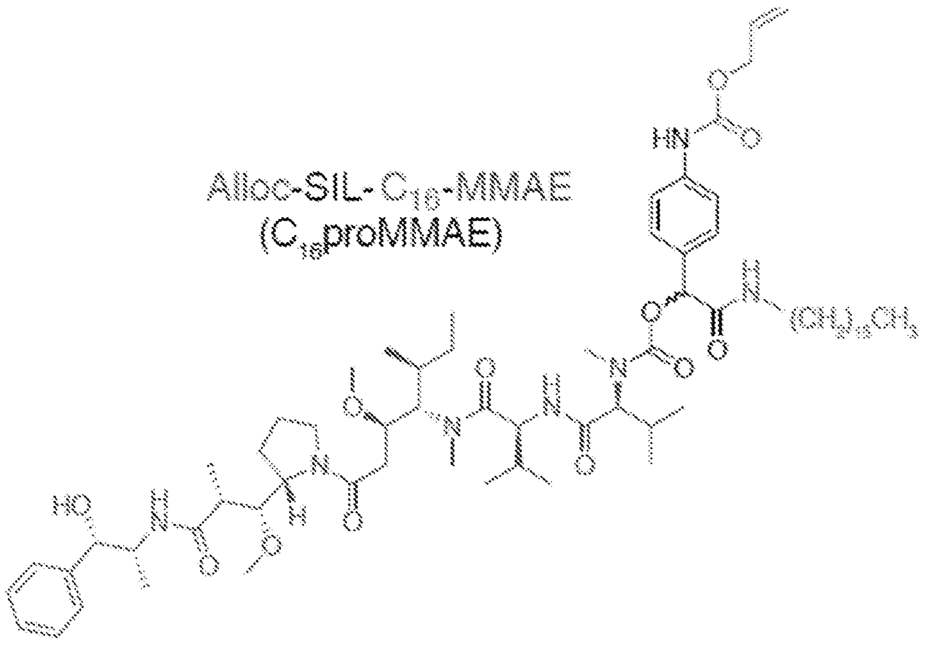
FIGS. 2A-2F. Caged MMAE and doxorubicin encapsulate into nanoparticles and are selectively cytotoxic in the presence of the Pd-NP bioorthogonal trigger. a-b) Chemical structure of caged MMAE (a) and doxorubicin (b), according to the scheme in FIG. 1. c-d) TEM imaging of C16proMMAE (c) and C16proDOX (d) encapsulated in a formulation of PLGA-PEG polymeric micelles. Particle diameters were quantified according to their distribution (black bars) and gaussian fit (red curve), with representative images shown at right (scale bar, 100 nm). e-f) Cytotoxicity was determined for caged MMAE (e) and doxorubicin (f) at the indicated concentration (x-axis), in the presence of varying amounts of Pd-NP bioorthogonal trigger, over 72 h treatment using HT1080 fibrosarcoma cells (n=2, data are means±s.e.m.). Parent non-caged compounds were also tested as controls (black curves)
Figure 2B:
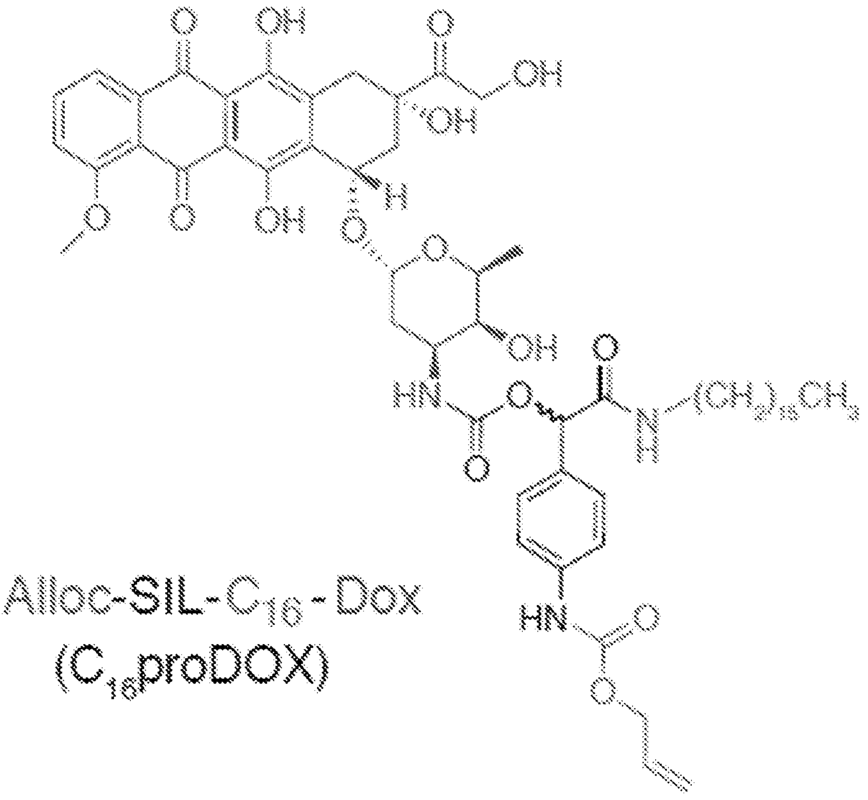
Figure 2C:
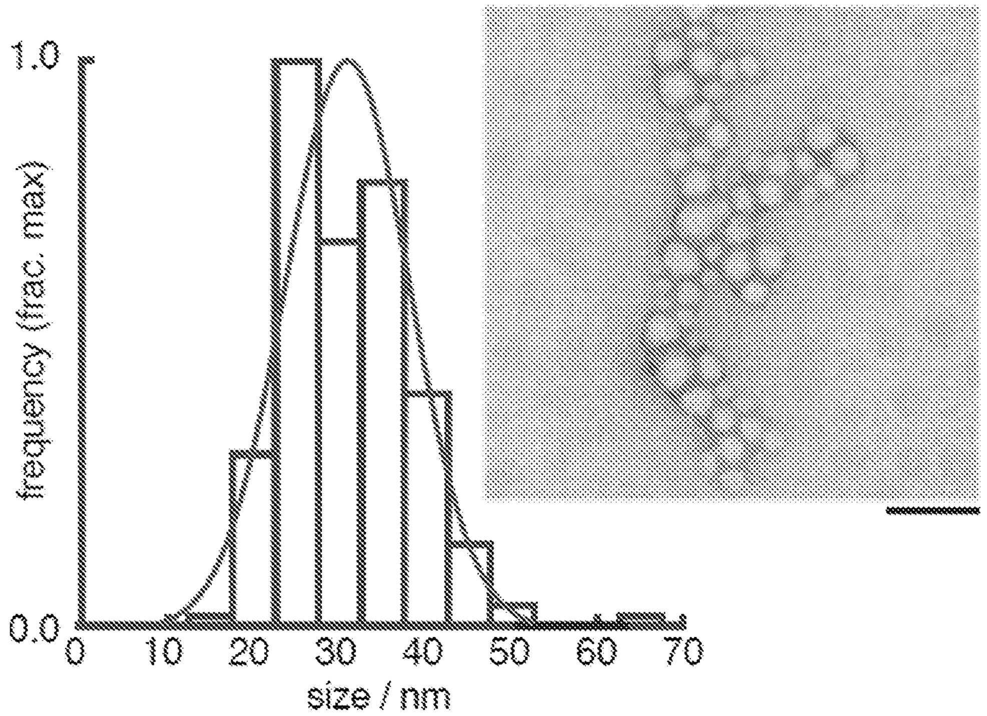
Figure 2D:
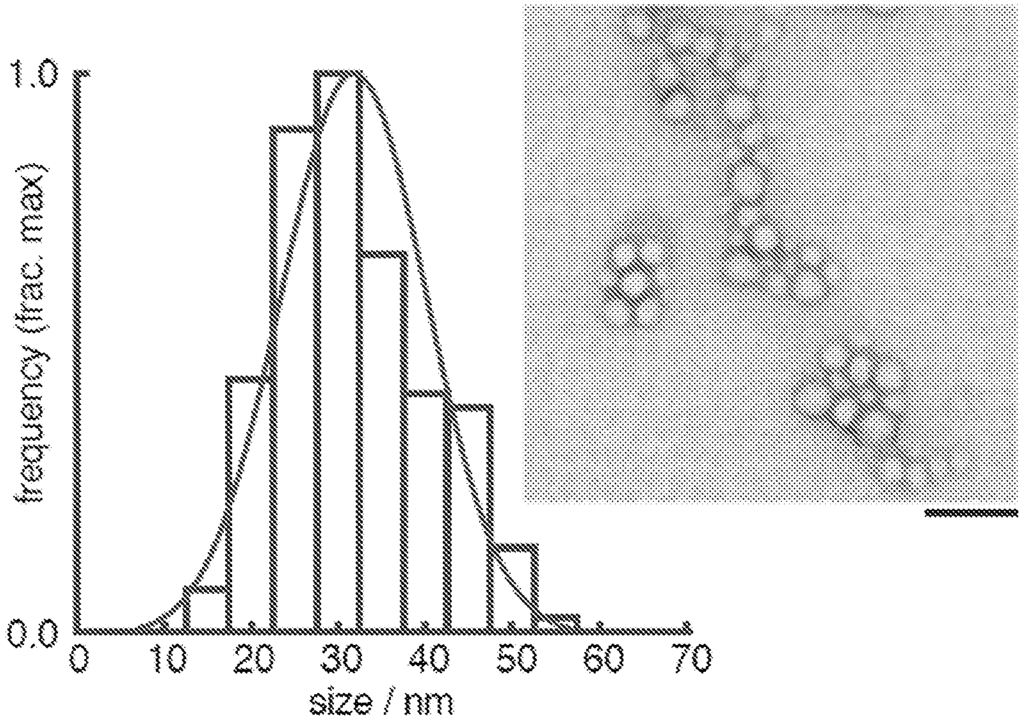

The prodrug strategy was applied to two model anticancer therapies, monomethyl auristatin E (MMAE) and doxorubicin (DOX). The Alloc-SIL group was employed as above, but using a $C_{16}$ aliphatic anchor rather than PEG in order to facilitate efficient nano-encapsulation into a clinically relevant polymeric micellar formulation containing a hydrophobic PLGA-based core. The resulting lipophilic prodrugs Alloc-SIL-$C_{16}$-MMAE ("$C_{16}$proMMAE", FIG. 2*a*) and Alloc-SIL-$C_{16}$-DOX ("$C_{16}$proDOX", FIG. 2*b*) were both nano-encapsulated with >90% efficiency with acceptable size and polydispersity, shown by transmission electron microscopy (FIG. 2*c-d*) and dynamic light scattering (FIG. 9A). Without the $C_{16}$ anchor, the amphiphilic doxorubicin (c Log P=−0.7) exhibited only moderate encapsulation (22%),[5] and encapsulation of parent MMAE was undetectable using the same nanoprecipitation strategy. The $C_{16}$ anchored prodrug nanoformulations were stable, with no increase in size or polydispersity after 72 h at 37° C. in PBS; size was uniform with PDI of 0.11-0.13 throughout (FIG. 9B). Over 72 h at 37° C. in PBS, release of the prodrug payload from the nanoformulation was 20%±6% and 9% 1% for $C_{16}$proDOX and $C_{16}$proMMAE, respectively (n=3).

Example 6—Bioorthogonally Triggered In Vitro Cytotoxicity of the Prodrug

In addition to enhancing nano-encapsulation efficiency, the SIL strategy further reduced cytotoxicity of doxorubicin in its caged form, tested using HT1080 fibrosarcoma cancer cells (a model extensively characterized for its in vitro and in vivo responsiveness to prodrug nanoformulations). Alloc caging increased the concentration at which 50% of cells died in a resazurin-based cytotoxicity assay ($IC_{50}$) from 0.1 μM to 18 μM; however, the $IC_{50}$ was not reached at concentrations up to 50 μM for the $C_{16}$proDOX compound. The concentration at which 20% of cells died ($IC_{20}$) was roughly 15-fold higher than for the previously described prodrug Alloc-DOX,[5] and 1900-fold higher than for uncaged DOX (FIG. 10). For both prodrug formulations, co-incubation of cells with Pd-NP restored drug cytotoxicity (FIG. 10C).

Figure 2E:
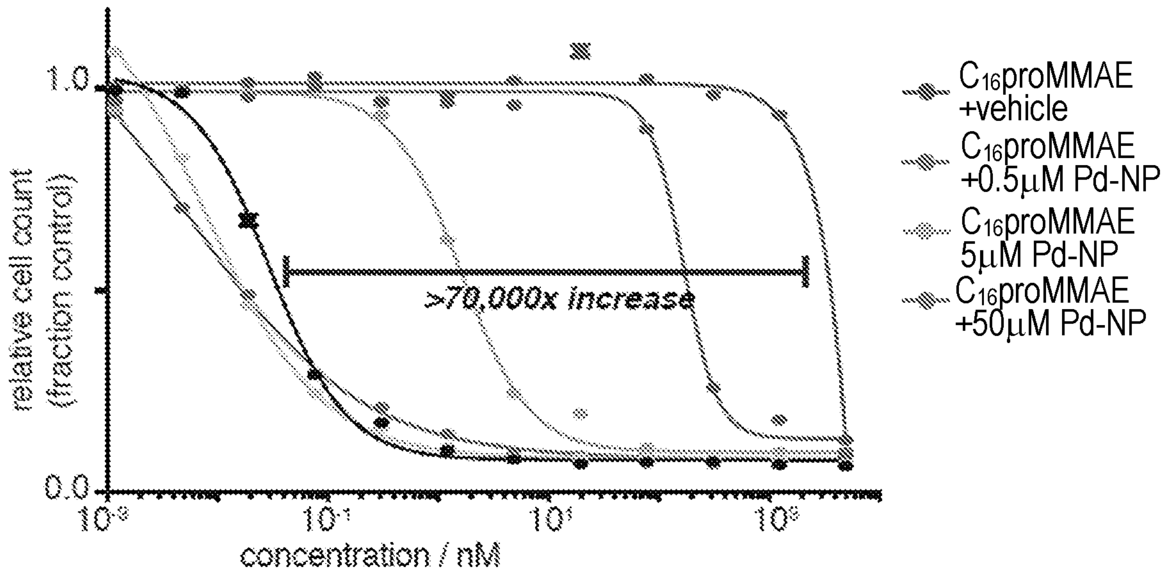
Figure 2F:
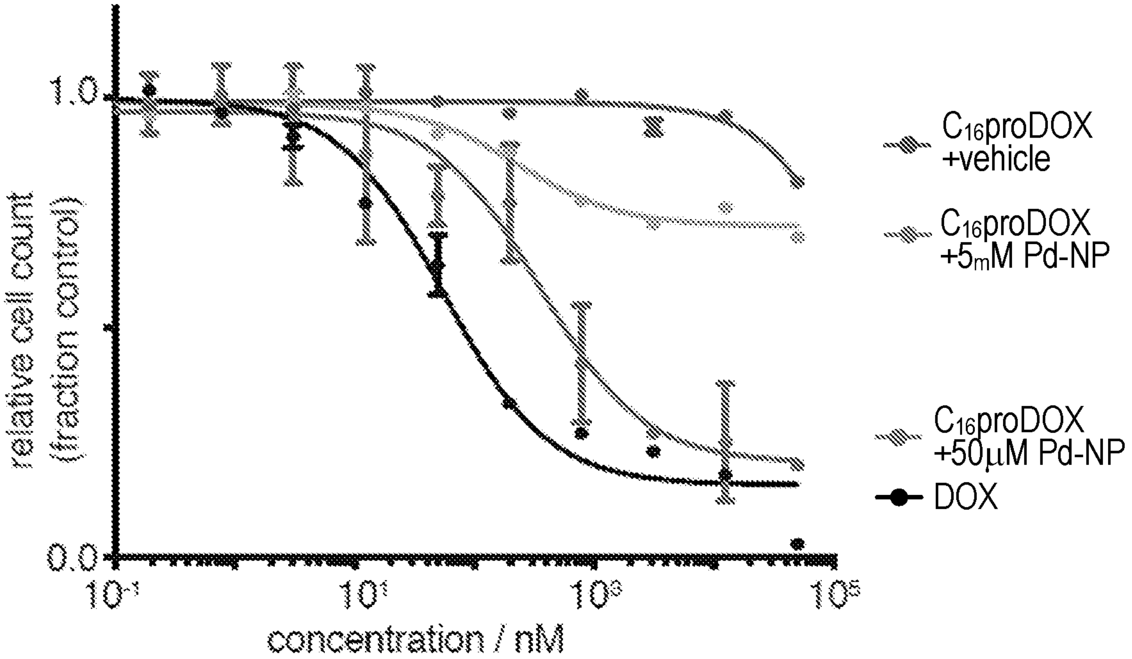

Compared to the doxorubicin prodrugs, $C_{16}$proMMAE exhibited even greater potency upon Pd-NP activation, showing a $>10^4$ fold-increase in $IC_{50}$ to 15 pM, which is comparable to cytotoxicity of the uncaged parent compound, MMAE (FIG. 2*e-f*). $C_{16}$proMMAE shows >10-fold enhanced cytotoxicity when incubated with sub-micromolar Pd-NP, which is promising considering 5-7.5 μM tumoral Pd-NP concentrations have been safely achieved in xenograft tumor models.[5] Based on cytotoxicity, the level of $C_{16}$proMMAE activation approaches >90% as Pd-NP concentration is increased to 50 μM. Although this concentration is high for typical small molecule therapeutics, past studies have shown it to be relatively non-toxic (typical $IC_{50}$>100 μM),[5] and it is modest when considering that many transition-metal bioorthogonal catalysts—including those based on Pd—are used as heterogeneous resins and implants that often employ much larger doses of metal by mass.[12]

Example 7—Mechanisms of Cellular NP Uptake and Activity

Figure 3A:
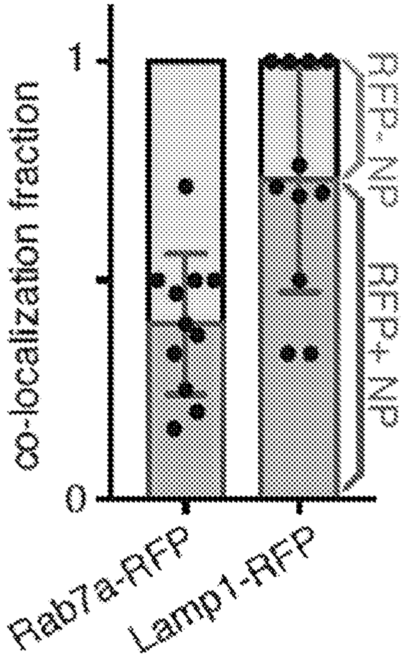
FIGS. 3A-3D. Imaging reveals in vitro pathways of cell uptake and C16proDOX activation. a) HT1080 tumor cells expressing either Rab7a-RFP or Lamp1-RFP fusion proteins were incubated with a fluorescently labeled NP based on the prodrug formulation (PLGA-PEG+PLGA-BODIPY630) and imaged 24 h later. Co-localization was determined by tabulating the fraction of NP-positive puncta (vesicles) in cells that contained high RFP expression or not (labeled red and gray, respectively; n>10 cells, bars are mean±std. dev.).
Figure 3B:
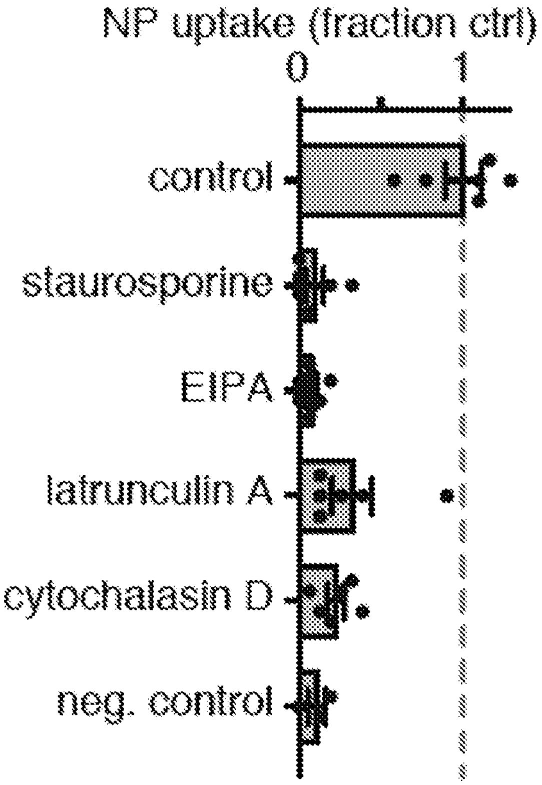

The mechanism of cellular prodrug uptake was next investigated. HT1080 cells were made to transgenically express Rab7a-RFP and Lamp1-RFP fluorescent fusion proteins, which localize to the late endosome and lysosome, respectively. After 24 h treatment with fluorescent NPs based on the $C_{16}$ prodrug formulation, co-localization was quantified between the NPs and Rab7a or Lamμl positive vesicles (FIG. 3*a*, 11*a*). Fluorescence microscopy revealed that NPs accumulated at high levels in vesicle-sized puncta within cells (FIG. 11*a*). Approximately ⅓ of these NP puncta were located in Rab7a-RFP+ vesicles, while roughly ⅔ were associated with Lamp1-RFP+ vesicles, suggesting NP uptake through endosomal/lysosomal pathways. Co-treatment with inhibitors of macropinocytosis (5-(N-Ethyl-N-isopropyl)amiloride, EIPA) and actin-dependent processes including macropinocytosis/endocytosis (latrunculin A and cytochalasin D as inhibitors of actin polymerization) acutely reduced the uptake of NPs (FIG. 3*b*). Broad inhibition of kinase signaling (via staurosporine), which is thought to be especially important for macropinocytic uptake in RAS-mutant cancer cells such as HT1080,[13] also decreased NP accumulation. These results collectively suggest that uptake of PLGA-PEG NPs, similar in structure to Pd-NP and $C_{16}$ prodrug NPs, occurs through actin-dependent endocytic/macropinocytic processes that lead to predominant lysosomal accumulation.

Past reports have delved into mechanisms of intracellular hydrolytic and enzymatic PLGA degradation for controlled drug release.[13] While environmentally-sensitive polymers have been successfully used in the past to facilitate endosomal escape, here these strategies did not appear necessary for prodrug activation and cytotoxic action. Despite endosomal/lysosomal NP accumulation, Pd-NP co-treatment was still able to restore a large fraction of the prodrug's cytotoxicity, such that its potency approaches that achieved with the parent drug (especially for $C_{16}$proMMAE, FIG. 2*e*). Prodrug activation can occur both extracellularly and intracellularly depending on relative pharmacokinetics and rates of prodrug release from the NP vehicle. In the models used here, it is inferred that the majority of $C_{16}$prodrug activation occurs intracellularly, given its slow extracellular release rate from the NP vehicle compared with timescales of pharmacokinetic clearance; <10% of $C_{16}$proDOX is activated when Pd-NP and prodrug-NPs are co-incubated in 37° C. PBS (measured by HPLC as in FIG. 12), and by 72 h the majority of NPs have been systemically cleared and taken up by cells, at least in the xenograft models used. Previous studies indicate Pd-mediated prodrug activation can occur extracellularly, including in the interstitium of tumor xenografts.[5] However, the prodrug in those cases did not contain a $C_{16}$ anchor, therefore leading to roughly 90% in vitro prodrug release from the NP vehicle into solution by 72 h at 37° C. in PBS. In contrast, <10% of $C_{16}$proMMAE is released in vitro into solution after 72 h (FIG. 9), which corresponds to a 20-fold slower kinetic release rate. Furthermore, past work with $C_{16}$-anchored fluorescent prodrugs encapsulated in similar PLGA-PEG NPs has shown direct cellular NP uptake to be a dominant component of delivery, including in tumor xenografts, and including in the HT1080 model.[14]

Several recent studies have implicated lysosomal pH as a contributing factor in payload release, using chloroquine (CQ) as an inhibitor of endosomal acidification and of autophagosome fusion with lysosomes.[15, 16] HT1080 cells were co-treated with CQ, Pd-NP, and $C_{16}$proDOX to understand whether CQ could block catalytic prodrug activation. In agreement with previous studies, it was found that CQ treatment led to the enhanced accumulation of NPs in distinctly large vesicles consistent with the induction of LC3+ autophagosome enrichment (FIG. 11*b*).[15, 16] Despite this morphological change, only modest impact was observed in the cytotoxicity of combined Pd-NP and $C_{16}$proDOX treatment, suggesting at least in this in vitro model that CQ effects, including its impact on lysosomal pH, are not substantial enough to completely block Pd-mediated prodrug activation (FIG. 11*c*). Moreover, previous work has indicated that low pH is not required for release and activity of Pd from its NP vehicle.[5] While further investigation of the subcellular mechanisms by which Pd-NP activates prodrugs extends beyond the scope of this disclosure, without being bound by theory, the data at hand suggest a model of endosomal/lysosomal accumulation and gradual liberation of the prodrug and catalyst from the NP vehicles, allowing them to react with each other. Controlled prodrug bioorthogonal cleavage then leads to the formation of an active compound that is able to escape sequestration and act on its intracellular target. Past work using fluorescent $C_{16}$-anchored prodrugs within PLGA-PEG nanoformulations has highlighted how drug payloads can freely escape lysosomal sequestration and even act on neighboring cells (including in HT1080 tumors), even though their polymeric vehicle remains intracellularly confined.[14]

Example 8—Imaging the Molecular Action of Pd-Activated Prodrugs

Figure 3C:
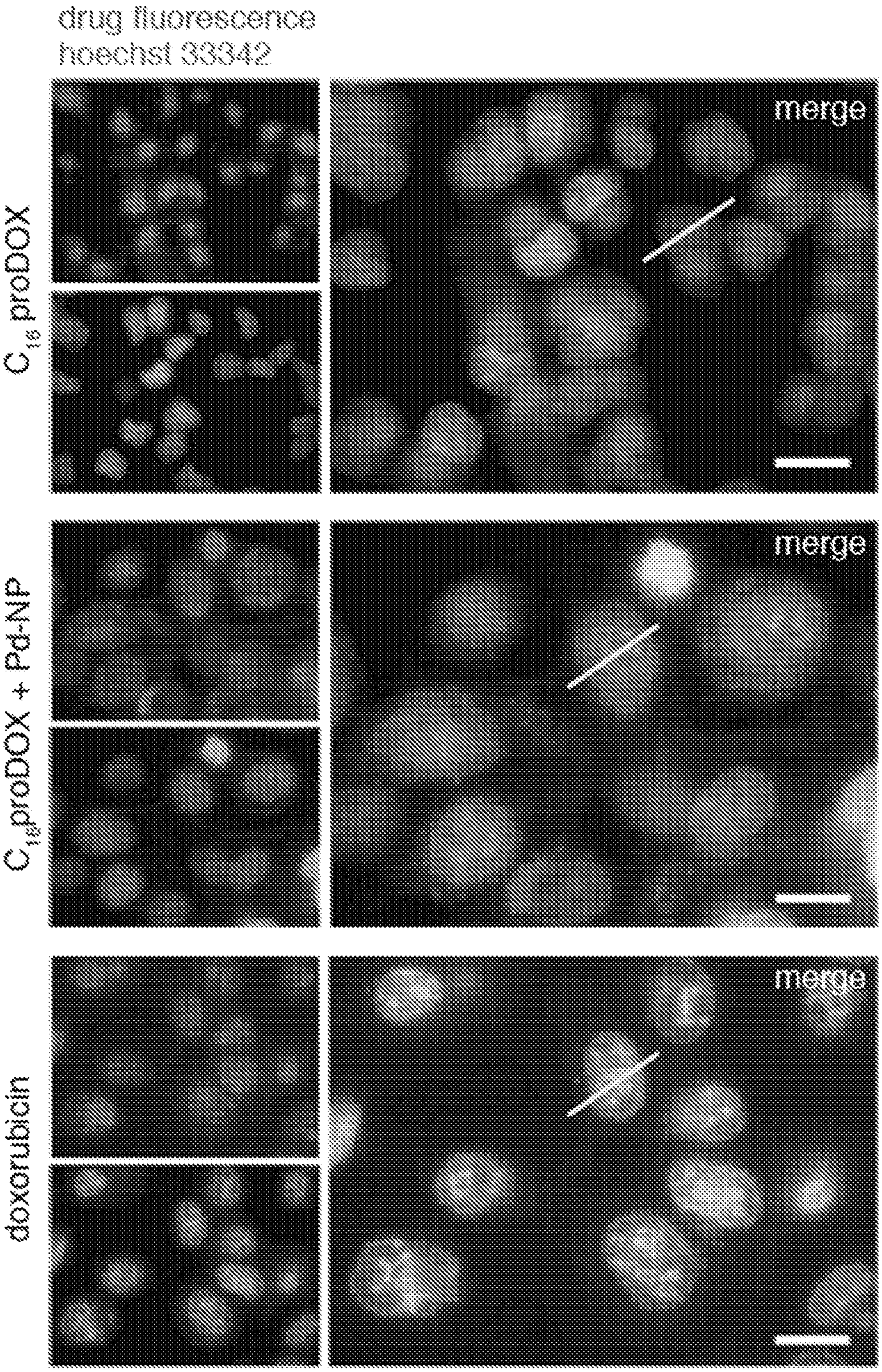
Figure 3D:
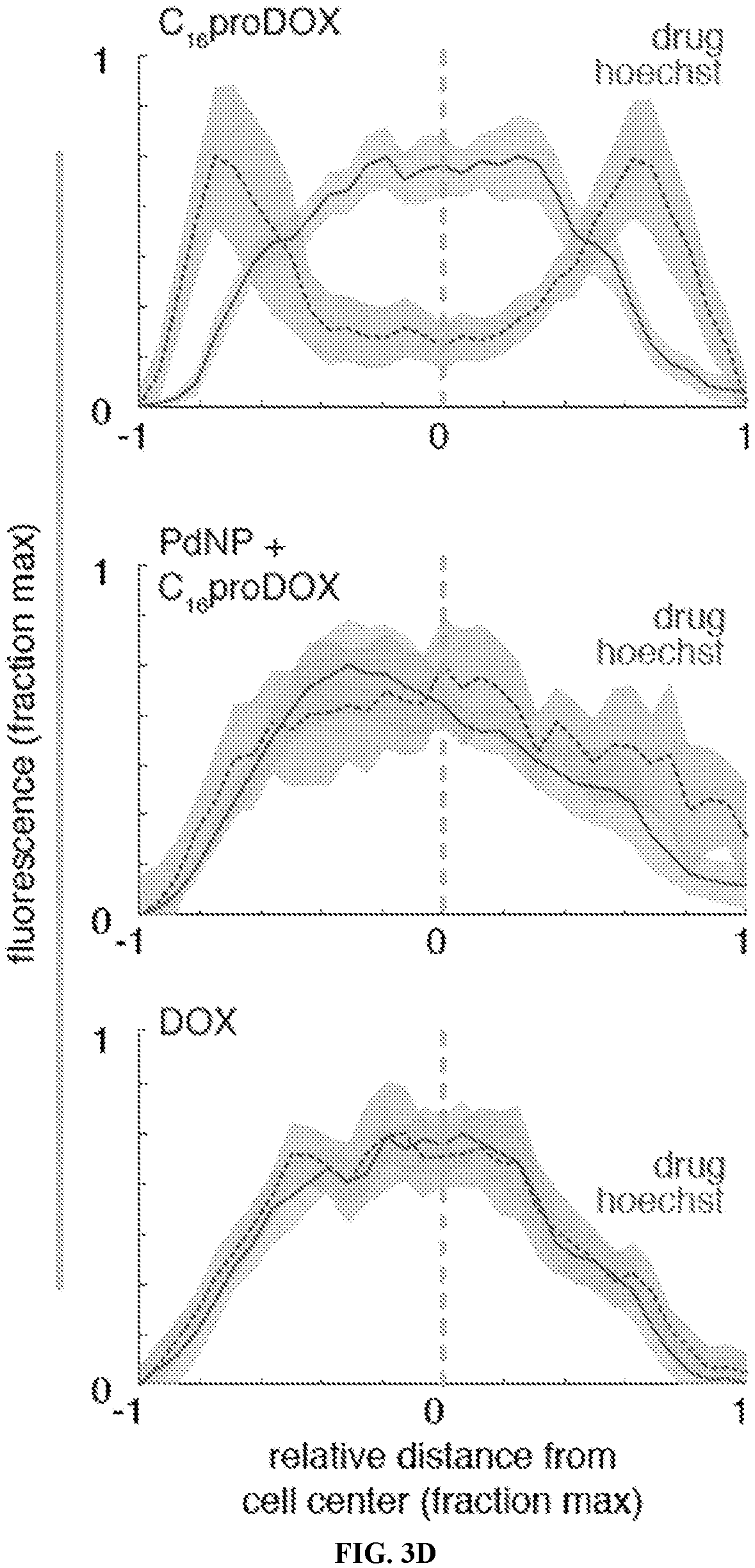
Figure 12A:
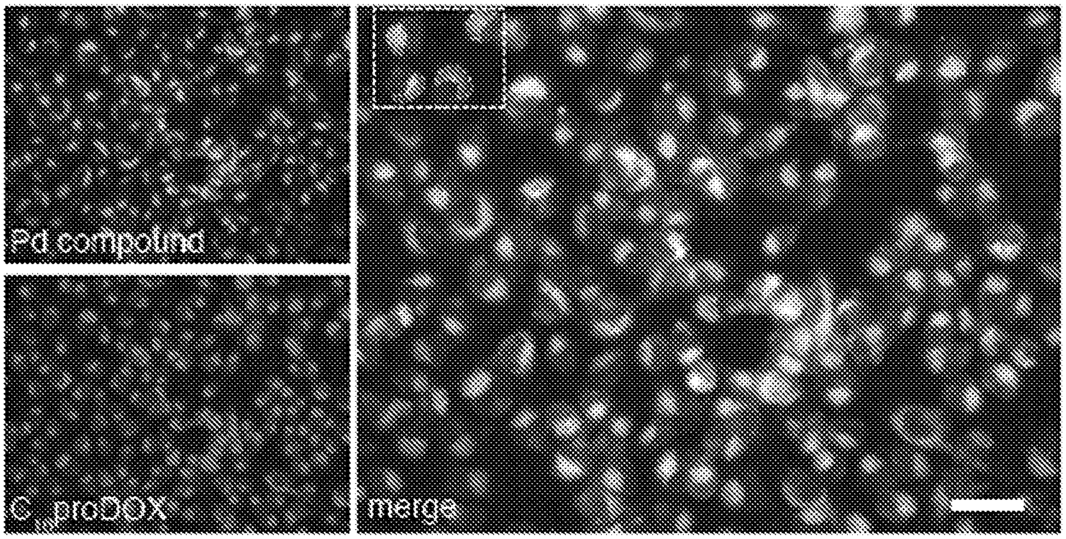
Figure 12B:
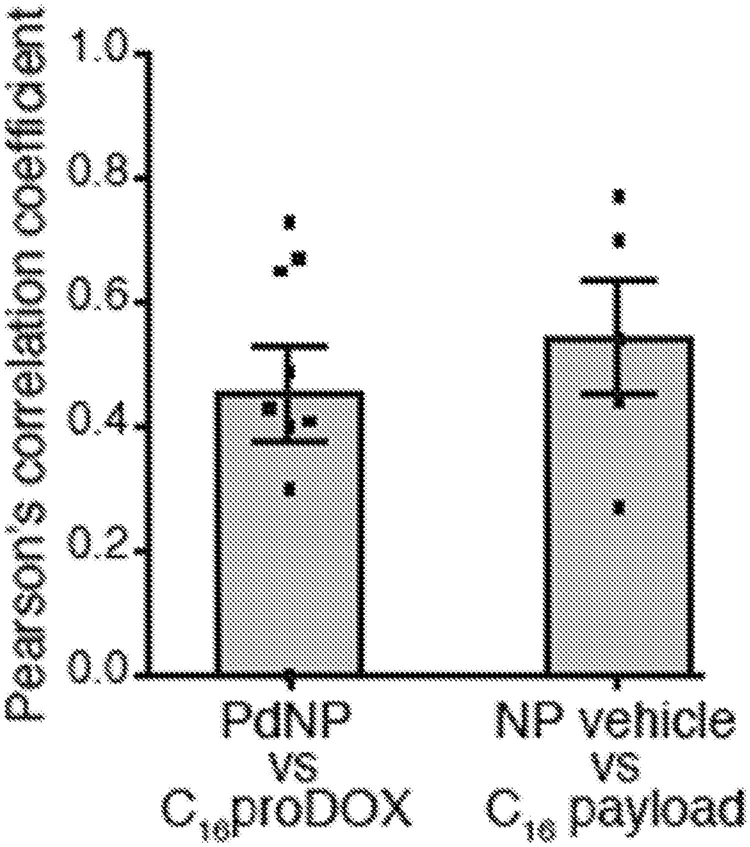
Figure 12C:
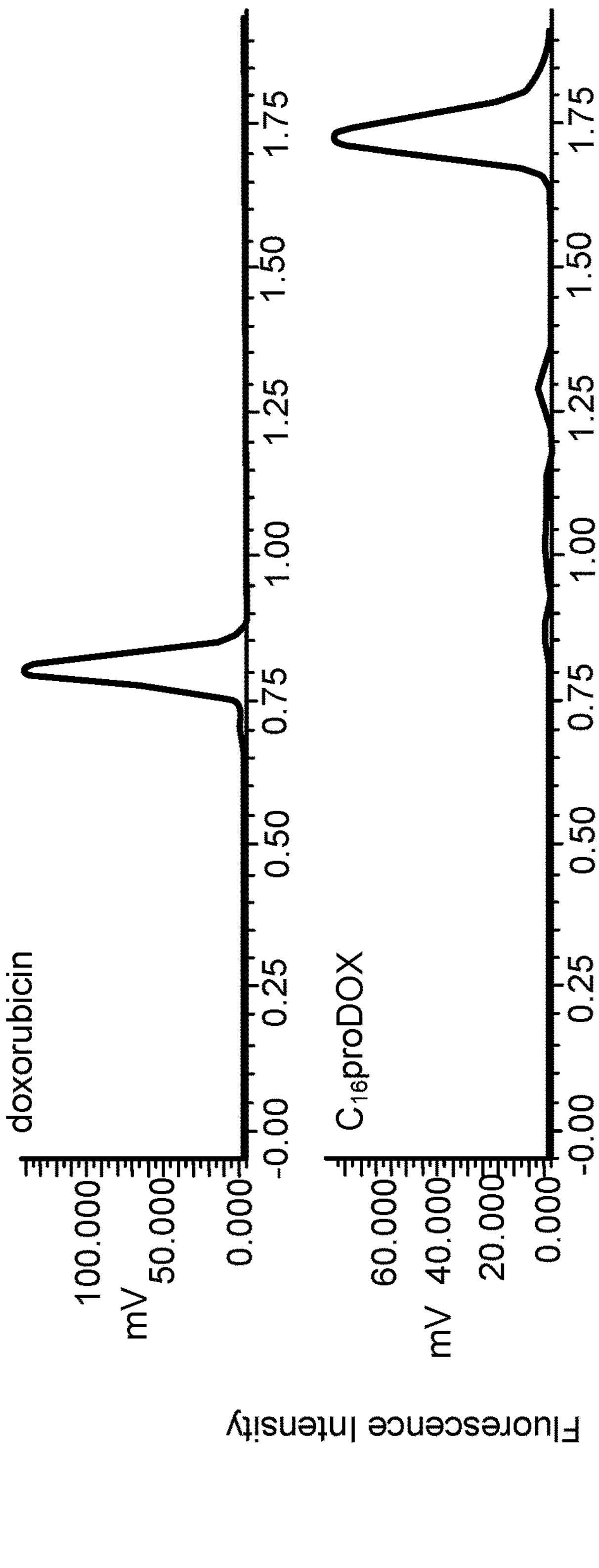
Figure 12D:
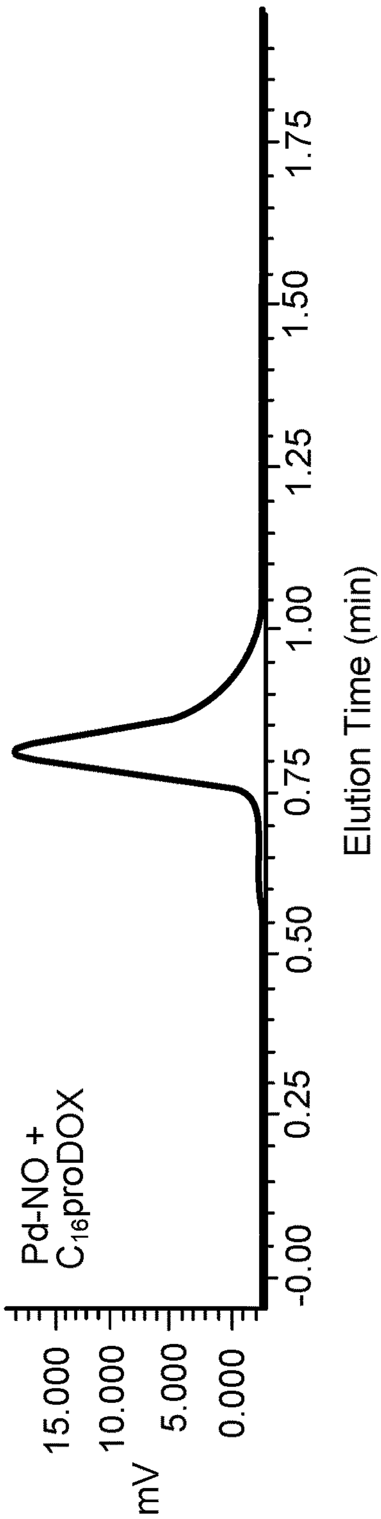
Figure 12E:
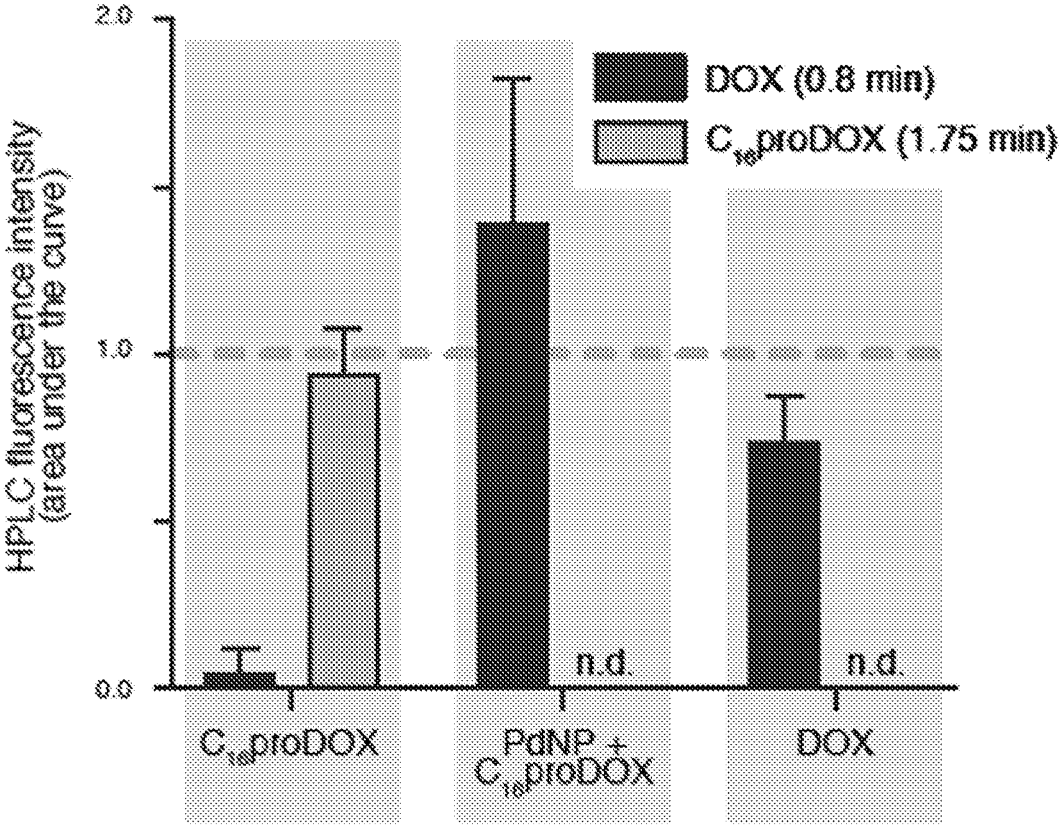
Figures 12F, 12G:
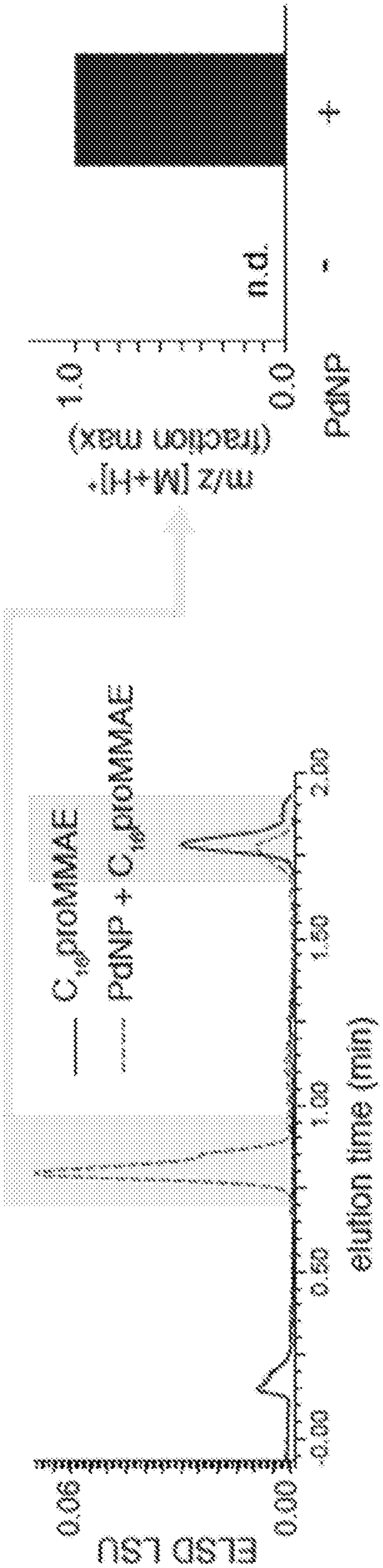

The intrinsic fluorescence of doxorubicin enabled to track where the prodrug actually accumulated in cells with and without activation by Pd-NP. Uncaged parent doxorubicin is capable of covalently binding DNA via the 3'-$NH_2$ group of the daunosamine sugar moiety, thus leading to topoisomerase II disruption and DNA damage. Consequently, covalently-reacting and DNA-intercalating doxorubicin primarily accumulates in the nuclei of cancer cells. However, fluorescence microscopy in HT1080 cancer cells showed that lipophilic $C_{16}$proDOX accumulated primarily in cytoplasmic/perinuclear cellular compartments consistent with late endosomal and lysosomal uptake but not in the nucleus itself (FIG. 12*a*). Encouragingly, co-incubation of cells with Pd-NP led to co-localization of the catalyst with its prodrug substrate in the perinuclear cellular compartment (FIG. 12*a-b*), and caused a detectable increase of drug in the nucleus compared to the cytoplasm. This suggests that Pd-mediated prodrug activation leads to enhanced DNA association of the prodrug (FIG. 3*c*). HPLC fluorescence detection in lysate of treated cells confirmed a decrease in intracellular prodrug concentration when cells were co-treated with Pd-NP (FIG. 12*c-d*). Residual cytoplasmic/lysosomal accumulation of $C_{16}$proDOX was observed despite Pd-NP co-treatment, although this was also observed to some degree for DOX treatment as well (FIG. 3, 12). These results suggest successful intracellular activation of $C_{16}$proDOX by Pd-NP.

Figure 4A:
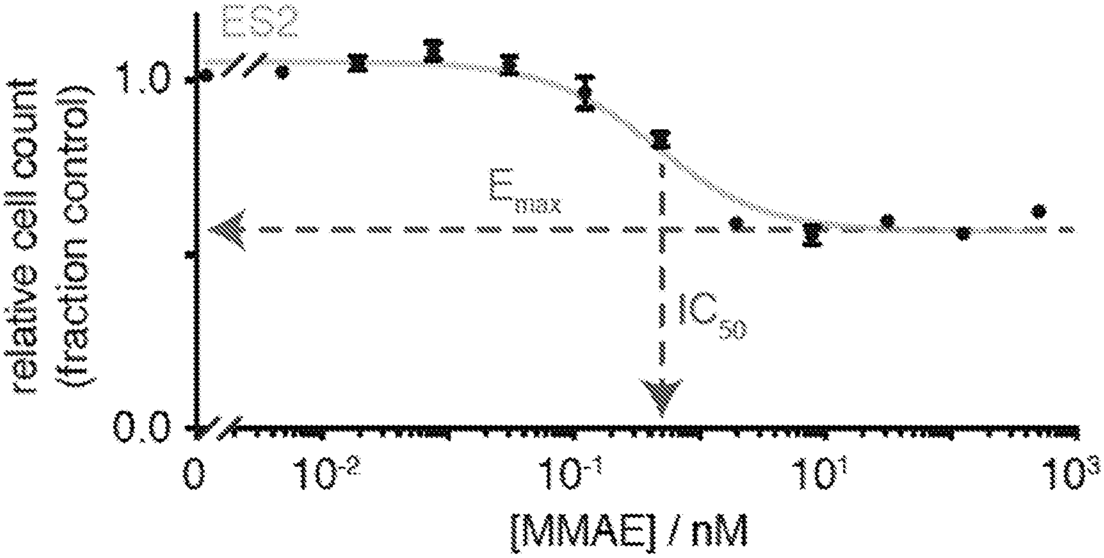
Figure 4B:
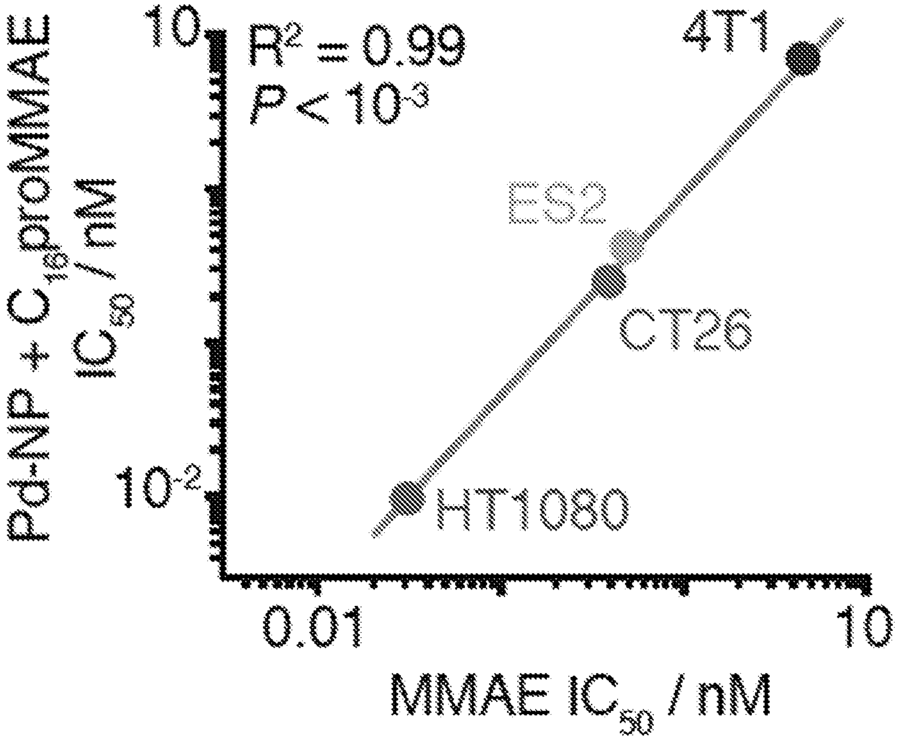
Figure 4C:
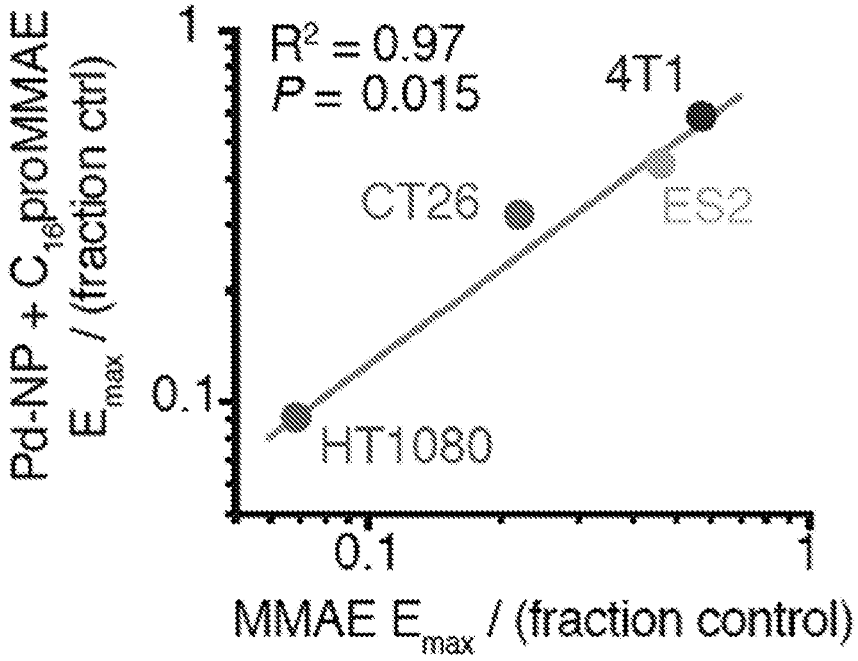

It was next studied how $C_{16}$proMMAE and its subsequent activation compares to the biological behavior of the parent compound MMAE, a well understood antimitotic agent that blocks the polymerization of tubulin and consequently inhibits cell division. Across a panel of 4 cancer cell lines, $C_{16}$proMMAE exhibited no detectable impact on cell growth at concentrations≤10 μM (FIG. 13*a*). However, its co-treatment with Pd-NP led to cytotoxic responses that closely mirrored those of the parent compound in terms of both the concentration at which 50% of the effect was observed ($IC_{50}$) and the maximum inhibitory effect that was achieved (Emax; FIG. 4*a-c*). Thus at the cellular level, $C_{16}$proMMAE behaves nearly identically to MMAE once activated by Pd-NP ($R^2$>0.95, FIG. 4*b-c*). Of note, Pd—NP by itself did not detectably impact cell growth at concentrations up to 50 μM for 3 of the 4 tested cell lines (FIG. 13*b*), consistent with past reports and its known safety profile.[5]

Figure 4D:
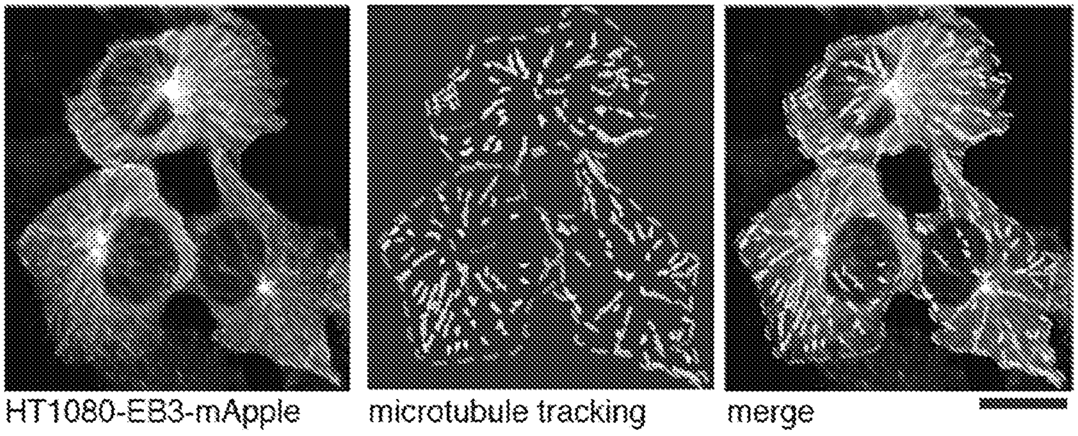
Figure 4E:
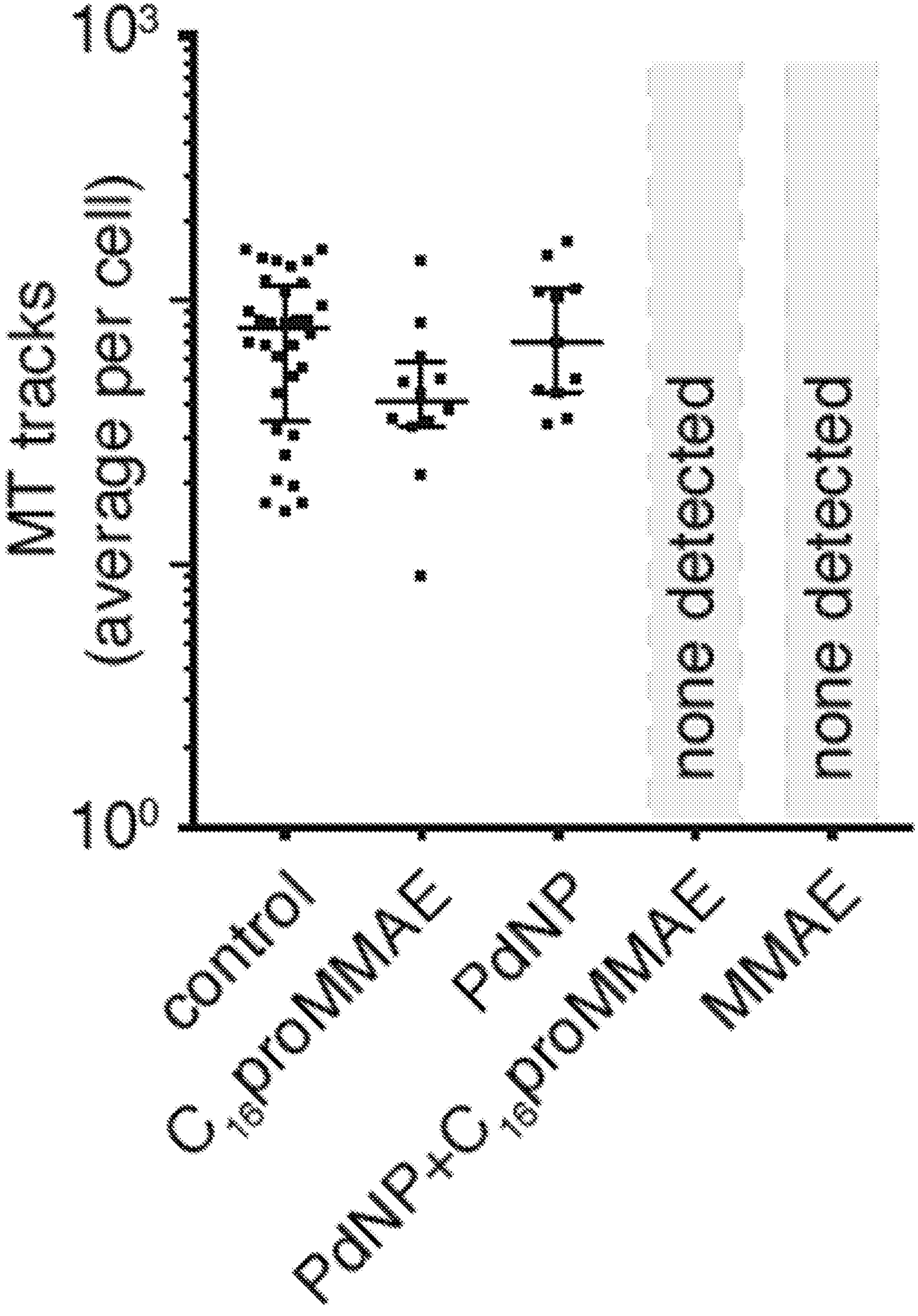
Figure 4F:
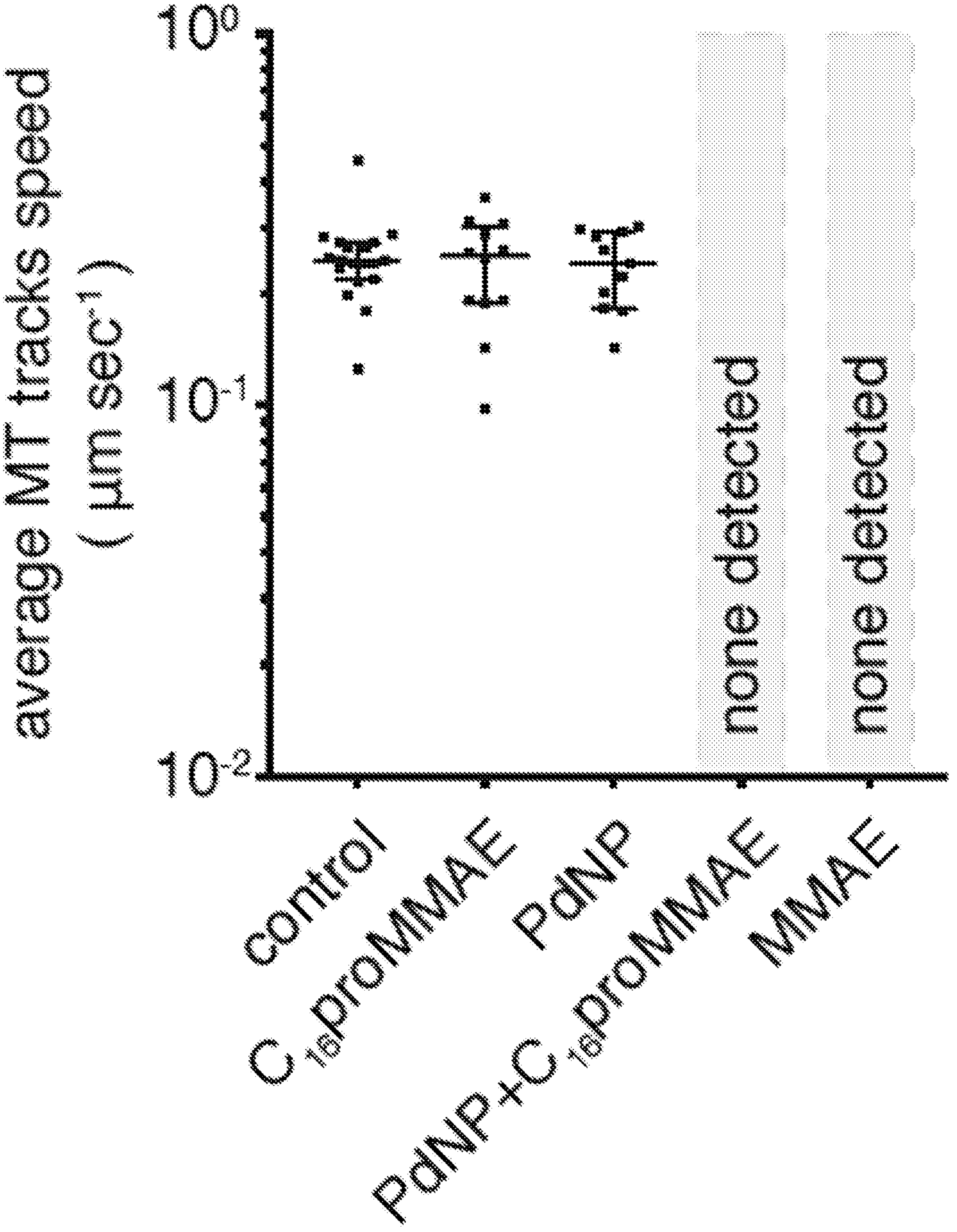

To examine $C_{16}$proMMAE effects at the molecular level, confocal microscopy of growing microtubule ends was used as a biomarker of drug actions in live cells. The HT1080 cancer cell line was engineered to transgenically express a red fluorescent fusion protein, EB3-mApple. The End-binding protein 3 (EB3) is also known as microtubule-associated protein RP/EB family member 3 (MAPRE3) and binds to the plus-end of growing microtubules (FIG. 4*d*). As a result, EB3-fluorescent protein fusions are widely used for studying microtubule dynamics in live cells, with plus-ends visible as microtubule "comets" transiting the cell.[17] HT1080-EB3-mApple cells displayed microtubule comets that were not substantially perturbed by individual treatment with either Pd-NP or $C_{16}$proMMAE, either according to microtubule comet prevalence in cells (FIG. 4*e*) or their growth speed (FIG. 4*f*). However, the combination of both led to complete elimination of visible comets, just as observed with the parent compound MMAE. LC/MS analysis confirmed Pd-NP causes generation of MMAE from the prodrug (FIG. 12). Together, these results suggest that MMAE caging was effective at preventing microtubule perturbation, and that activation by Pd-NP restored its microtubule disruption capacity (FIG. 4; FIG. 20).

Figure 5A:
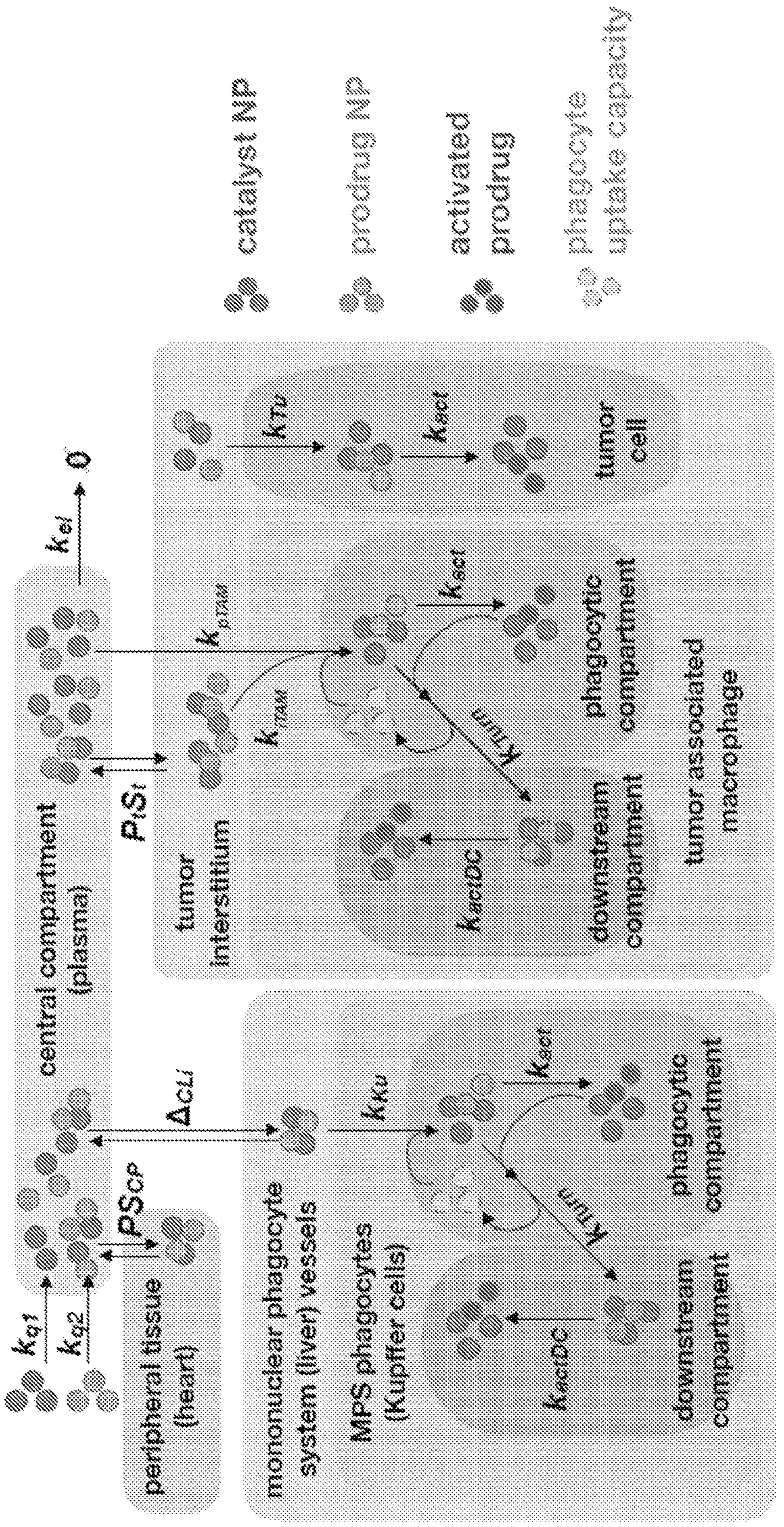
Figure 5B:
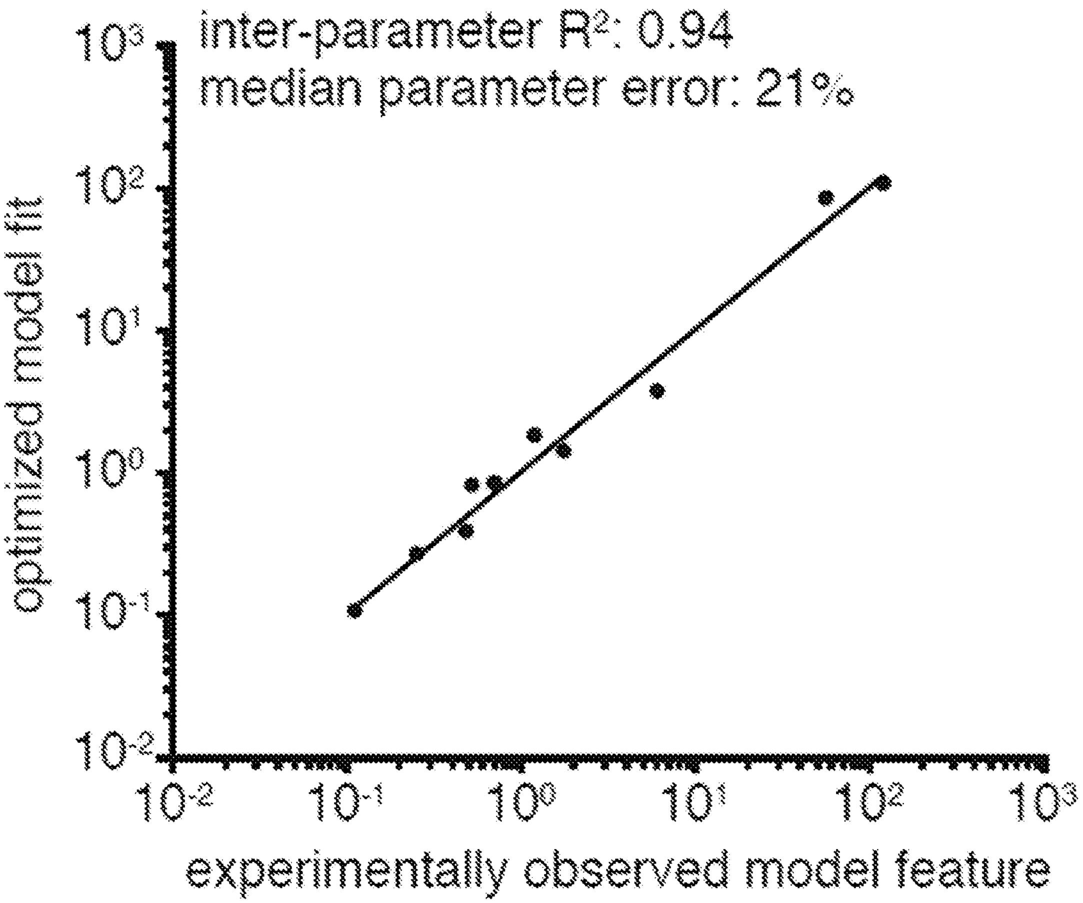
Figure 5C:
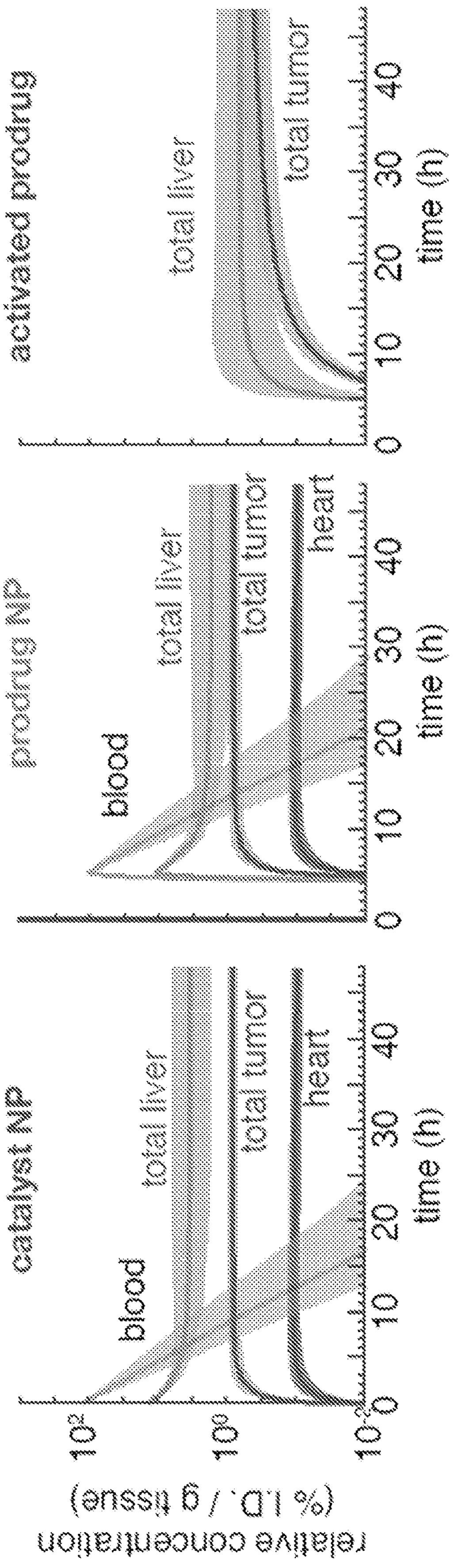
Figure 5D:
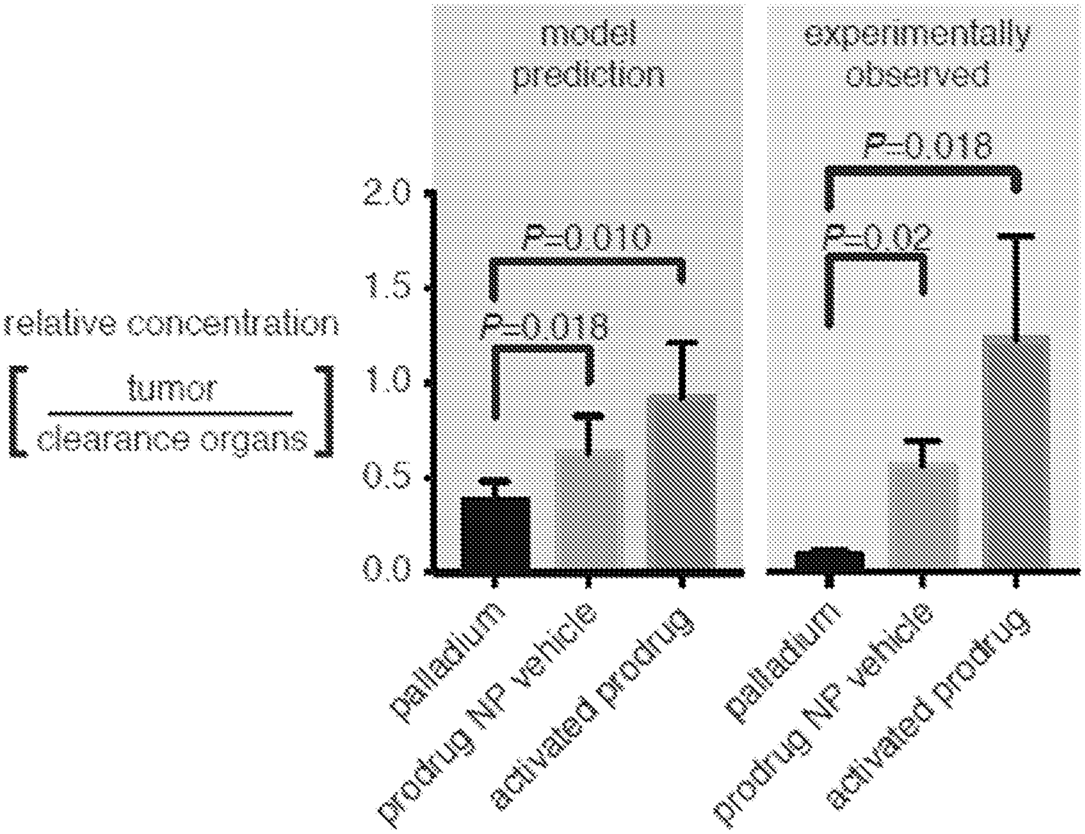
Figure 14B:
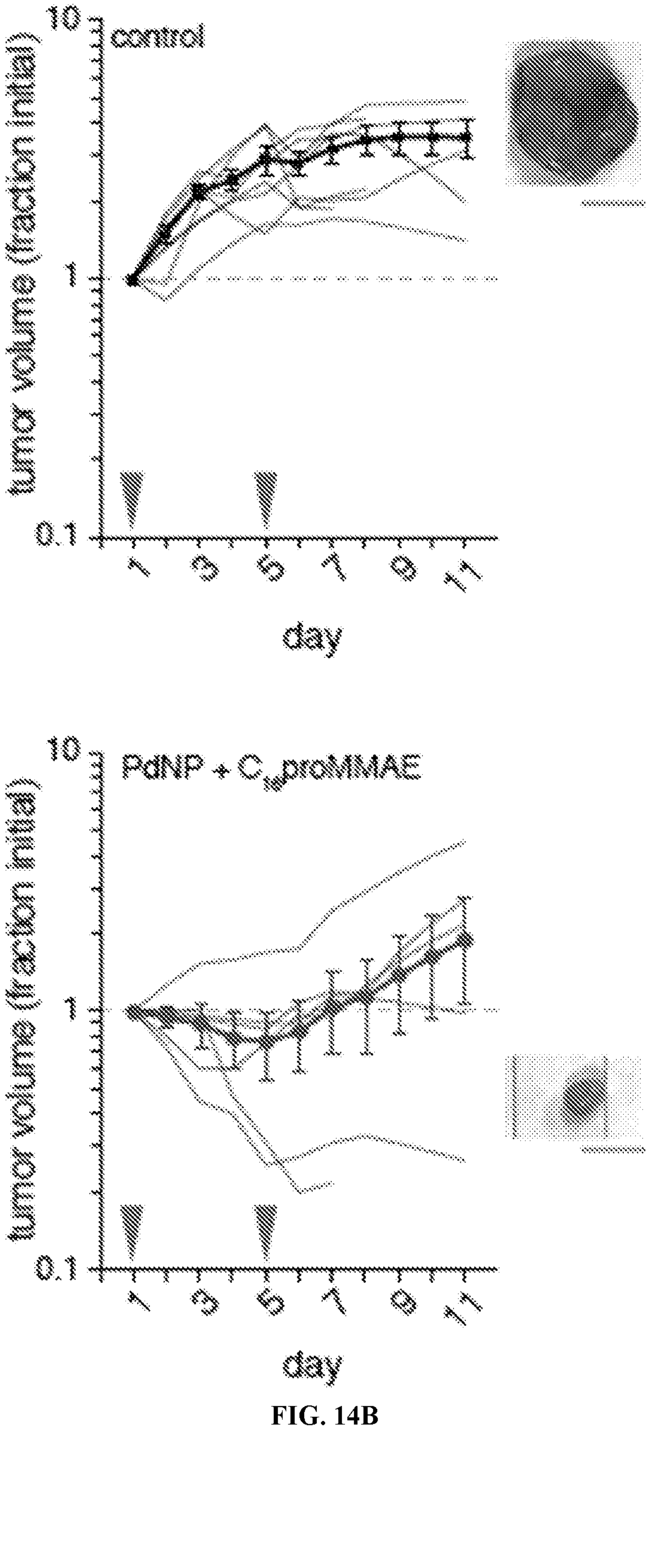
Figure 14C:
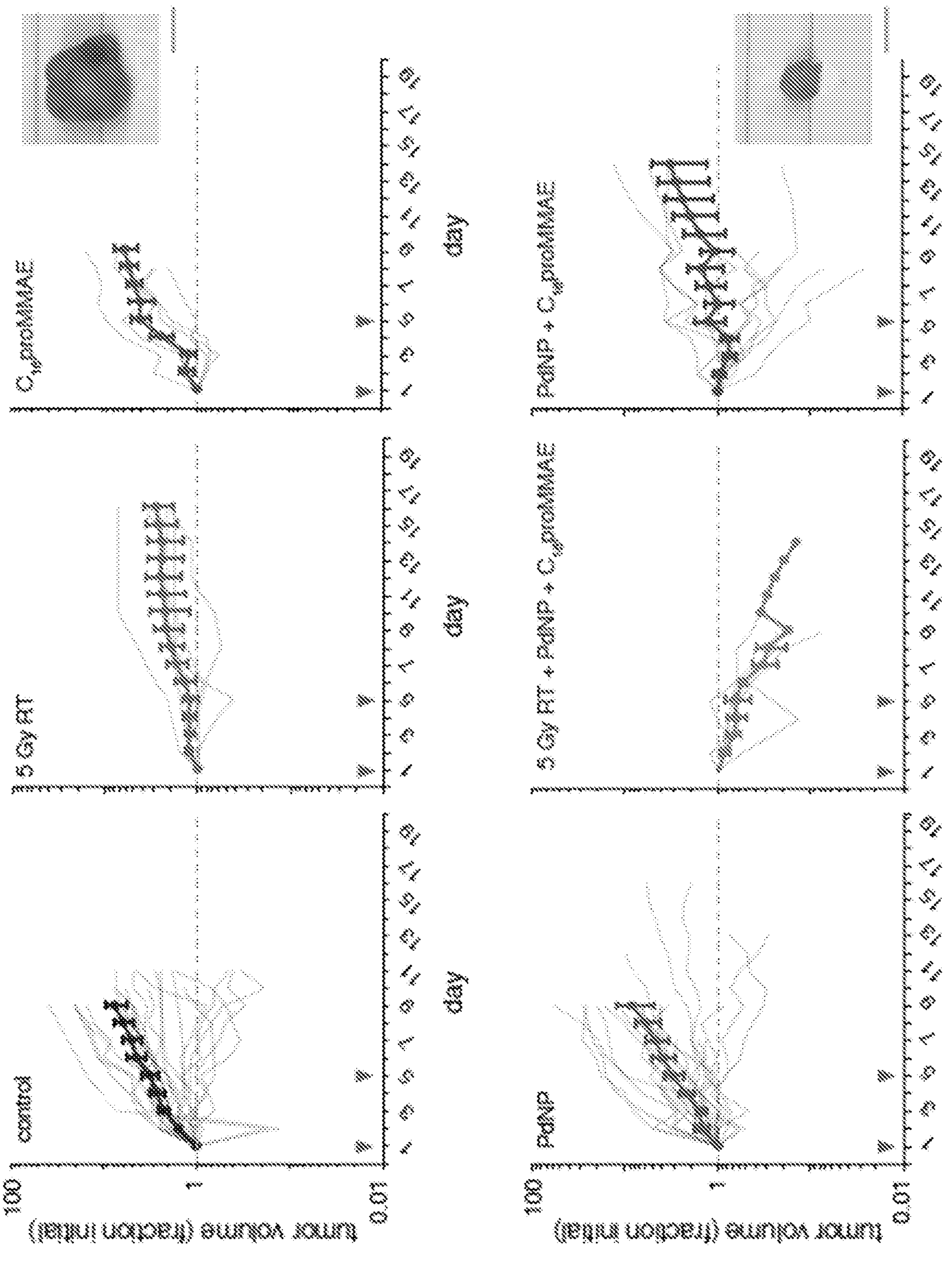

Example 9—Safety and Efficacy Using Human Xenograft and Syngeneic Mouse Models of Cancer Given the success of Pd-NP in activating $C_{16}$proMMAE, we next tested its ability to safely and effectively treat tumors in two complementary mouse models of cancer: subcutaneous HT1080 xenograft tumors in nu/nu mice, and MC38 murine colon adenocarcinoma tumors grown intradermally in immunocompetent C57BL/6 mice. Upon palpable tumor formation, HT1080-bearing animals were treated with doses of either Pd-NP, $C_{16}$proMMAE NP, or the combination of the two by intravenous injection. It was previously determined that staggering the administration of Pd-NP and a subsequent prodrug NP administration by several hours (as opposed to co-injecting both NPs together) could lead to more selective tumoral accumulation of activated prodrug.[5] Indeed, although Pd accumulates in the clearance organs (liver, spleen, and kidney) in mice bearing HT1080 tumors, staggered administration of the prodrug NP leads to comparably lower off-target accumulation of the activated prodrug, especially relative to levels of prodrug activation in the tumor (FIG. S7*a*).[5] Using the prescribed 5 h dose staggering scheme, the dual treatment of Pd-NP and $C_{16}$proMMAE NP successfully blocked tumor growth (FIG. 5*a*), while animals receiving either Pd-NP or $C_{16}$proMMAE NP as single-treatments saw no change in their tumor growth compared to the untreated cohort (FIG. 5*a*; P>0.05; also see ref. 5). Similarly, combined Pd-NP and $C_{16}$proMMAE treatment was effective at slowing tumor growth in the MC38 tumor model (FIG. 5*b*). In fact, in both models tumor growth was completely blocked at 2 days following the $2^{nd}$ round of Pd-NP and $C_{16}$proMMAE treatment (FIG. 5*c-d*). However, the treatment was not curative and a fraction of tumors eventually resumed growth (individual tumors growth curves are shown in FIG. 14*b-c*).

In vitro tests had demonstrated $C_{16}$proMMAE to be a much more potent drug once activated by Pd-NP, compared to doxorubicin-based formulations (FIG. 2). When compared to previously published results, the dual treatment with Pd-NP and $C_{16}$proMMAE performed at least as well as the combination of Pd-NP and Alloc-DOX NP, even at <2% the relative molar dose (0.8 μmol $kg^{-1}$ compared to 48 μmol $kg^{-1}$ of prodrug).[5] Control experiments using equivalent doses of parent MMAE were not performed, as it is known to be severely toxic and above the maximum tolerated dose in mouse models (e.g., see ref. 18). For these reasons, MMAE itself is not a cancer drug candidate and is only used as an antibody-drug conjugate or nanotherapeutic. In contrast, animals treated with dual Pd-NP and $C_{16}$proMMAE did not show drug-induced weight loss (FIG. 5*e-f*), and blood chemistry analysis of treated animals showed no signs of drug-induced liver or kidney toxicity (FIG. 5*g*). Thus, these results suggest that Pd-mediated activation of $C_{16}$proMMAE can safely and effectively block tumor growth.

Example 10—Modeling In Vivo Mechanisms of Dual Nanotherapy Action

Data reported here indicate that dual Pd-NP and prodrug-NP strategies can lead to more selective activation in the tumor compared to traditional solvent- and nano-formulations of the parent drug. In this work, the dual Pd-NP and $C_1$iproMMAE treatment was effective and well-tolerated. Previously, it was found that dual Pd-NP and Alloc-DOX treatment was similarly safe and effective (albeit requiring much higher prodrug doses for efficacy). In past head-to-head experiments using HT1080 xenografts, traditional solvent- and nano-formulations of active DOX both exhibited myelotoxicity at equimolar doses, while the dual Pd-NP and Alloc-DOX strategy did not.[5] Others have likewise reported that traditional DOX nanoencapsulation can fail to prevent myelotoxicity in mouse models of cancer.[19] Without being bound by theory, this disclosure discusses what mechanisms enable dual Pd-NP and prodrug treatment to more selectively activate in the tumor, particularly compared to other traditional nanoformulations.

Figure 6A:
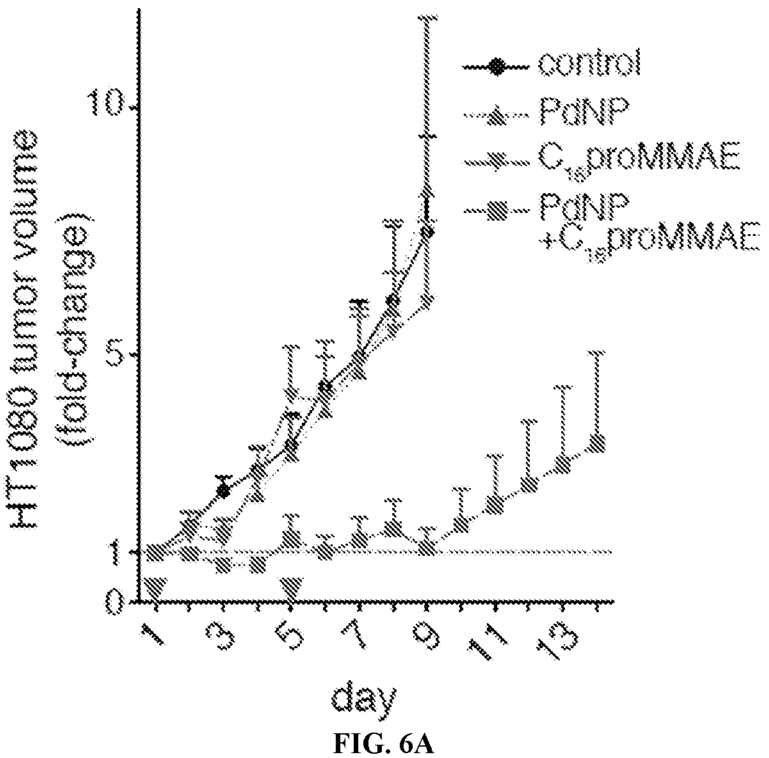
Figure 6B:
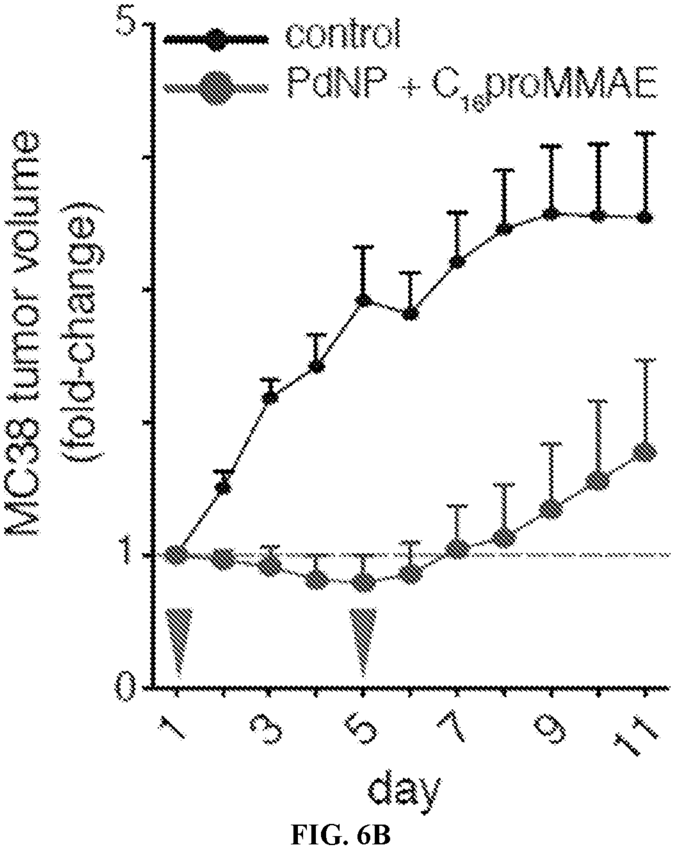

A computational multi-compartment model of pharmacokinetics and prodrug activation was developed (FIG. 6*a*). As with all such models, simplifications were made for both practical implementation and manageable interpretation, and we roughly based our study on prior models used for pharmacokinetic analysis of biologics and nanomaterials.[20-23] The model consists of 27 parameters (12 of which were optimized, 15 fixed from prior experimental data; Table 16), 30 ordinary differential equations (FIG. 17), and 4 primary organ-level compartments (FIG. 6*a*): the central compartment (plasma), peripheral tissue (simplified here as the heart, as a representative example with known drug toxicity concerns), the mononuclear phagocyte system (simplified here as the liver, which clears a large fraction of nanomaterials), and the tumor. Following distribution from vessels into tissue, NPs are taken up by phagocytes in the liver (Kupffer cells) and tumor (tumor-associated macrophages, TAMs) along with tumor cells themselves. Importantly, we modeled myeloid phagocytic capacity as saturable, based on prior data using Pd-NPs[5] as well as a host of studies examining the effects of nanomaterial "loading doses" on the phagocytic clearance of subsequently administered nanomaterials.[24-27] While TAMs were also modeled as saturable, tumor cells were not, on the basis of published experimental data indicating the latter accumulate lower NP levels on a per-cell basis, at a slower rate, and well below their saturation levels achieved in vitro compared to TAMs and Kupffer cells (see FIG. 18 for data and references). Despite differences in particular nanomaterial properties used in the "loading dose" studies, their overall findings are relatively consistent (see FIG. 18). Once taken up into cells, catalytic and prodrug NPs react to yield active drug. For simplification, degradation was modeled as gradual transport of NPs from endocytic/lysosomal compartments into "downstream compartments" that were much less conducive to drug activation (for instance as if the prodrug or Pd compound were metabolized into degradation products).

Figure 6C:
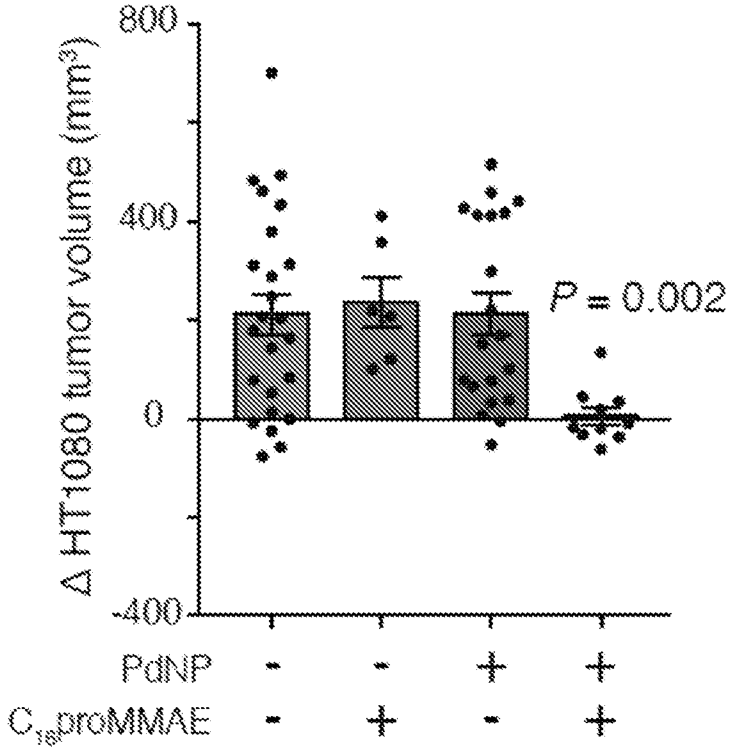
Figure 6D:
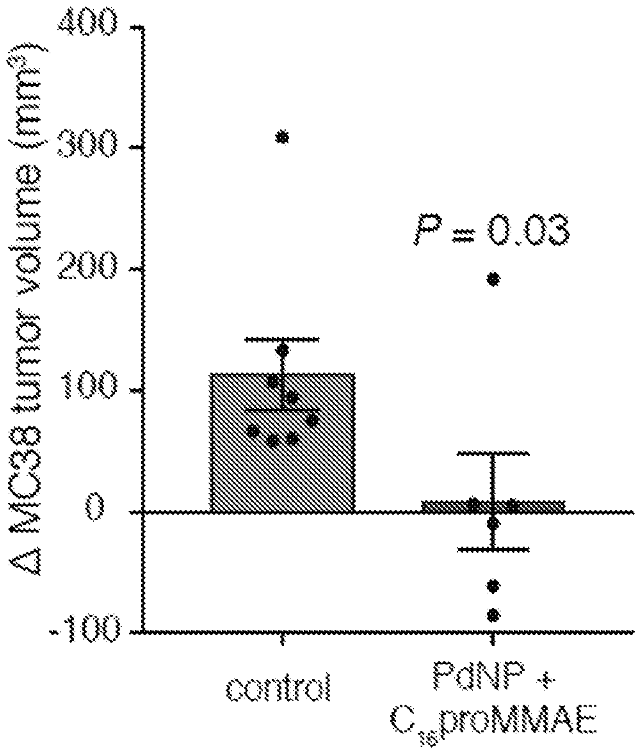
Figure 6E:
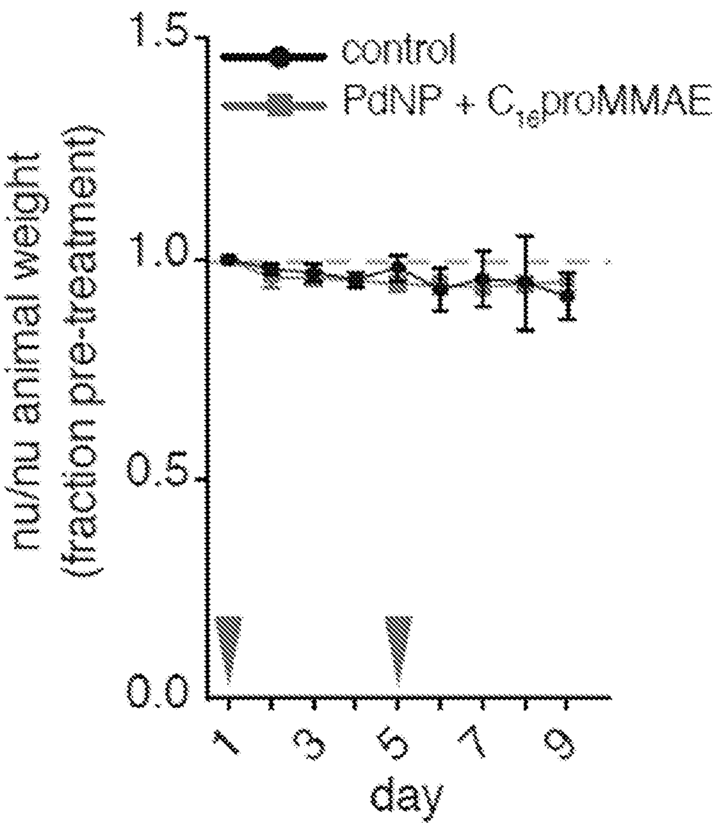
Figure 6F:
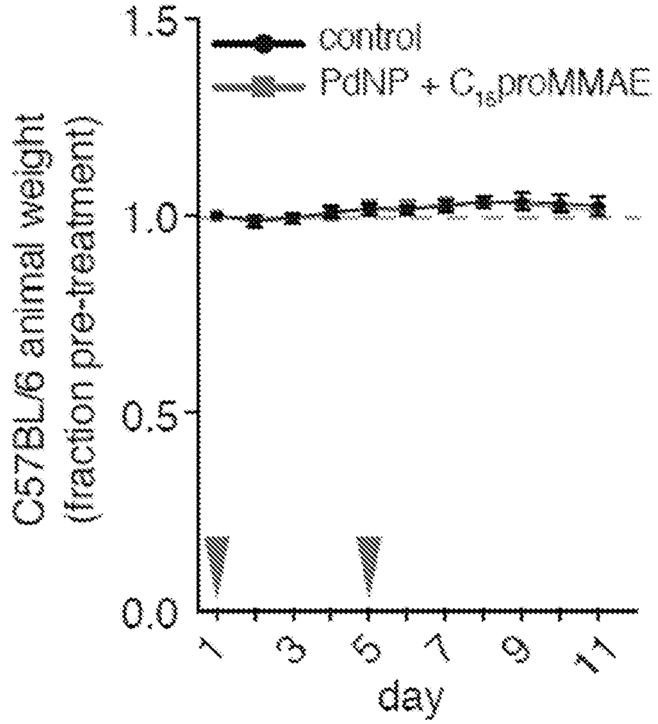
Figure 6G:
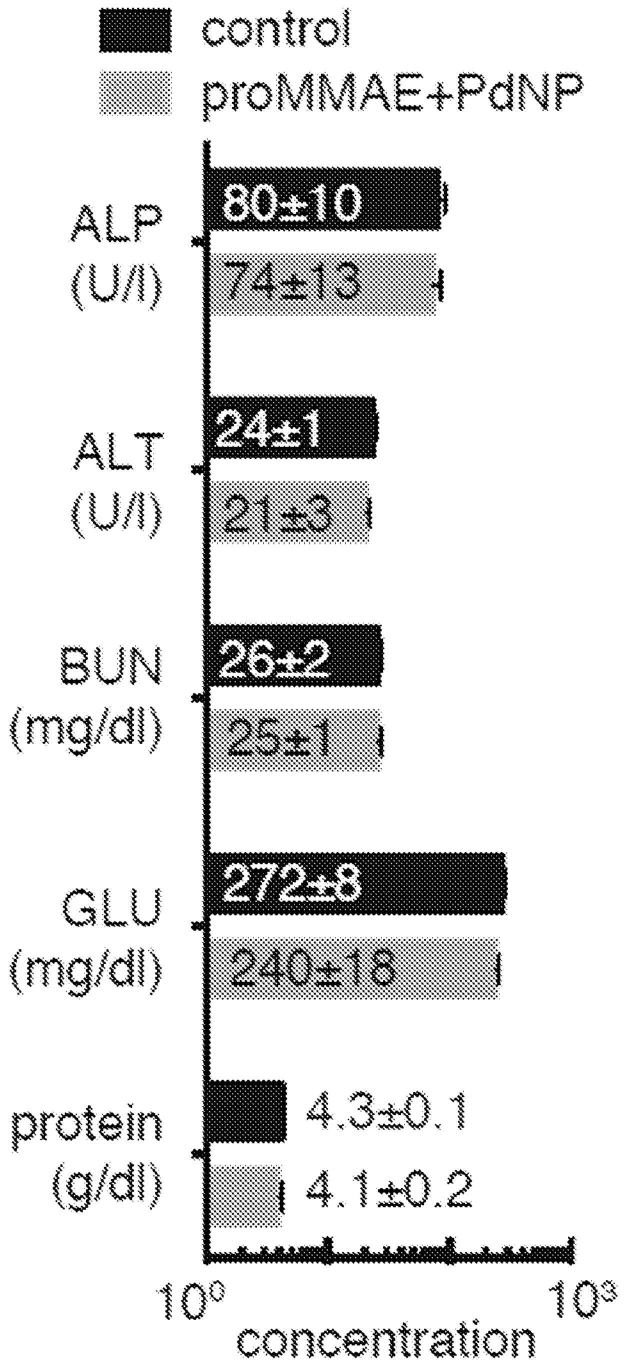
Figure 15:
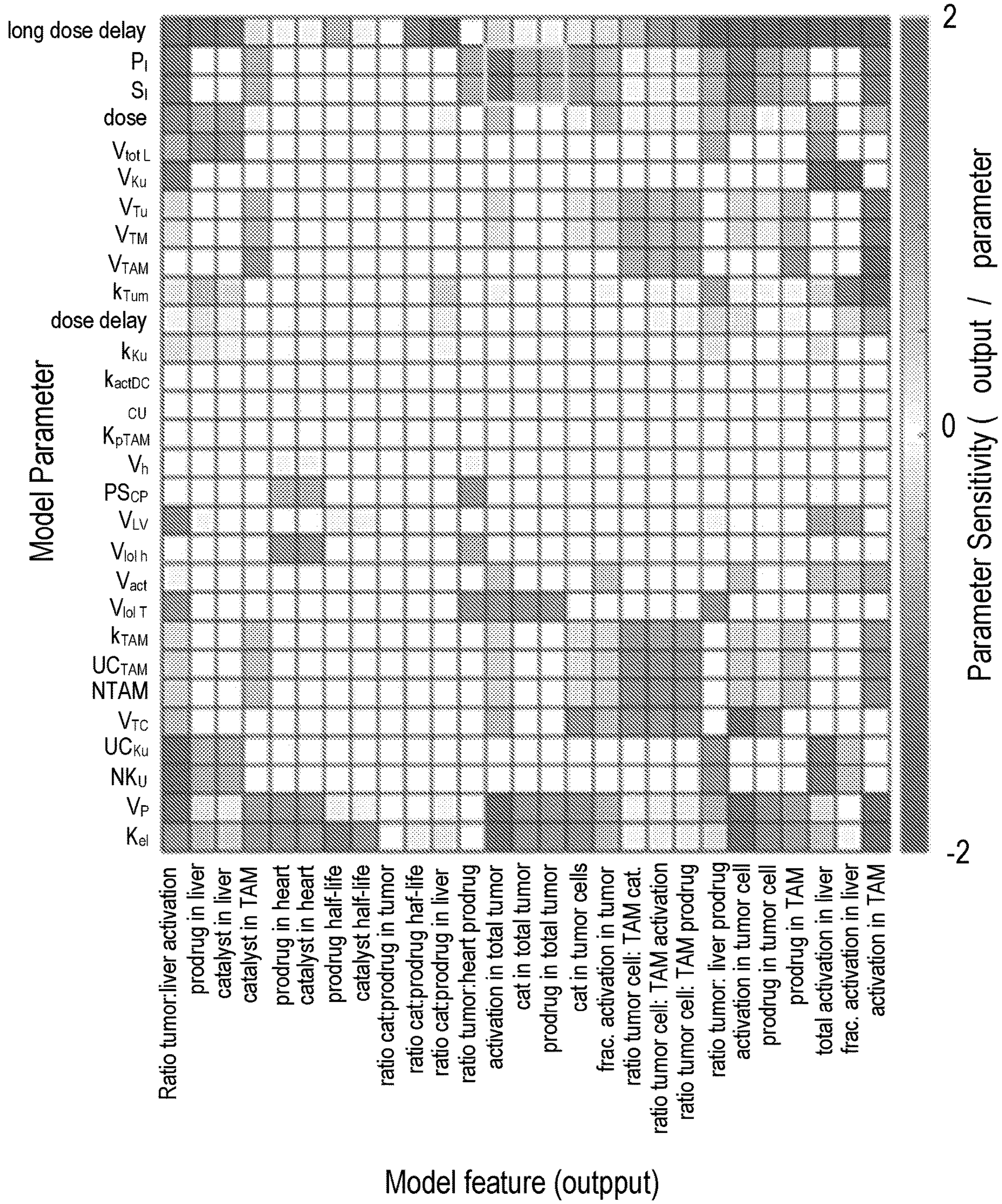

Parameters in the model were iteratively fit to 12 features derived from experimental data, most using the same HT1080 xenograft model and PLGA-PEG based nanoformulations described in this disclosure. In particular, the model was guided by i) time-lapse intravital microscopy of nanomaterial systemic clearance, extravasation, and cellular uptake in HT1080 tumors; ii) organ-level biodistribution measured by fluorescence (for fluorochrome-labeled NPs) and mass spectrometry (e.g., for Pd-NP), including in the HT1080 model; iii) cell-level biodistribution of fluorescent PLGA-PEG NPs measured by flow-cytometry; and iv) the relative ratios of catalytic NPs, prodrug NPs, and activated drug determined by fluorescence and/or mass spectrometry in the HT1080 models and loading dose studies (see FIG. 18). Overall, an ensemble of model results were compiled that showed a reasonable fit to the experimental data (FIG. 6*b*), with a median parameter error (19%) roughly within the biological uncertainty observed across the experimental data (average standard error 23%, FIG. 18). Pharmacokinetics and drug activation in the model accurately captured the time-staggered dosing of the catalyst- and prodrug-NPs (FIG. 6*c*). We performed a parametric sensitivity analysis to gauge how changing individual model parameters can influence overall system behavior (FIG. 15). From this analysis and an examination of the simulation results, an important trend was captured: through the combination of saturable phagocytic clearance in the liver (amplified through staggered NP administration), and compounded EPR effect in the tumor, drug activation was observed to be more selective in the tumor compared to distribution of the catalyst NP or its prodrug NP substrate (FIG. 6*d*). This trend was matched by experimental biodistribution data in the HT1080 model (FIG. 6*d*).

Figure 14D:
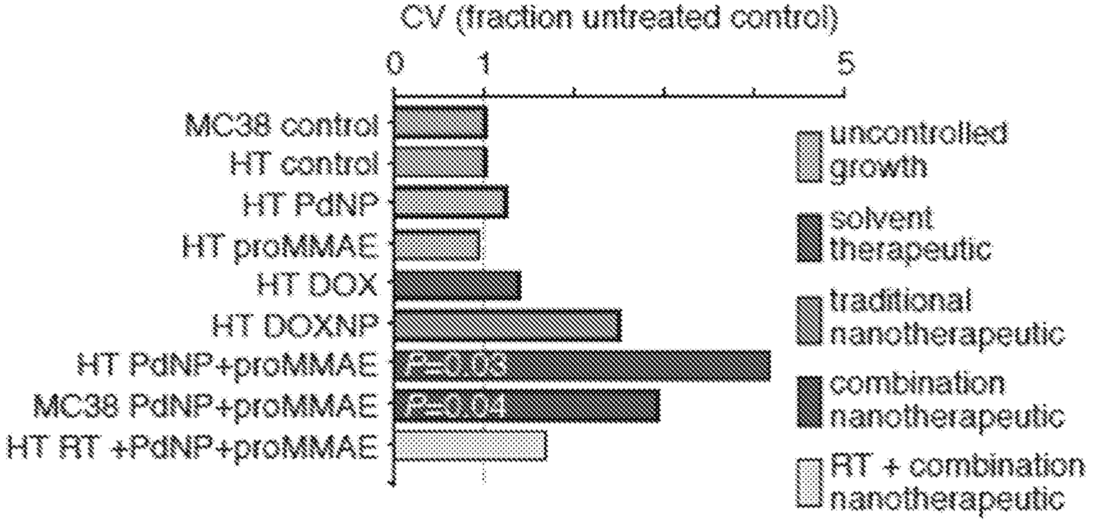
Figure 14E:
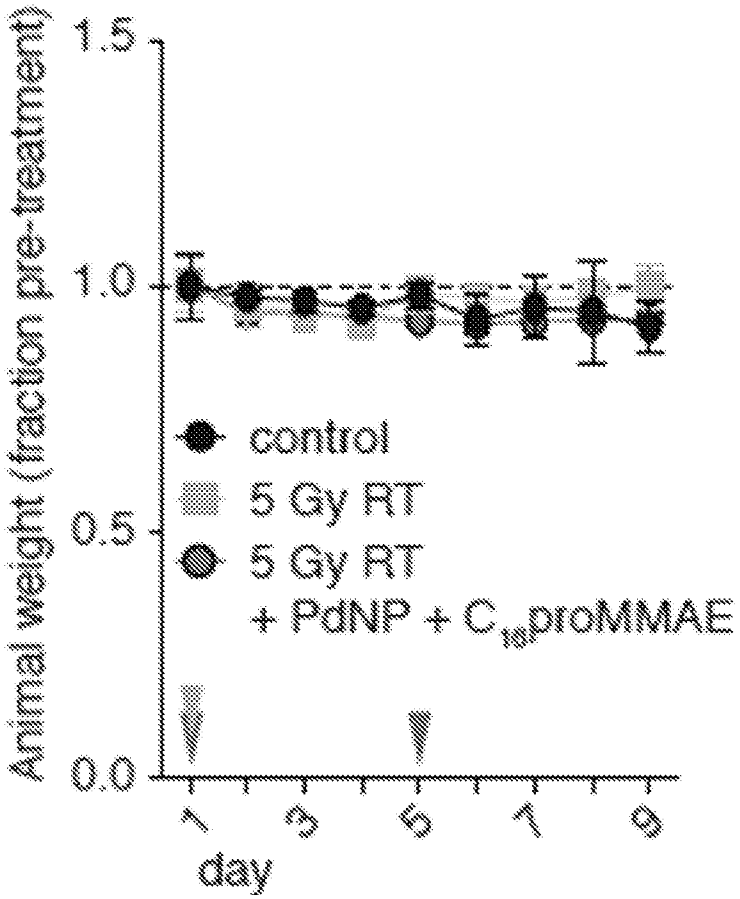

Example 11—Exploiting the Enhanced Reliance on EPR for Dual Nanotherapy Action Perhaps intuitively, the parametric sensitivity analysis of the computational model (FIG. 15) revealed that the bioorthogonal prodrug strategy relies to an especially high degree on factors related to the tumor EPR effect. As prime examples, the model suggests that changes in vascular permeability (Pt) and overall tumor vascularization (St) influence tumoral accumulation of active drug to a greater degree than accumulation of either the catalytic or prodrug NPs individually (highlighted in FIG. 15). Further experimental data underscores the strategy's susceptibility to variable EPR effects. Our recent studies have highlighted how the EPR effect is highly variable in the HT1080 tumor xenograft model.[28, 29] Closer examination of the tumor growth responses reveal that the dual Pd-NP and $C_{16}$proMMAE treatment leads to the most variable response of any other treatment, including to all controls, traditional single-nanotherapeutic treatments, and solvent-based treatments (FIG. 14*d*).

Figure 7A:
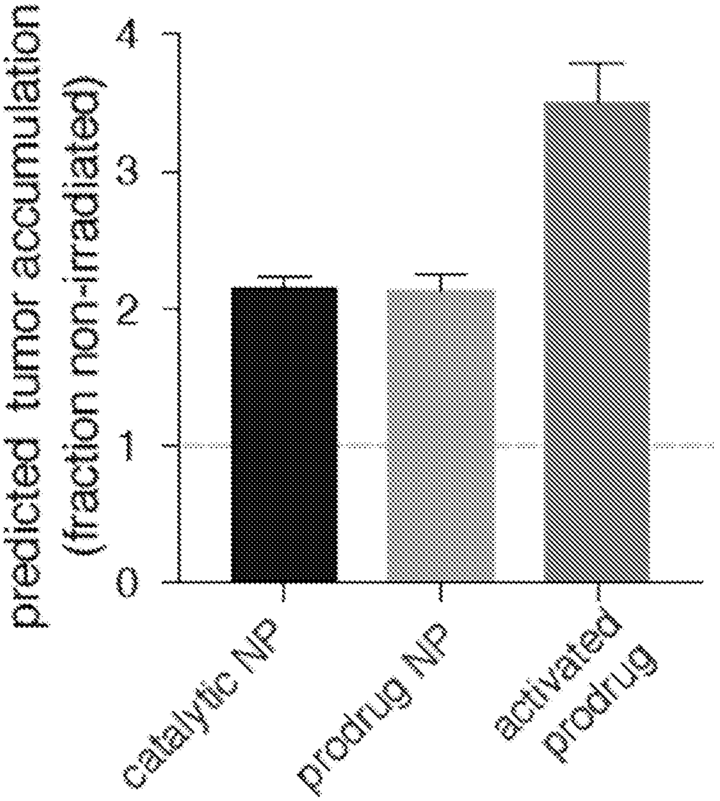
Figure 7B:
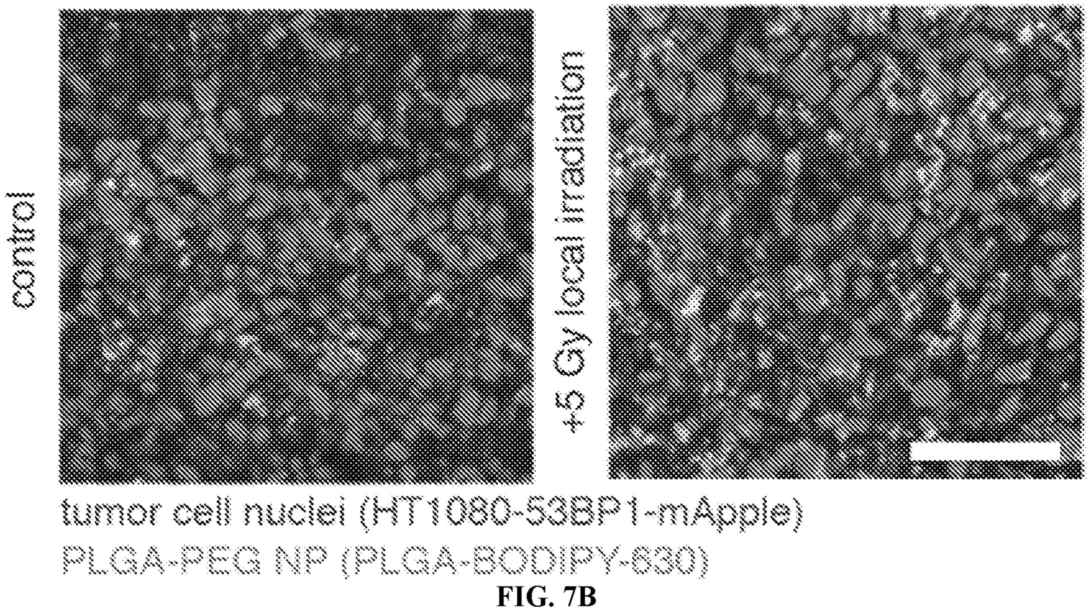
Figure 7C:
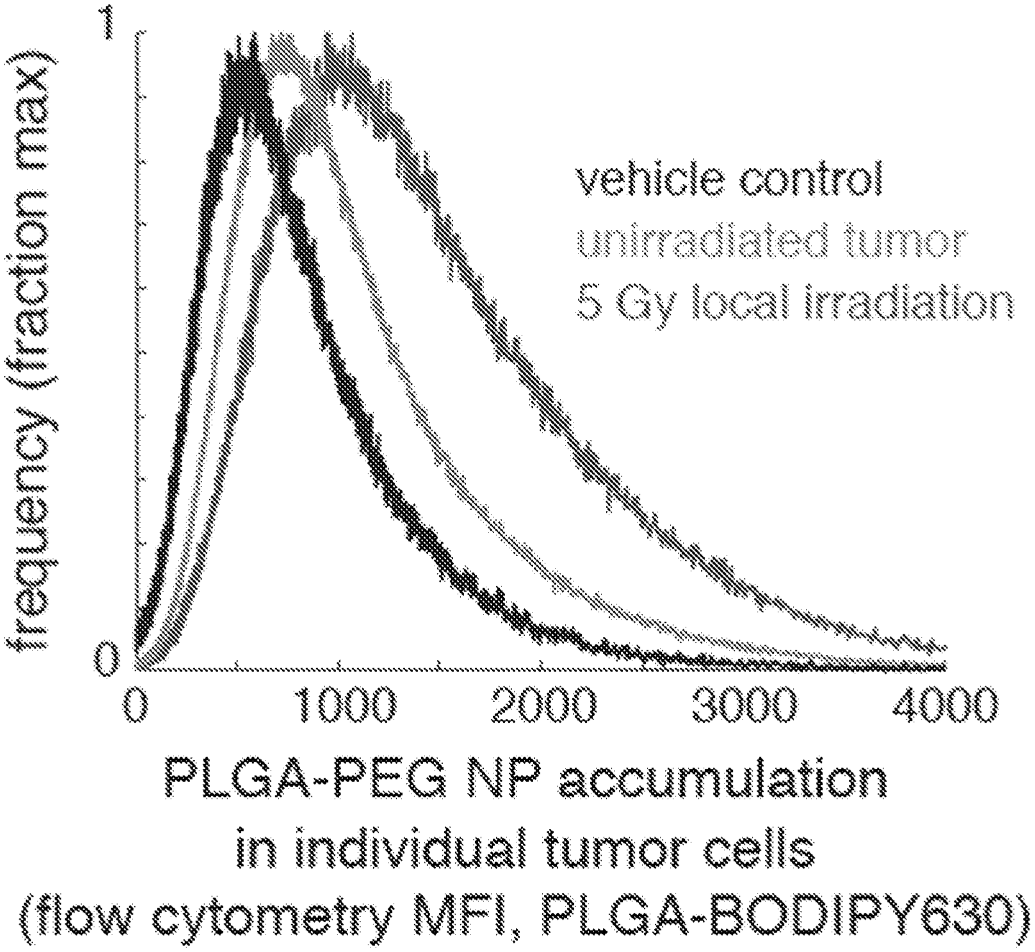
Figure 7D:
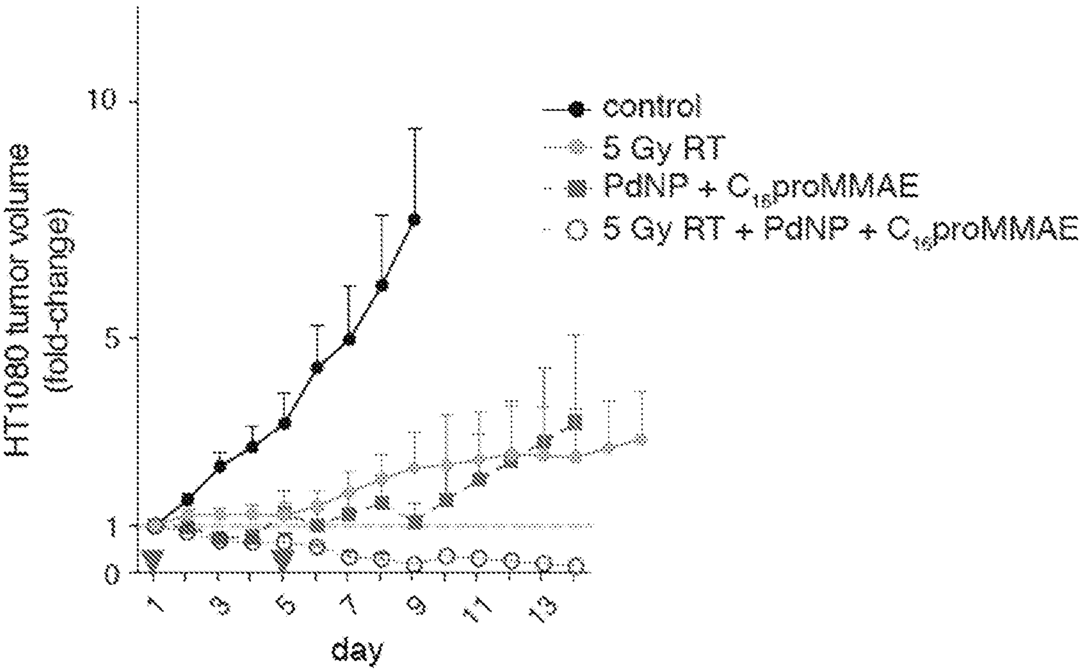
Figure 7E:
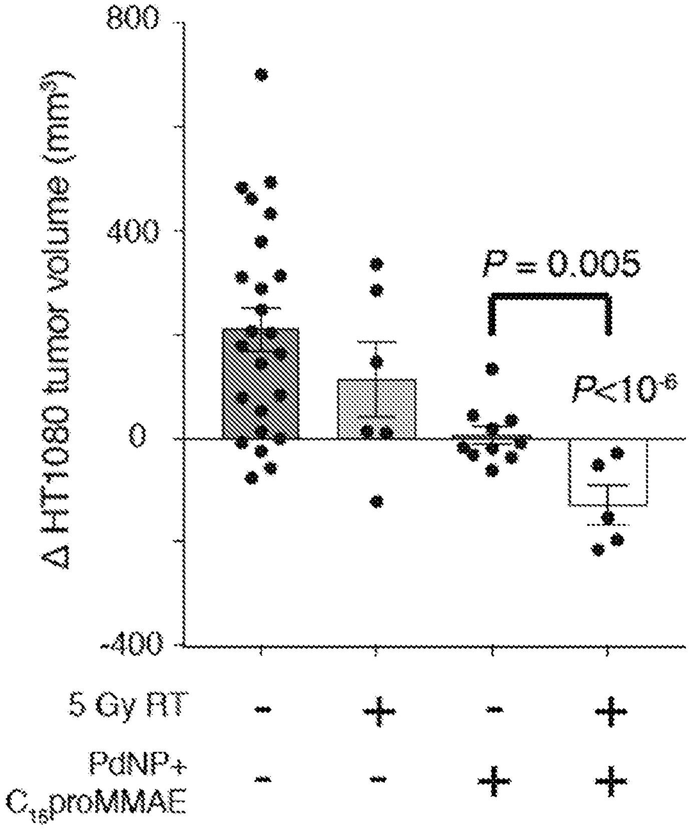

To overcome this variability, previous reports have shown that single low-dose tumor irradiation can increase NP accumulation via enhanced vascular permeability, TAM recruitment, and other physiological effects, and therefore considerably enhance EPR effects and NP efficacy in solid tumors.[30] To further improve efficacy, it was tested whether dual Pd-NP and $C_{16}$proMMAE NP treatment could benefit from such an approach. Based on measured impacts of such irradiation on vascular permeability (FIG. 18), the computational model predicted an especially responsive enhancement in drug activation, above the expected ~2-fold increase in NP accumulation (FIG. 7*a*). Indeed, HT1080 tumors exhibited greater accumulation of PLGA-PEG NP in the tumor following conformal 5 Gy gamma irradiation (the curative radiation dose is ~10× higher), as measured by confocal fluorescence microscopy (FIG. 7*b*) and flow cytometry (FIG. 7*c*). Although local tumor irradiation itself did not durably control tumor growth (as reported previously, ref. 30), it caused tumors to dramatically shrink when combined with the Pd-NP and $C_{16}$proMMAE NP treatment regimen (FIG. 7*d-e*), with no observed weight loss from irradiation (FIG. S7*e*). Notably, when radiation was added to the Pd-NP and $C_{16}$proMMAE treatment, the tumor responses no longer exhibited the same degree of heterogeneity that was seen without radiation (all tumors shrank, FIG. 14*d*). Overall, these results indicate that Pd-mediated $C_{16}$proMMAE activation is even more effective when tumors are conditioned by RT to accumulate greater levels of NPs.

Example 12—Comparison to Prior Prodrug Designs

This disclosure advances bioorthogonal chemistry applications by enabling multifunctional prodrug engineering for more efficient in vivo drug action delivered as NPs. Described herein is a modular design based on a multifunctional self-immolative linker that allows sterically bulky substituents (e.g., the aliphatic $C_{16}$ anchor) to be designed and utilized for tuning prodrug properties, while catalytic removal by a bioorthogonal Pd-NP catalyst (using the Alloc protecting group) efficiently restores drug activity. Compared to initial efforts in developing Pd-mediated prodrugs, this strategy led to development of $C_{16}$proMMAE, a NP-formulated prodrug with improvements including i) 100-fold greater turn-on capacity in cytotoxicity compared to Alloc-DOX (>70,000× turn-on for $C_{16}$proMMAE compared to ~700× for Alloc-DOX); ii) a roughly 100-fold greater in vitro potency compared to Alloc-DOX in the presence of Pd-NP; iii) a 50-fold reduction in the prodrug dose required for controlling tumor growth in vivo; and iv) highly efficient and stable nano-encapsulation properties. The approach is also able to take advantage of recent discoveries into how local radiation therapy can improve tumoral NP delivery and action, leading to synergistic response.[30] These results, and their comparison with traditional solvent- and nano-formulations of active drugs, are summarized in FIG. 19.

Prodrugs based on MMAE have a successful history in the clinic, largely based on their implementation in antibody drug conjugates (ADC) such as brentixumab vedotin (Adcetris), the anti-CD30 ADC used to treat refractory Hodgkin lymphoma among other indications. Other MMAE-based ADCs are undergoing clinical trials, while alternative microtubule-disrupting drugs are used in clinically-approved ADCs such as trastuzumab emtansine (Kadcyla). Although ADCs have demonstrated ability to extend survival in patients, they typically exhibit several drawbacks—primarily dose-limiting toxicities and incomplete tumor penetration—and ADC resistance is still common, especially in advanced malignancies. Toxicity arises from off-target ADC uptake; instability of the antibody-drug conjugation—especially when disulfide and hydrazone bonds are used—leading to systemic drug exposure; limited drug loading on antibodies; and poor ability to tightly control and decouple prodrug activation from antibody behavior. Limited efficacy may be due to low exposure of target cells, which is inevitable given the high molecular weight of antibodies. The bioorthogonal prodrug strategy presented here helps address some of these issues. In general, nano-encapsulation supports far greater prodrug loading capacity compared to antibodies. Use of a catalyst for prodrug activation offers the possibility of substoichiometric reactions, while use of a distinct bioorthogonal trigger (e.g., Pd-NP) can provide greater control over when and where the prodrug becomes activated, especially compared to prodrugs that rely on endogenous and often widely expressed enzymatic reactions, such as cathepsin proteases relied on by many ADCs.

CONCLUSIONS

The prodrug design concept presented in this work is especially suited for combinatorial NP delivery strategies, although other bioconjugation strategies (for instance, to antibodies or targeted small molecules) are feasible. The $C_{16}$ anchor used in the working examples could be replaced with other nano-encapsulation anchors, linkers to different types of molecular targeting entities, or other therapeutic payloads. In the context of Pd-NP bioorthogonal catalysis, nano-encapsulation has been shown to improve the stability, solubility, and selective in vivo delivery.[5] Selected examples described herein require accumulation of two different NPs in tumors. Hence the methods within the present claims, in some embodiments, are dependent on tumor uptake via the EPR effect, and this is underscored by the computational pharmacokinetic modeling results. Patients vary in how well their tumors accumulate NPs, but personalization of therapy may be feasible using biomarkers of NP uptake.[31] For instance, recent work has highlighted how an FDA-approved magnetic NP, ferumoxytol (Feraheme), can be used as an MRI contrast agent and companion diagnostic to identify tumors with high EPR, and to predict corresponding nanomedicine response.[28] This approach has been especially promising in predicting the clinical activity of a liposomal formulation of the prodrug irinotecan (Onivyde®), which was recently approved by the FDA for treatment of refractory pancreatic cancer.[32] Along these lines, local low-dose tumor irradiation, as used here, can enhance the EPR effect in a manner detectable by ferumoxytol imaging and leads to synergistic responses.[29] Furthermore, the data presented herein indicates that the $C_{16}$ nano-encapsulation anchor may block biological (i.e., cytotoxic) effects of the prodrug and influenced subcellular distribution.

REFERENCES (1) Li, J.; Chen, P. R. Development and Application of Bond Cleavage Reactions in Bioorthogonal Chemistry. *Nat. Chem. Biol.* 2016, 12, 129-137.
(2) Zhang, X.; Wang, B.; Zhao, N.; Tian, Z.; Dai, Y.; Nie, Y.; Tian, J.; Wang, Z.; Chen, X. Improved Tumor Targeting and Longer Retention Time of NIR Fluorescent Probes Using Bioorthogonal Chemistry. *Theranostics* 2017, 7, 3794-3802.
(3) Hapuarachchige, S.; Kato, Y.; Artemov, D. Bioorthogonal Two-Component Drug Delivery in HER2(+) Breast Cancer Mouse Models. *Sci. Rep.* 2016, 6, 24298.
(4) Klán, P.; Šolomek, T.; Bochet, C. G.; Blanc, A.; Givens, R.; Rubina, M.; Popik, V.; Kostikov, A.; Wirz, J. Photoremovable Protecting Groups in Chemistry and Biology: Reaction Mechanisms and Efficacy. *Chem. Rev.* 2013, 113, 119-191.

(5) Miller, M. A.; Askevold, B.; Mikula, H.; Kohler, R. H.; Pirovich, D.; Weissleder, R. Nano-Palladium is a Cellular Catalyst for In Vivo Chemistry. *Nat. Commun.* 2017, 8, 15906.

(6) Völker, T.; Meggers, E. Chemical Activation in Blood Serum and Human Cell Culture: Improved Ruthenium Complex for Catalytic Uncaging of Alloc-Protected Amines. *Chembiochem* 2017, 18, 1083-1086.

(7) Li, J.; Yu, J.; Zhao, J.; Wang, J.; Zheng, S.; Lin, S.; Chen, L.; Yang, M.; Jia, S.; Zhang, X.; Chen, P. R. Palladium-Triggered Deprotection Chemistry for Protein Activation in Living Cells. *Nat. Chem.* 2014, 6, 352-361.

(8) Pérez-López, A. M.; Rubio-Ruiz, B.; Sebastián, V.; Hamilton, L.; Adam, C.; Bray, T. L.; Irusta, S.; Brennan, P. M.; Lloyd-Jones, G. C.; Sieger, D.; Santamaria, J.; Unciti-Broceta, A. Gold-Triggered Uncaging Chemistry in Living Systems. *Angew. Chem. Int. Ed. Engl.* 2017, 56, 12548-12552.

(9) Versteegen, R. M.; Rossin, R.; ten Hoeve, W.; Janssen, H. M.; Robillard, M. S. Click to Release: Instantaneous Doxorubicin Elimination Upon Tetrazine Ligation. *Angew. Chem. Int. Ed. Engl.* 2013, 52, 14112-14116.

(10) Matikonda, S. S.; Orsi, D. L.; Staudacher, V.; Jenkins, I. A.; Fiedler, F.; Chen, J.; Gamble, A. B. Bioorthogonal Prodrug Activation Driven By a Strain-Promoted 1, 3-Dipolar Cycloaddition. *Chem. Sci.* 2015, 6, 1212-1218.

(11) Weiss, J. T.; Dawson, J. C.; Macleod, K. G.; Rybski, W.; Fraser, C.; Torres-Sánchez, C.; Patton, E. E.; Bradley, M.; Carragher, N. O.; Unciti-Broceta, A. Extracellular Palladium-Catalysed Dealkylation of 5-Fluoro-1-Propargyl-Uracil as a Bioorthogonally Activated Prodrug Approach. *Nat. Commun.* 2014, 5, 3277.

(12) Rubio-Ruiz, B.; Weiss, J. T.; Unciti-Broceta, A. Efficient Palladium-Triggered Release of Vorinostat From a Bioorthogonal Precursor. *J Med. Chem.* 2016, 59, 9974-9980.

(13) Yameen, B.; Choi, W. I.; Vilos, C.; Swami, A.; Shi, J.; Farokhzad, O. C. Insight Into Nanoparticle Cellular Uptake and Intracellular Targeting. *J Control. Release* 2014, 190, 485-499.

(14) Miller, M. A.; Zheng, Y R.; Gadde, S.; Pfirschke, C.; Zope, H.; Engblom, C.; Kohler, R. H.; Iwamoto, Y.; Yang, K. S.; Askevold, B.; Kolishetti, N.; Pittet, M.; Lippard, S. J.; Farokhzad, O. C.; Weissleder, R. Tumour-Associated Macrophages Act as a Slow-Release Reservoir of Nano-Therapeutic Pt(IV) Pro-Drug. *Nat. Commun.* 2015, 6, 8692.

(15) Zhang, X.; Zeng, X.; Liang, X.; Yang, Y.; Li, X.; Chen, H.; Huang, L.; Mei, L.; Feng, S. S. The Chemotherapeutic Potential of PEG-B-PLGA Copolymer Micelles That Combine Chloroquine as Autophagy Inhibitor and Docetaxel as an Anti-Cancer Drug. *Biomaterials* 2014, 35, 9144-9154.

(16) Zhang, J.; Chang, D.; Yang, Y.; Zhang, X.; Tao, W.; Jiang, L.; Liang, X.; Tsai, H.; Huang, L.; Mei, L. Systematic Investigation on the Intracellular Trafficking Network of Polymeric Nanoparticles. *Nanoscale* 2017, 9, 3269-3282.

(17) Stepanova, T.; Slemmer, J.; Hoogenraad, C. C.; Lansbergen, G.; Dortland, B.; De Zeeuw, C. I.; Grosveld, F.; van Cappellen, G.; Akhmanova, A.; Galjart, N. Visualization of Microtubule Growth in Cultured Neurons Via the Use of Eb3-Gfp (End-Binding Protein 3-Green Fluorescent Protein). *J. Neurosci.* 2003, 23, 2655-2664.

(18) Legigan, T.; Clarhaut, J.; Tranoy-Opalinski, I.; Monvoisin, A.; Renoux, B.; Thomas, M.; Le Pape, A.; Lerondel, S.; Papot, S. The First Generation of B-Galactosidase-Responsive Prodrugs Designed for the Selective Treatment of Solid Tumors in Prodrug Monotherapy. *Angew. Chem. Int. Ed. Engl.* 2012, 51, 11606-11610.

(19) Xu, R.; Zhang, G.; Mai, J.; Deng, X.; Segura-Ibarra, V.; Wu, S.; Shen, J.; Liu, H.; Hu, Z.; Chen, L.; Huang, Y.; Koay, E.; Huang, Y.; Liu, J.; Ensor, J. E.; Blanco, E.; Liu, X.; Ferrari, M.; Shen, H. An Injectable Nanoparticle Generator Enhances Delivery of Cancer Therapeutics. *Nat. Biotechnol.* 2016, 34, 414-418.

(20) Baxter, L. T.; Zhu, H.; Mackensen, D. G.; Jain, R. K. Physiologically Based Pharmacokinetic Model for Specific and Nonspecific Monoclonal Antibodies and Fragments in Normal Tissues and Human Tumor Xenografts in Nude Mice. *Cancer Res.* 1994, 54, 1517-1528.

(21) Schluep, T.; Hwang, J.; Hildebrandt, I. J.; Czernin, J.; Choi, C. H.; Alabi, C. A.; Mack, B. C.; Davis, M. E. Pharmacokinetics and Tumor Dynamics of the Nanoparticle IT-101 From Pet Imaging and Tumor Histological Measurements. *Proc. Natl. Acad. Sci. U.S.A* 2009, 106, 11394-11399.

(22) Hendriks, B. S.; Reynolds, J. G.; Klinz, S. G.; Geretti, E.; Lee, H.; Leonard, S. C.; Gaddy, D. F.; Espelin, C. W.; Nielsen, U. B.; Wickham, T. J. Multiscale Kinetic Modeling of Liposomal Doxorubicin Delivery Quantifies the Role of Tumor and Drug-Specific Parameters in Local Delivery to Tumors. C.P.T Pharmacometrics Syst. *Pharmacol.* 2012, 1, e15.

(23) Miller, M. A.; Moss, M. L.; Powell, G.; Petrovich, R.; Edwards, L.; Meyer, A. S.; Griffith, L. G.; Lauffenburger, D. A. Targeting Autocrine HB-EGF Signaling With Specific ADAM12 Inhibition Using Recombinant ADAM12 Prodomain. *Sci. Rep.* 2015, 5, 15150.

(24) Sun, X.; Yan, X.; Jacobson, O.; Sun, W.; Wang, Z.; Tong, X.; Xia, Y.; Ling, D.; Chen, X. Improved Tumor Uptake By Optimizing Liposome Based Res Blockade Strategy. *Theranostics* 2017, 7, 319-328.

(25) Jang, D. J.; Moon, C.; Oh, E. Improved Tumor Targeting and Antitumor Activity of Camptothecin Loaded Solid Lipid Nanoparticles By Preinjection of Blank Solid Lipid Nanoparticles. *Biomed. Pharmacother.* 2016, 80, 162-172.

(26) Liu, L.; Hitchens, T. K.; Ye, Q.; Wu, Y.; Barbe, B.; Prior, D. E.; Li, W. F.; Yeh, F. C.; Foley, L. M.; Bain, D. J.; Ho, C. Decreased Reticuloendothelial System Clearance and Increased Blood Half-Life and Immune Cell Labeling for Nano- and Micron-Sized Superparamagnetic Iron-Oxide Particles Upon Pre-Treatment With Intralipid. *Biochim. Biophys. Acta* 2013, 1830, 3447-3453.

(27) Liu, L.; Ye, Q.; Lu, M.; Lo, Y. C.; Hsu, Y. H.; Wei, M. C.; Chen, Y. H.; Lo, S. C.; Wang, S. J.; Bain, D. J.; Ho, C. A New Approach to Reduce Toxicities and to Improve Bioavailabilities of Platinum-Containing Anti-Cancer Nanodrugs. *Sci. Rep.* 2015, 5, 10881.

(28) Miller, M. A.; Gadde, S.; Pfirschke, C.; Engblom, C.; Sprachman, M. M.; Kohler, R. H.; Yang, K. S.; Laughney, A. M.; Wojtkiewicz, G.; Kamaly, N.; Bhonagiri, S.; Pittet, M. J.; Farokhzad, O. C.; Weissleder, R. Predicting Therapeutic Nanomedicine Efficacy Using a Companion Magnetic Resonance Imaging Nanoparticle. *Sci. Transl. Med.* 2015, 7, 314ra183.

(29) Miller, M. A.; Arlauckas, S.; Weissleder, R. Prediction of Anti-Cancer Nanotherapy Efficacy By Imaging. *Nanotheranostics* 2017, 1, 296-312.

(30) Miller, M. A.; Chandra, R.; Cuccarese, M. F.; Pfirschke, C.; Engblom, C.; Stapleton, S.; Adhikary, U.; Kohler, R. H.; Mohan, J. F.; Pittet, M. J.; Weissleder, R. Radiation Therapy Primes Tumors for Nanotherapeutic Delivery Via Macrophage-Mediated Vascular Bursts. *Sci. Transl. Med.* 2017, 9, eaal0225.

(31) Shi, J.; Kantoff, P. W.; Wooster, R.; Farokhzad, O. C. Cancer Nanomedicine: Progress, Challenges and Opportunities. *Nat. Rev Cancer* 2017, 17, 20-37.

(32) Ramanathan, R. K.; Kom, R. L.; Raghunand, N.; Sachdev, J. C.; Newbold, R. G.; Jameson, G.; Fetterly, G. J.; Prey, J.; Klinz, S. G.; Kim, J.; Cain, J.; Hendriks, B. S.; Drummond, D. C.; Bayever, E.; Fitzgerald, J. B. Correlation Between Ferumoxytol Uptake in Tumor Lesions By MRI and Response to Nanoliposomal Irinotecan in Patients With Advanced Solid Tumors: A Pilot Study. *Clin. Cancer Res.* 2017, 23, 3638-3648.

(33) Arlauckas, S. P.; Garris, C. S.; Kohler, R. H.; Kitaoka, M.; Cuccarese, M. F.; Yang, K. S.; Miller, M. A.; Carlson, J. C.; Freeman, G. J.; Anthony, R. M.; Weissleder, R.; Pittet, M. J. In Vivo Imaging Reveals a Tumor-Associated Macrophage-Mediated Resistance Pathway in Anti-PD-1 Therapy. *Sci. Transl. Med.* 2017, 9, eaal3604.

(34) Albright, C. F.; Graciani, N.; Han, W.; Yue, E.; Stein, R.; Lai, Z.; Diamond, M.; Dowling, R.; Grimminger, L.; Zhang, S. Y.; Behrens, D.; Musselman, A.; Bruckner, R.; Zhang, M.; Jiang, X.; Hu, D.; Higley, A.; Dimeo, S.; Rafalski, M.; Mandlekar, S. et al. Matrix Metalloproteinase-Activated Doxorubicin Prodrugs Inhibit HT1080 Xenograft Growth Better Than Doxorubicin With Less Toxicity. *Mol. Cancer Ther.* 2005, 4, 751-760.

(35) Applegate, K. T.; Besson, S.; Matov, A.; Bagonis, M. H.; Jaqaman, K.; Danuser, G. Plustiptracker: Quantitative Image Analysis Software for the Measurement of Microtubule Dynamics. *J. Struct. Biol.* 2011, 176, 168-184.

(36) Miller, M. A.; Askevold, B.; Yang, K. S.; Kohler, R. H.; Weissleder, R. Platinum Compounds for High-Resolution In Vivo Cancer Imaging. *ChemMedChem* 2014, 9, 1131-1135.

(37) Venkatesan, A. M.; Smith, R. A.; Damle, N. K.; Bakshi, R. K.; Odedra, A. V.; Kumar, S. Self-Immolative Linkers Containing Mandelic Acid Derivatives, Drug-Ligand Conjugates for Targeted Therapies and Uses Thereof WO 2015/038426, PCT/US2014/054236, Mar. 19, 2015.

(38) Miller, M. A.; Askevold, B.; Mikula, H.; Kohler, R. H.; Pirovich, D.; Weissleder, R. Nano-Palladium is a Cellular Catalyst for In Vivo Chemistry. *Nat Commun* 2017, 8, 15906.

(39) Hettrick, C. M.; Scott, W. J. Palladium-Catalyzed Oxyhexatriene Cyclization: a Novel Approach to Cyclohexenone Annulation *J. Am. Chem. Soc.* 1991, 113, 4903-4910.

(40) Wang, J.; Cheng, B.; Li, J.; Zhang, Z.; Hong, W.; Chen, X.; Chen, P. R. Chemical Remodeling of Cell-Surface Sialic Acids through a Palladium-Triggered Bioorthogonal Elimination Reaction. *Angew. Chem. Int. Ed.* 2015, 54, 5364-5368.

(41) Elliott, E. L.; Ray, C. R.; Kraft, S.; Atkins, J. R.; Moore, J. S. Solid-Phase Synthesis of m-Phenylene Ethynylene Heterosequence Oligomers. *J Org. Chem.* 2006, 71, 5282-5290.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (I):

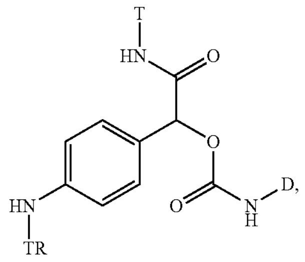

or a pharmaceutically acceptable salt thereof, wherein:

T is an anchoring moiety selected from $C_{8-22}$ alkyl chain, fatty acid, fatty monoglyceride, fatty diglyceride, and a phospholipid;

TR is a trigger-sensitive moiety selected from allyloxy carbonyl (alloc), propargyloxy carbonyl (poc), and (2E)-2-cycloocten-1-ol (3-OH TCO) that upon contact with a trigger reagent releases drug moiety D; and D is a drug moiety selected from monomethyl auristatin E (MMAE), doxorubicin and 4-methyl-7-aminocoumarin (AMC), wherein the anchoring moiety has affinity to a hydrophobic polymer or hydrophobic co-polymer.

2. The compound of claim 1, wherein the trigger reagent is a transition metal reagent or a nanoparticle comprising a transition metal.

3. The compound of claim 1, wherein the trigger-sensitive moiety is an alloc group or a poc group.

4. The compound of claim 1, wherein the trigger-sensitive moiety is 3-OH TCO.

5. The compound of claim 1, wherein the compound of Formula (I) is selected from:

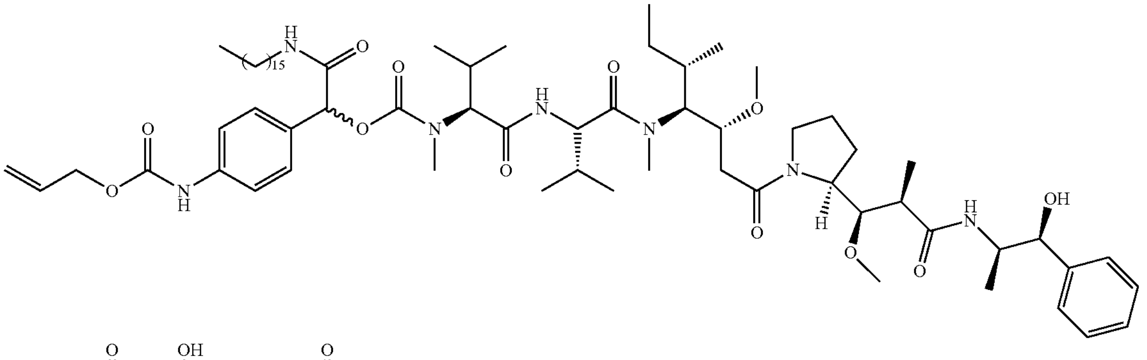

,

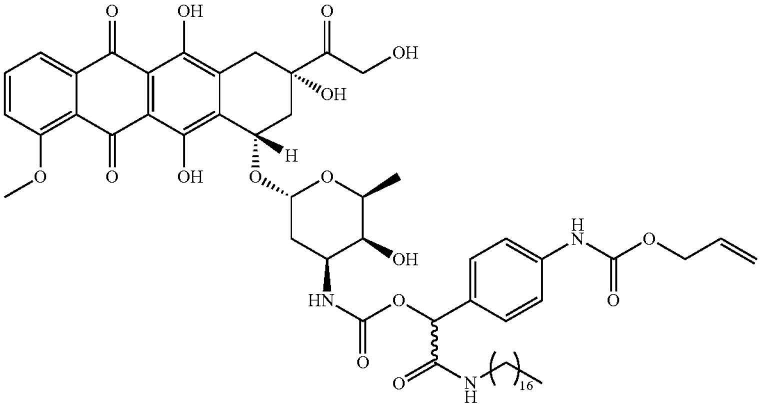

, and

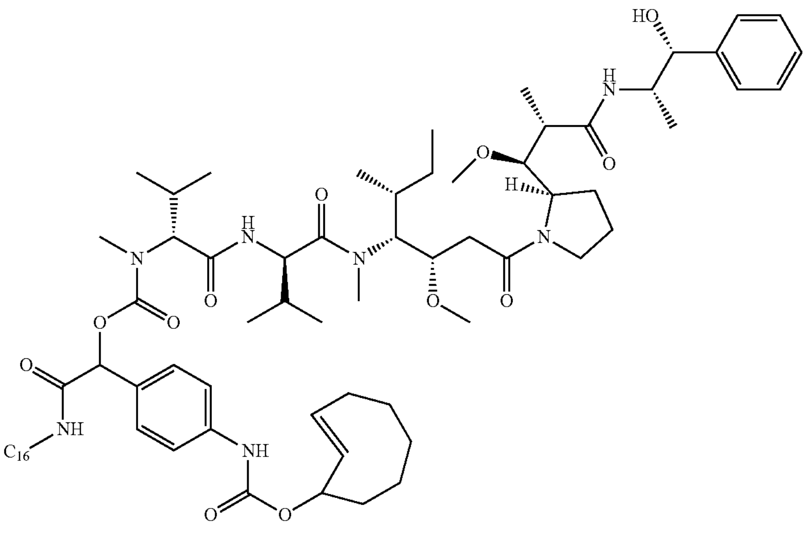

, or a pharmaceutically acceptable salt thereof.

6. A particle comprising a compound of Formula (I), or a pharmaceutically acceptable salt thereof, of claim 1.

7. The particle of claim 6, wherein the particle comprises a hydrophobic core comprising the compound of Formula (I), or a pharmaceutically acceptable salt thereof.

8. The particle of claim 6, wherein the particle comprises a hydrophilic shell.

9. The particle of claim 6, wherein the particle is a nanoparticle and the nanoparticle comprises an amphiphilic polymer selected from poly(ethylene glycol)-co-poly(D,L-lactic acid) (PLA-PEG) and poly(ethylene glycol)-co-(poly(lactide-co-glycolide)) (PLGA-PEG).

10. A method of treating a disease or condition in a subject, the method comprising administering to the subject in need thereof a compound of Formula (I), or a pharmaceutically acceptable salt thereof, of claim 1, wherein the disease or condition is treatable by the drug D as provided in Formula (I).

11. The method of claim 10, wherein the drug D is an anticancer agent and the disease is cancer.

12. The method of claim 10, further comprising administering to the subject a trigger reagent.

13. The method of claim 12, wherein the trigger reagent comprises a transition metal, a glutathione, a protease, a peptidase, an acid, or a bioorthogonal click reagent.

14. The method of claim 13, wherein the bioorthogonal click reagent comprises a tetrazine moiety.

15. The method of claim 12, wherein the trigger reagent comprises a targeting moiety that directs the delivery of the trigger reagent to the cell or tissue of the subject where treatment of the disease or condition is desired.

16. The compound of claim 1, wherein the anchoring moiety is anchored to a hydrophobic substance.

17. The anchored compound of claim 16, wherein the hydrophobic substance is selected from the hydrophobic core of a synthetic polymer nanoparticle, serum albumin, lipid , or other hydrophobic environment.

* * * * *